United States Patent
Bonadio et al.

(10) Patent No.: US 6,578,577 B2
(45) Date of Patent: Jun. 17, 2003

(54) LAPAROSCOPIC SEALED ACCESS DEVICE

(75) Inventors: Frank Bonadio, Bray (IE); Ronan Bernard McManus, Bray (IE); Derek William Young, Blackrock (IE); Alan Reid, Clontarf (IE); Alfred Cushieri, Fife (GB)

(73) Assignee: Atropos Limited, Wicklow (IE)

( * ) Notice: Subject to any disclaimer, the term of this patent is extended or adjusted under 35 U.S.C. 154(b) by 128 days.

(21) Appl. No.: 09/804,552

(22) Filed: Mar. 13, 2001

(65) Prior Publication Data

US 2002/0072762 A1 Jun. 13, 2002

Related U.S. Application Data

(63) Continuation of application No. PCT/IE99/00123, filed on Dec. 1, 1999.

(30) Foreign Application Priority Data

| Dec. 1, 1998 | (IE) | 980999 |
| Feb. 15, 1999 | (IE) | 990107 |
| Feb. 15, 1999 | (IE) | 990108 |
| Feb. 15, 1999 | (IE) | 990110 |
| Feb. 15, 1999 | (IE) | 990112 |
| May 24, 1999 | (IE) | 990416 |

(51) Int. Cl.$^7$ ............................................. A61B 19/08
(52) U.S. Cl. ........................ 128/850; 128/856; 606/108; 604/513; 604/539; 600/207
(58) Field of Search ................ 602/3, 13, 22, 602/63; 606/202, 1, 108; 128/849, 850, 851, 852, 853, 854, 855, 856; 600/204, 206, 207, 208; 604/513, 264, 539

(56) References Cited

U.S. PATENT DOCUMENTS

| 1,598,284 A | 8/1926 | Kinney |
| 3,244,169 A | 4/1966 | Baxter .......................... 128/82 |
| 3,347,226 A | 10/1967 | Harrower |
| 3,347,227 A | 10/1967 | Harrower |
| 3,397,692 A | 8/1968 | Creager, Jr. et al. |
| 3,522,800 A | 8/1970 | Lesser |
| 3,797,478 A | 3/1974 | Walsh et al. .................... 128/1 |
| 3,915,171 A | 10/1975 | Shermeta ..................... 128/348 |
| 4,228,792 A | 10/1980 | Rhys-Davies ............... 128/24.3 |
| 5,045,070 A | 9/1991 | Grodecki et al. |
| 5,158,553 A | * 10/1992 | Berry et al. ........... 604/167.03 |
| 5,161,773 A | 11/1992 | Tower |
| 5,213,114 A | 5/1993 | Bailey, Jr. |
| 5,342,385 A | 8/1994 | Norelli et al. ............... 606/193 |
| 5,350,364 A | 9/1994 | Stephens et al. ............. 604/167 |
| 5,364,345 A | 11/1994 | Lowrey et al. |

(List continued on next page.)

FOREIGN PATENT DOCUMENTS

| DE | 3739532 | 12/1988 |
| DE | 3737121 A1 | 5/1989 |
| DE | 29600939 | 6/1998 |

(List continued on next page.)

OTHER PUBLICATIONS

Original Specification of Application No. 09/804,418, filed Mar. 13, 2001.

(List continued on next page.)

Primary Examiner—Linda C. Dvorak
Assistant Examiner—Jocelyn Ram
(74) Attorney, Agent, or Firm—Finnegan, Henderson, Farabow, Garrett & Dunner, LLP

(57) ABSTRACT

A hand access device for use in hand assisted laparoscopic surgery comprises a substantially tubular inflatable sleeve of pliable gas tight material having a twisted inner sleeve section and an outer sleeve section. The device has an inner O-ring for insertion through a wound opening in the abdominal wall and an outer O-ring for location outside of the wound opening. On insertion of a surgeon's arm the sleeve everts while monitoring a reduced lumen seal to the arm and a seal to the wound openings.

64 Claims, 41 Drawing Sheets

U.S. PATENT DOCUMENTS

| | | | |
|---|---|---|---|
| 5,366,478 A | 11/1994 | Brinkerhoff et al. | 660/213 |
| 5,391,156 A | 2/1995 | Hildwein et al. | |
| 5,480,410 A * | 1/1996 | Cuschieri et al. | 606/201 |
| 5,514,133 A | 5/1996 | Golub et al. | 606/1 |
| 5,522,791 A | 6/1996 | Leyva | 600/207 |
| 5,524,644 A | 6/1996 | Crook | 128/888 |
| 5,526,536 A | 6/1996 | Cartmill | 2/161.7 |
| 5,545,179 A | 8/1996 | Williamson, IV | 606/213 |
| 5,634,911 A | 6/1997 | Hermann et al. | 604/256 |
| 5,634,937 A * | 6/1997 | Mollenauer et al. | 604/115 |
| 5,636,645 A * | 6/1997 | Ou | 128/898 |
| 5,640,977 A | 6/1997 | Leahy et al. | 128/897 |
| 5,649,550 A | 7/1997 | Crook | |
| 5,653,705 A | 8/1997 | de la Torre et al. | 606/1 |
| 5,672,168 A | 9/1997 | de la Torre et al. | 606/1 |
| 5,741,234 A | 4/1998 | Aboul-Hosn | 604/174 |
| 5,741,298 A | 4/1998 | MacLeod | 606/213 |
| 5,803,921 A | 9/1998 | Bonadio | 606/1 |
| 5,810,721 A | 9/1998 | Mueller et al. | 600/206 |
| 5,813,409 A | 9/1998 | Leahy et al. | 128/897 |
| 5,832,925 A * | 11/1998 | Rothrum | 128/849 |
| 5,853,395 A | 12/1998 | Crook et al. | 604/174 |
| 5,899,208 A | 5/1999 | Bonadio | 128/897 |
| 5,906,577 A * | 5/1999 | Beane et al. | 600/206 |
| 5,947,922 A | 9/1999 | MacLeod | 604/27 |
| 5,957,913 A | 9/1999 | de la Torre et al. | 606/1 |
| 5,964,781 A | 10/1999 | Mollenauer et al. | 606/213 |
| 5,997,515 A | 12/1999 | de la Torre et al. | 604/256 |
| 6,033,426 A | 3/2000 | Kaji | 606/213 |
| 6,033,428 A | 3/2000 | Sardella | 606/213 |
| 6,042,573 A | 3/2000 | Lucey | 606/246 |
| 6,048,309 A | 4/2000 | Flom et al. | |
| 6,077,288 A | 6/2000 | Shimomura et al. | 606/185 |
| 6,110,154 A | 8/2000 | Shimomura et al. | 604/256 |
| 6,142,935 A | 11/2000 | Flom et al. | 600/206 |
| 6,142,936 A | 11/2000 | Beane et al. | 600/207 |
| 6,254,533 B1 | 7/2001 | Fadem et al. | |
| 6,254,534 B1 | 7/2001 | Butler et al. | |

FOREIGN PATENT DOCUMENTS

| | | |
|---|---|---|
| EP | 0 950 376 | 10/1999 |
| FR | 1456623 | 9/1966 |
| GB | 1 151 993 | 5/1969 |
| GB | 2 071 502 | 9/1981 |
| GB | 2 255 019 | 10/1992 |
| JP | 10-108868 | 4/1998 |
| WO | WO92/11880 | 7/1992 |
| WO | WO95/07056 | 3/1995 |
| WO | WO95/22289 | 8/1995 |
| WO | WO95/27445 | 10/1995 |
| WO | WO95/27468 | 10/1995 |
| WO | WO 96/36283 | 11/1996 |
| WO | WO 97/32514 | 9/1997 |
| WO | WO 97/32515 | 9/1997 |
| WO | WO98/35614 | 8/1998 |
| WO | WO98/48724 | 11/1998 |
| WO | WO 99/03416 | 1/1999 |
| WO | WO99/25268 | 5/1999 |
| WO | WO99/29250 | 6/1999 |
| WO | WO00/54675 | 9/2000 |
| WO | WO00/54676 | 9/2000 |
| WO | WO00/54677 | 9/2000 |
| WO | WO 01/08563 | 2/2001 |
| WO | WO 01/08581 | 2/2001 |
| WO | WO 00/32116 | 6/2001 |
| WO | WO 00/32119 | 6/2001 |
| WO | WO 00/32120 | 6/2001 |
| WO | WO 00/35356 | 6/2001 |

OTHER PUBLICATIONS

Original Specification of Application No. 09/688,333, filed Oct. 16, 2000.

Original Specification of Application No. 09/849,341, filed May 7, 2001.

Original Specification of Application No. 09/801,826, filed Mar. 9, 2001.

Original Specification of Application No. 09/867,593, filed May 31, 2001.

Original Specification of Application No. 09/867,403, filed May 31, 2001.

* cited by examiner

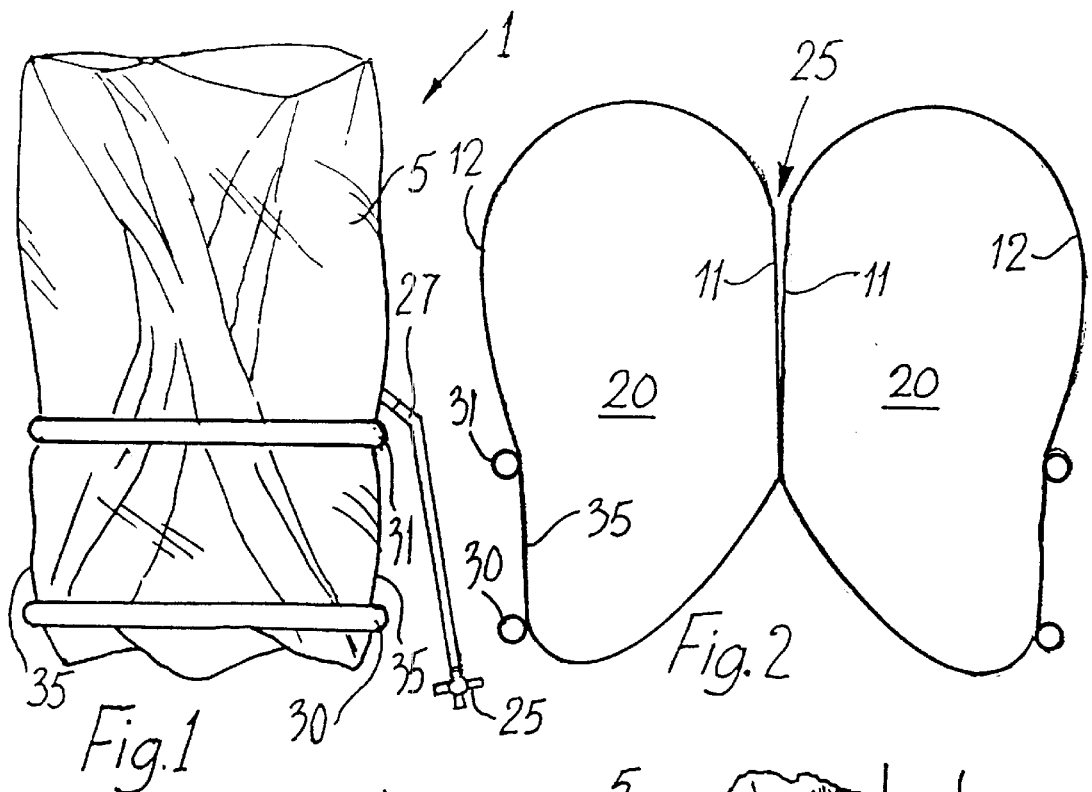
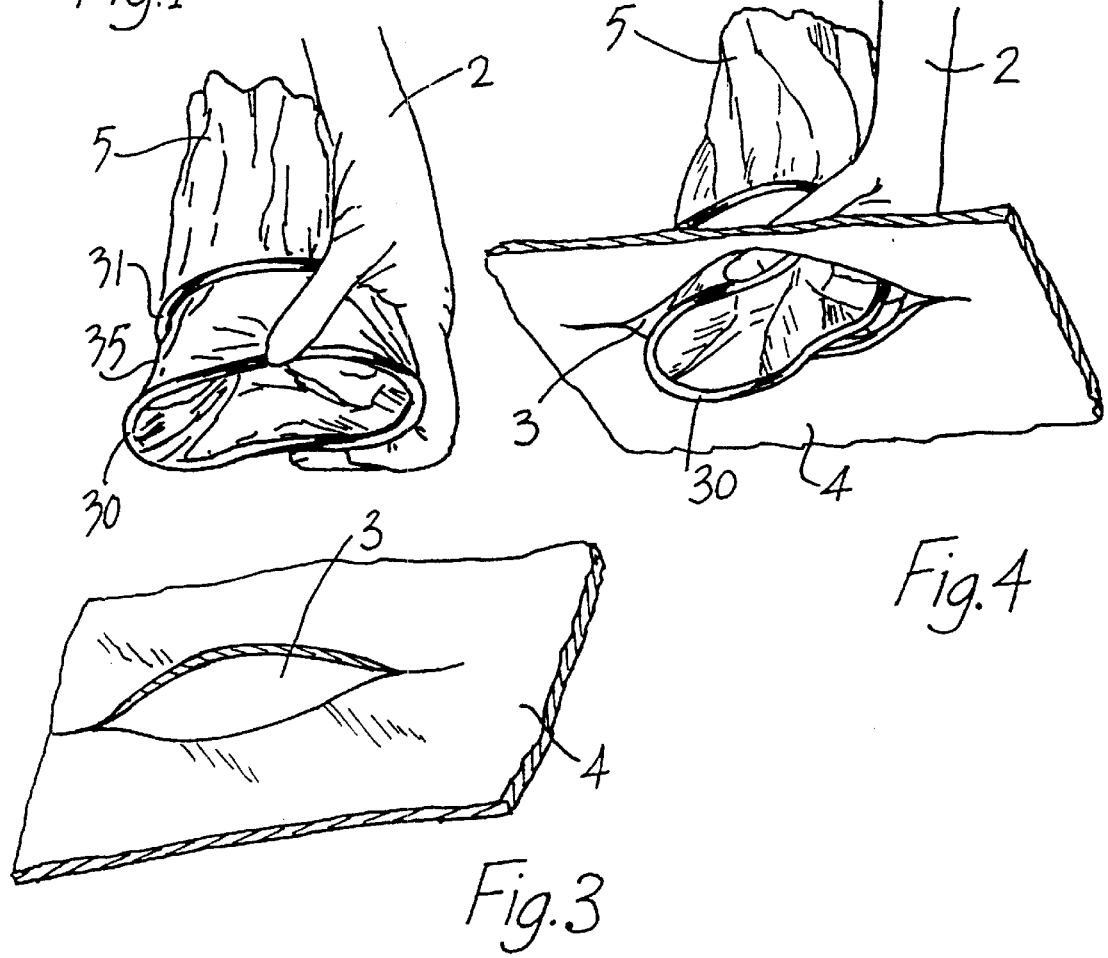

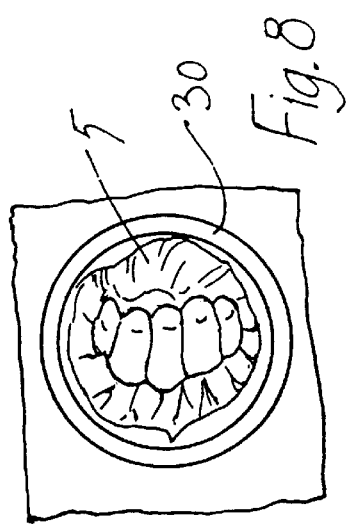
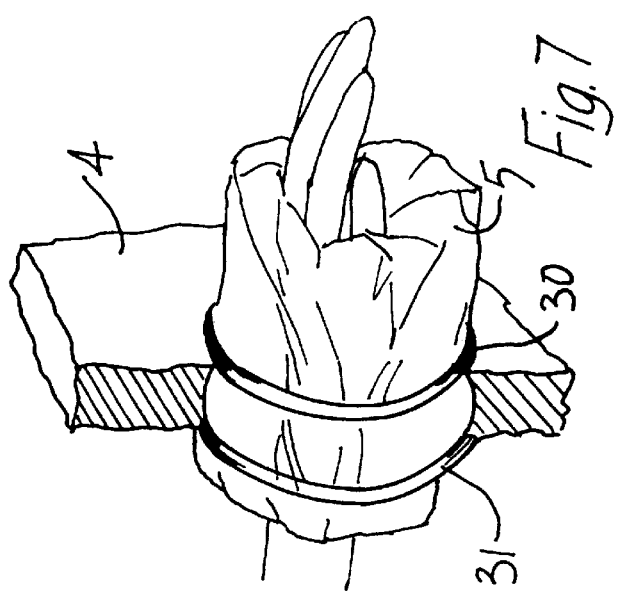
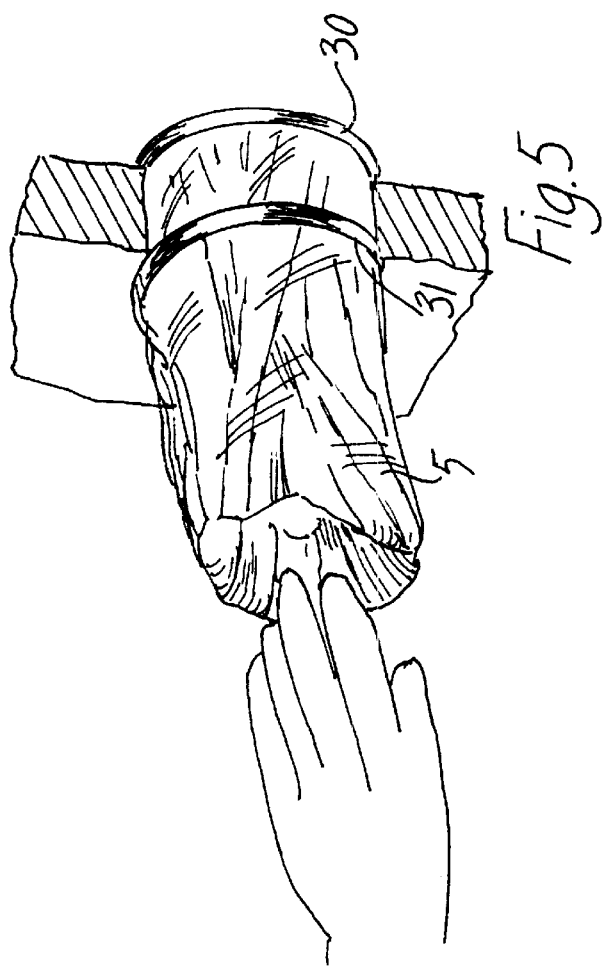
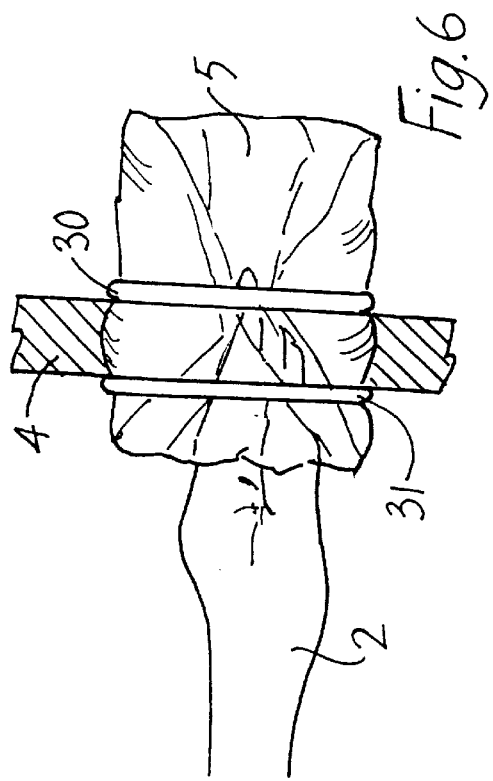

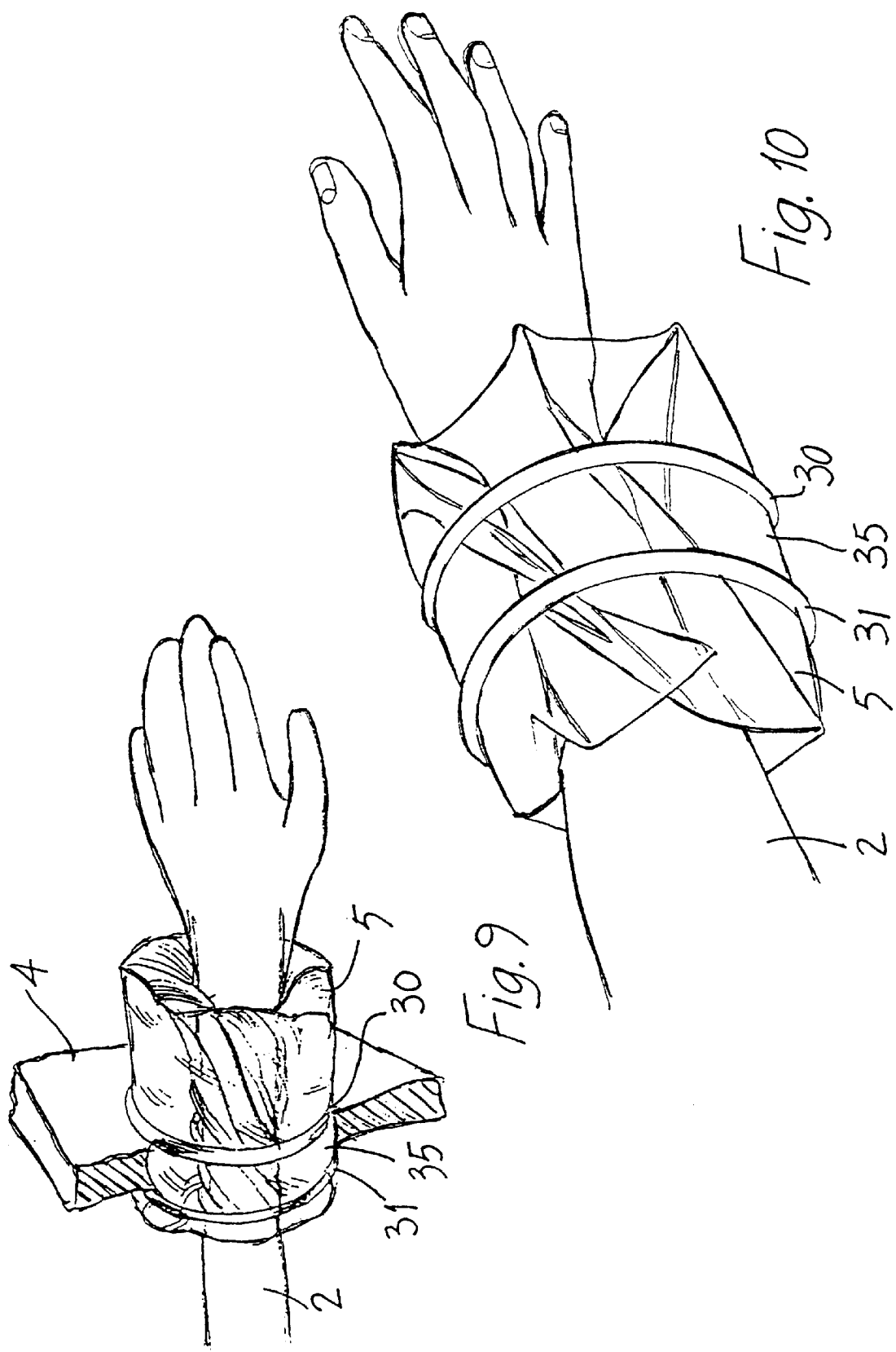

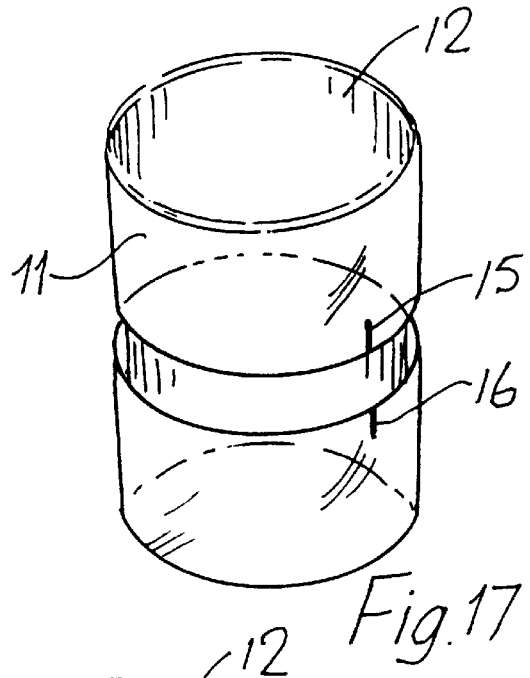
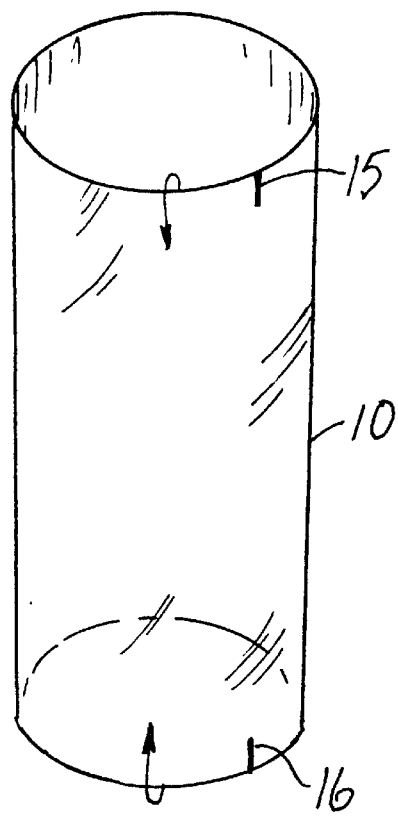
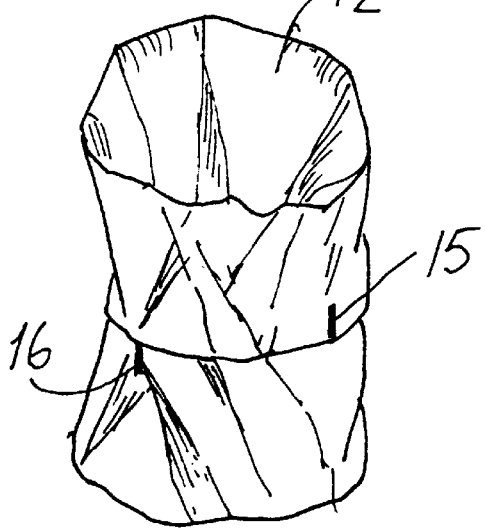
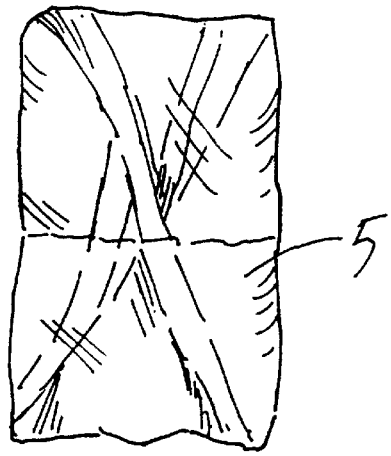
Fig. 16
Fig. 17
Fig. 18
Fig. 19

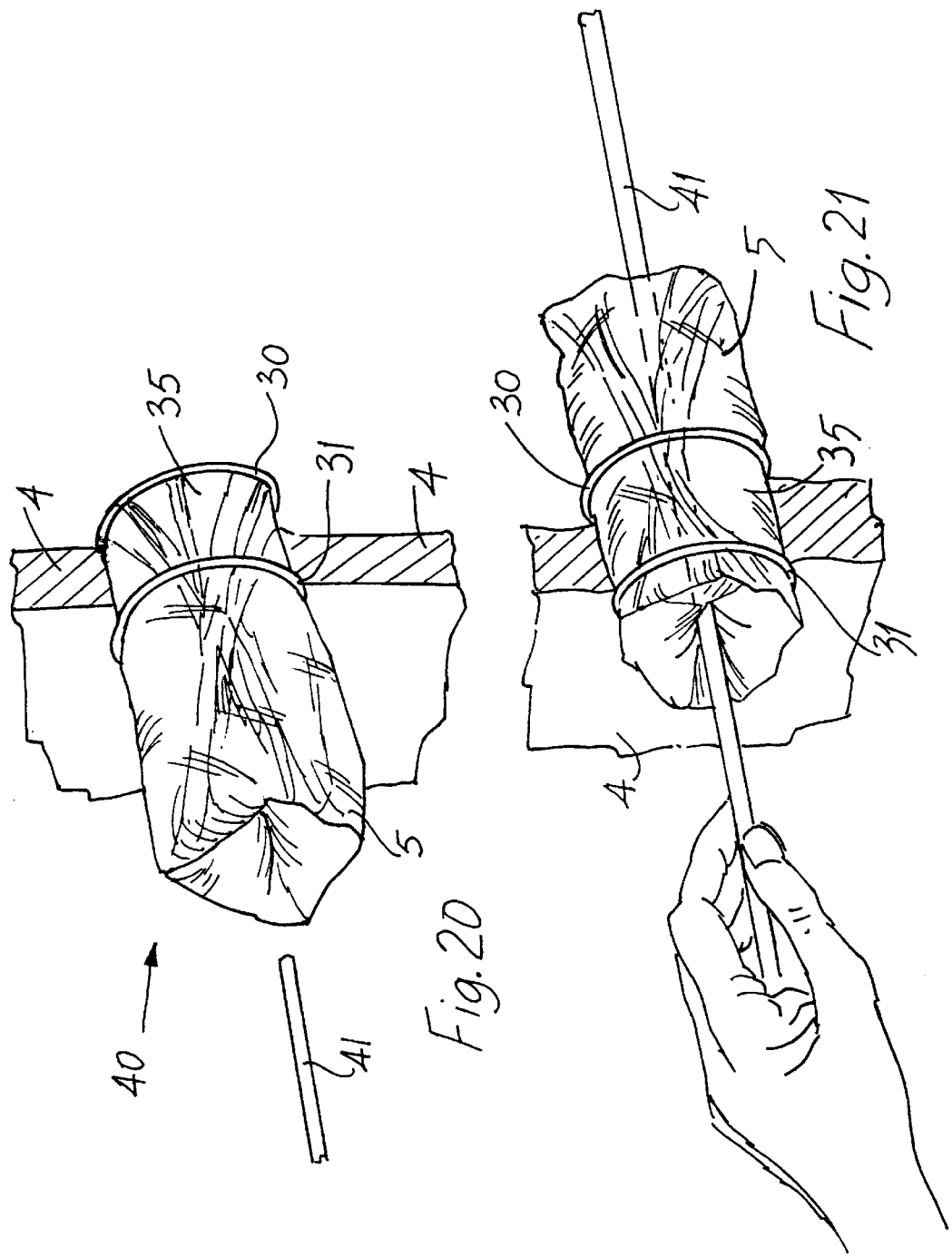

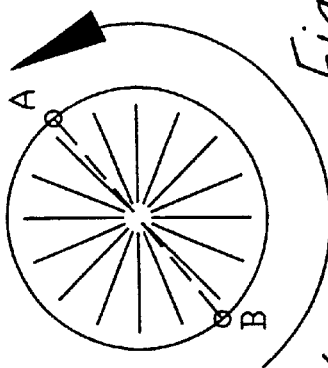
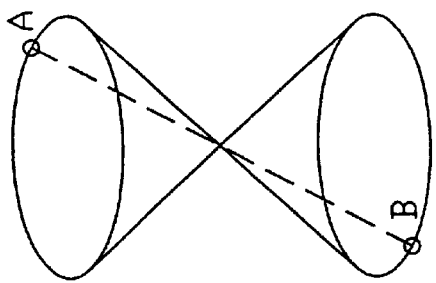
Fig. 38
Fig. 39
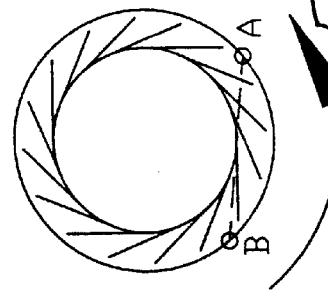
Fig. 36
Fig. 37
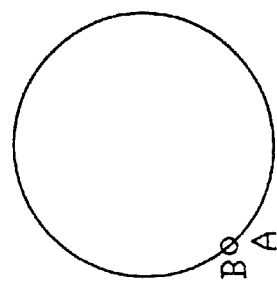
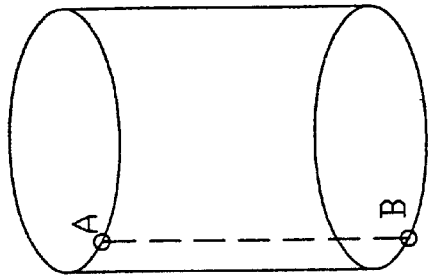
Fig. 34
Fig. 35

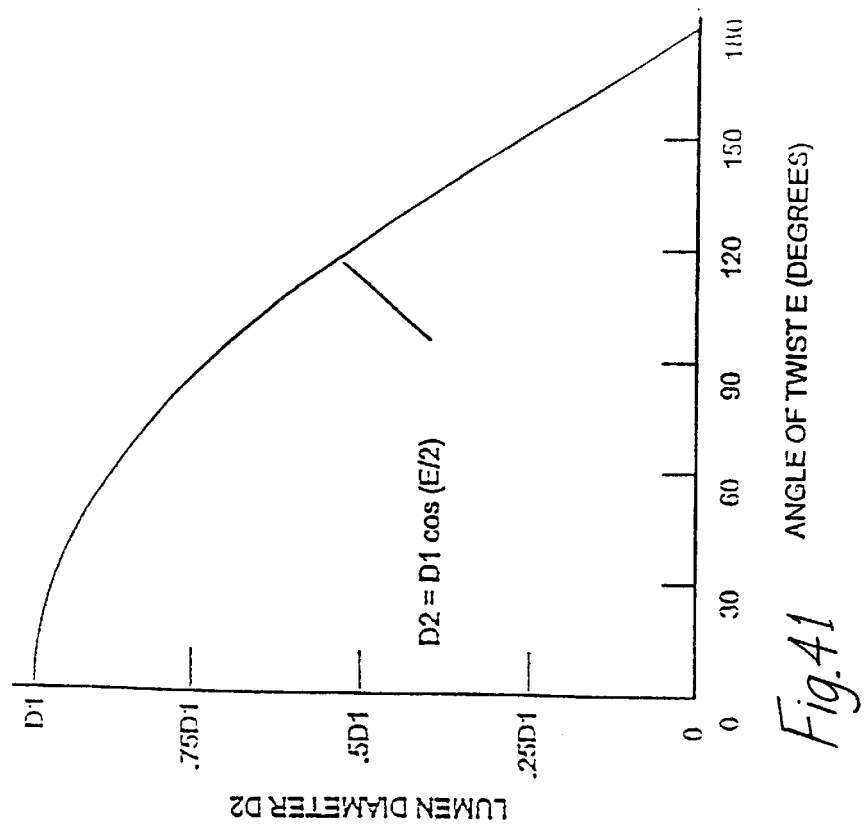
Fig. 41
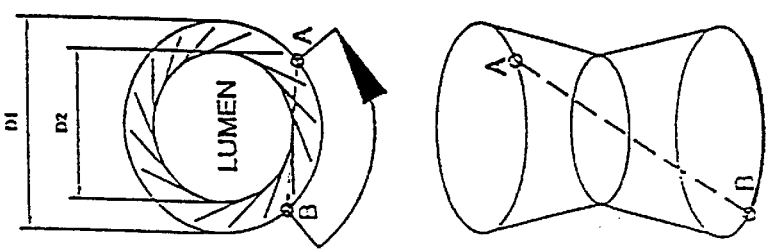
Fig. 40
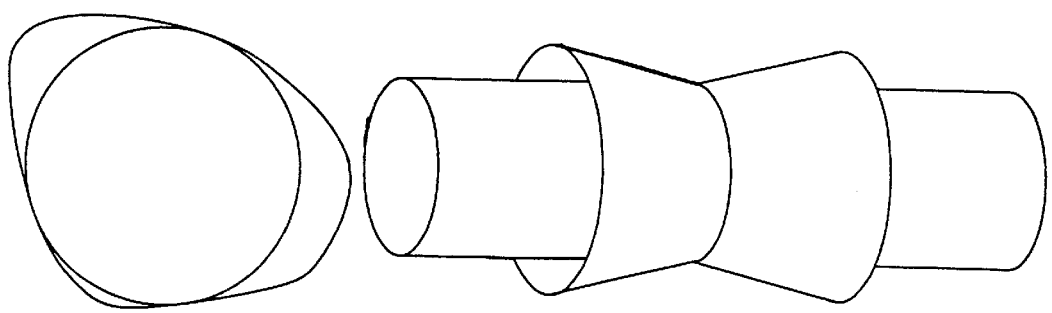
Fig. 43
Fig. 42

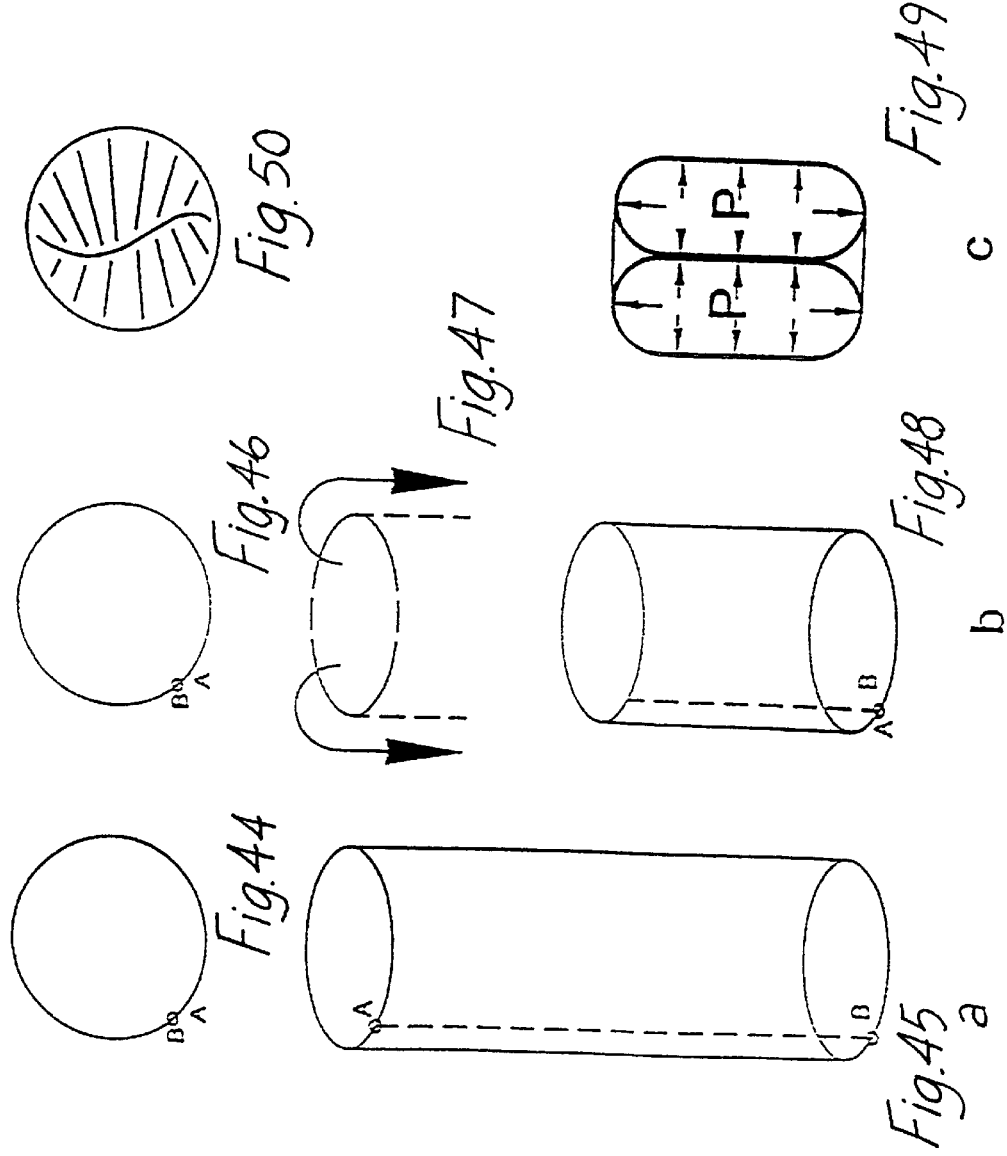

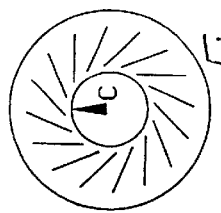
Fig.63
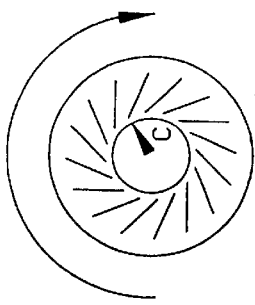
Fig.65
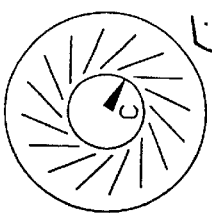
Fig.67
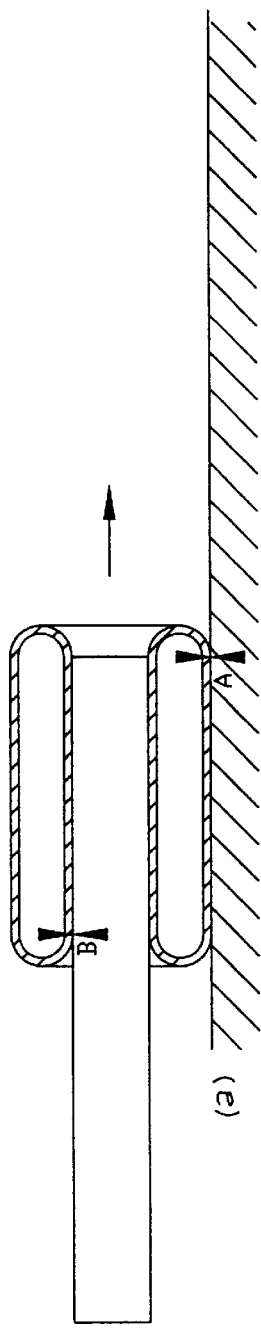
(a) Fig.62
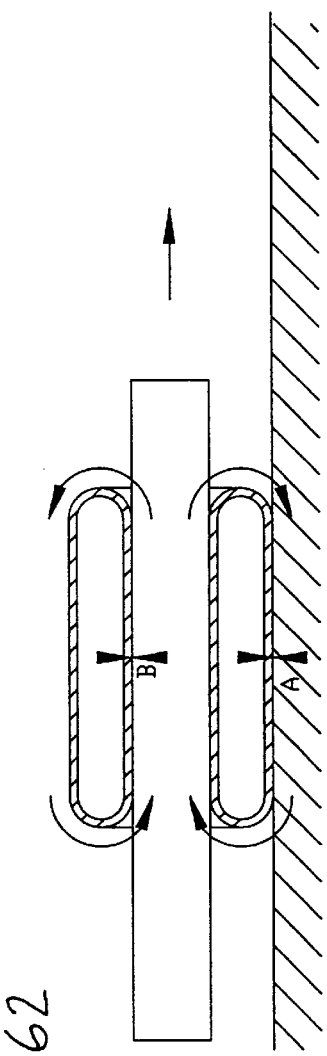
(b) Fig.64
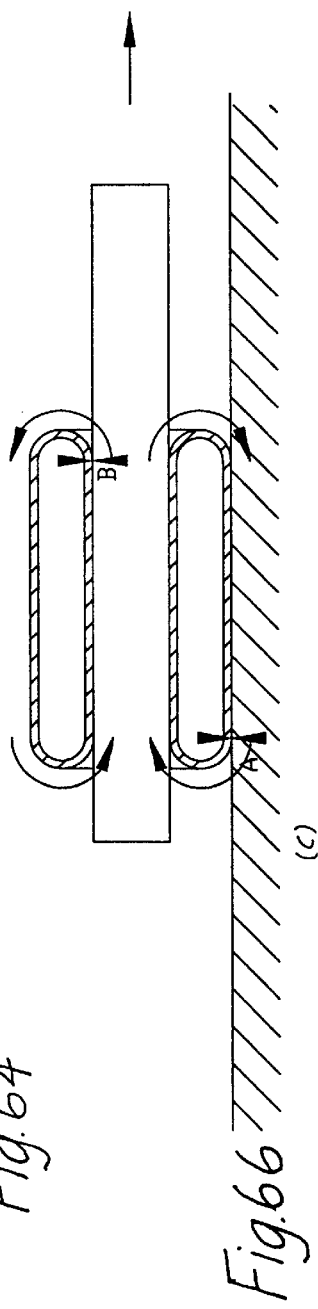
(c) Fig.66

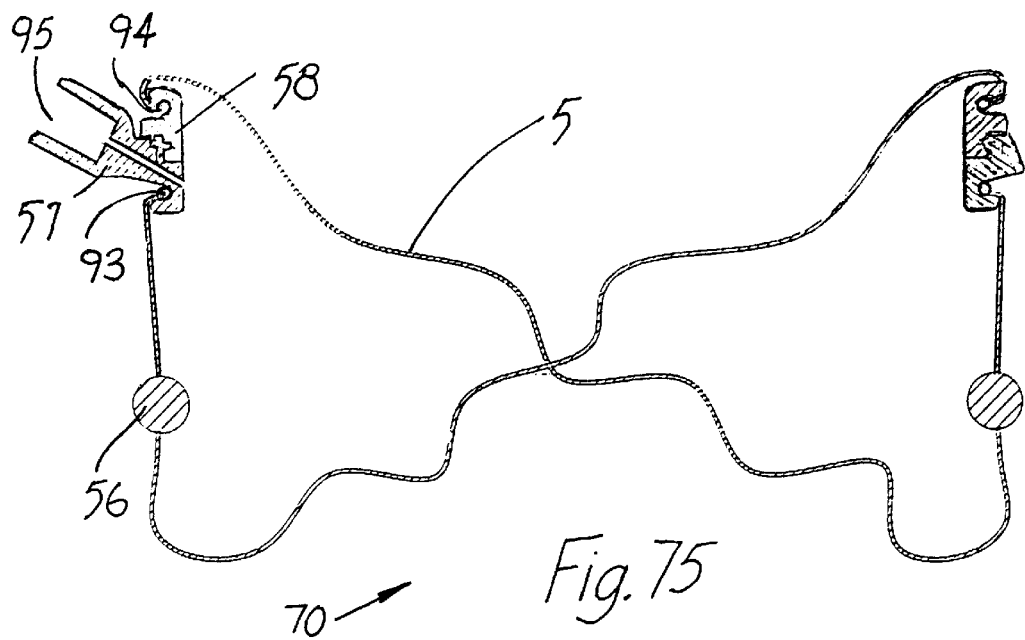
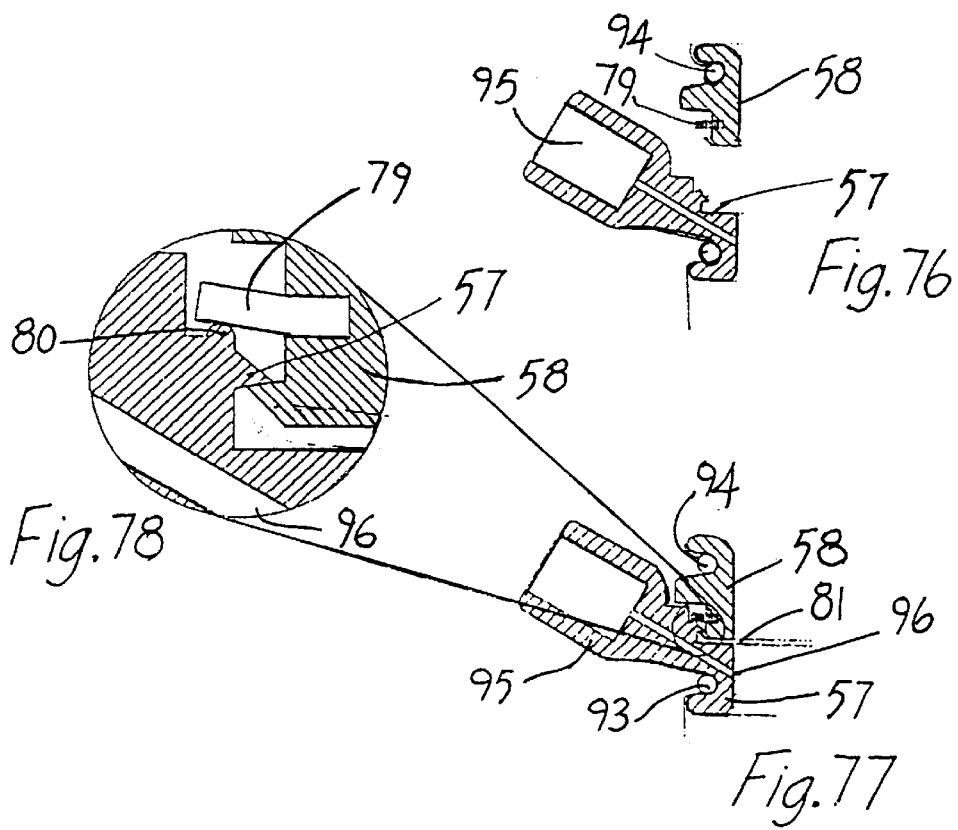

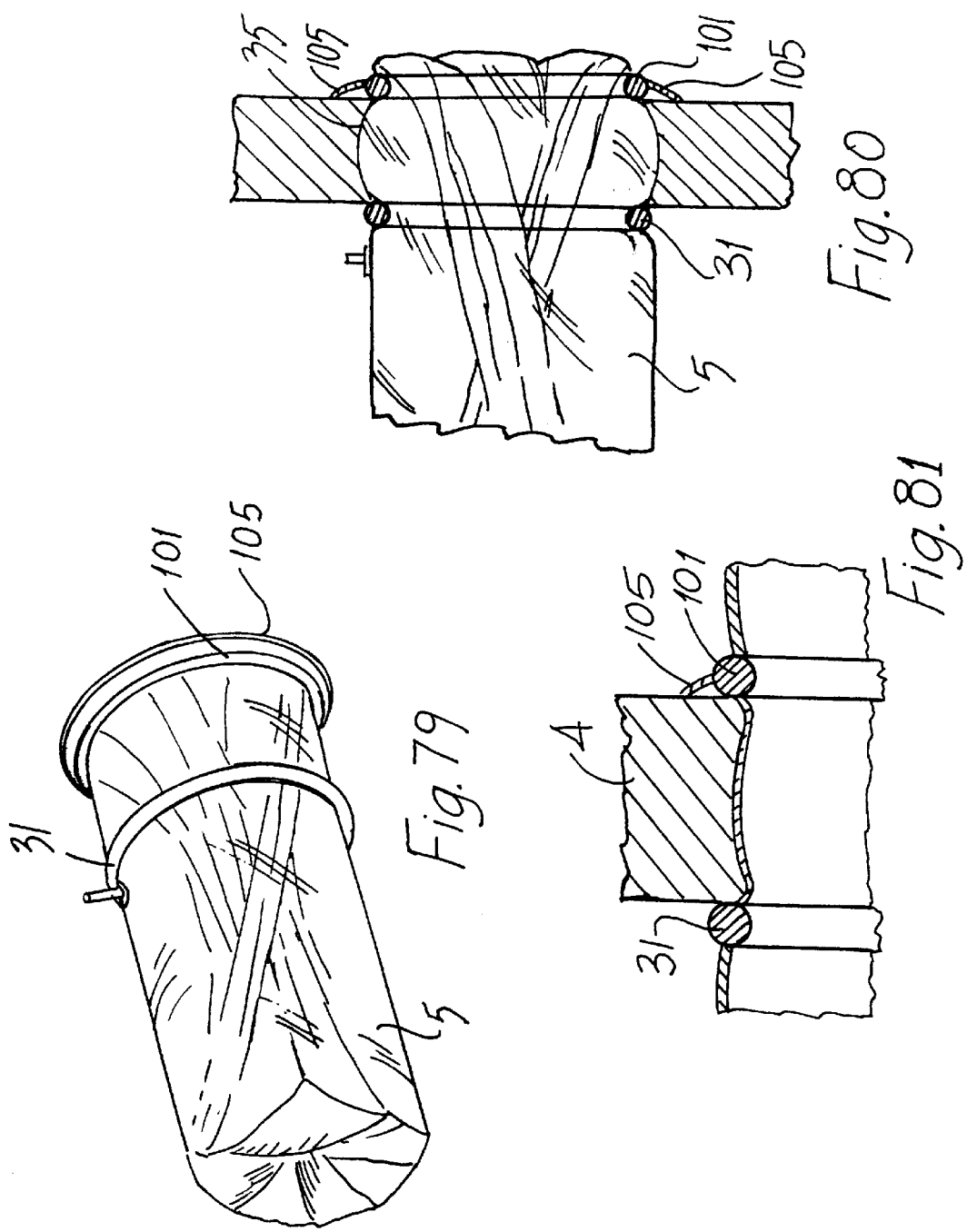

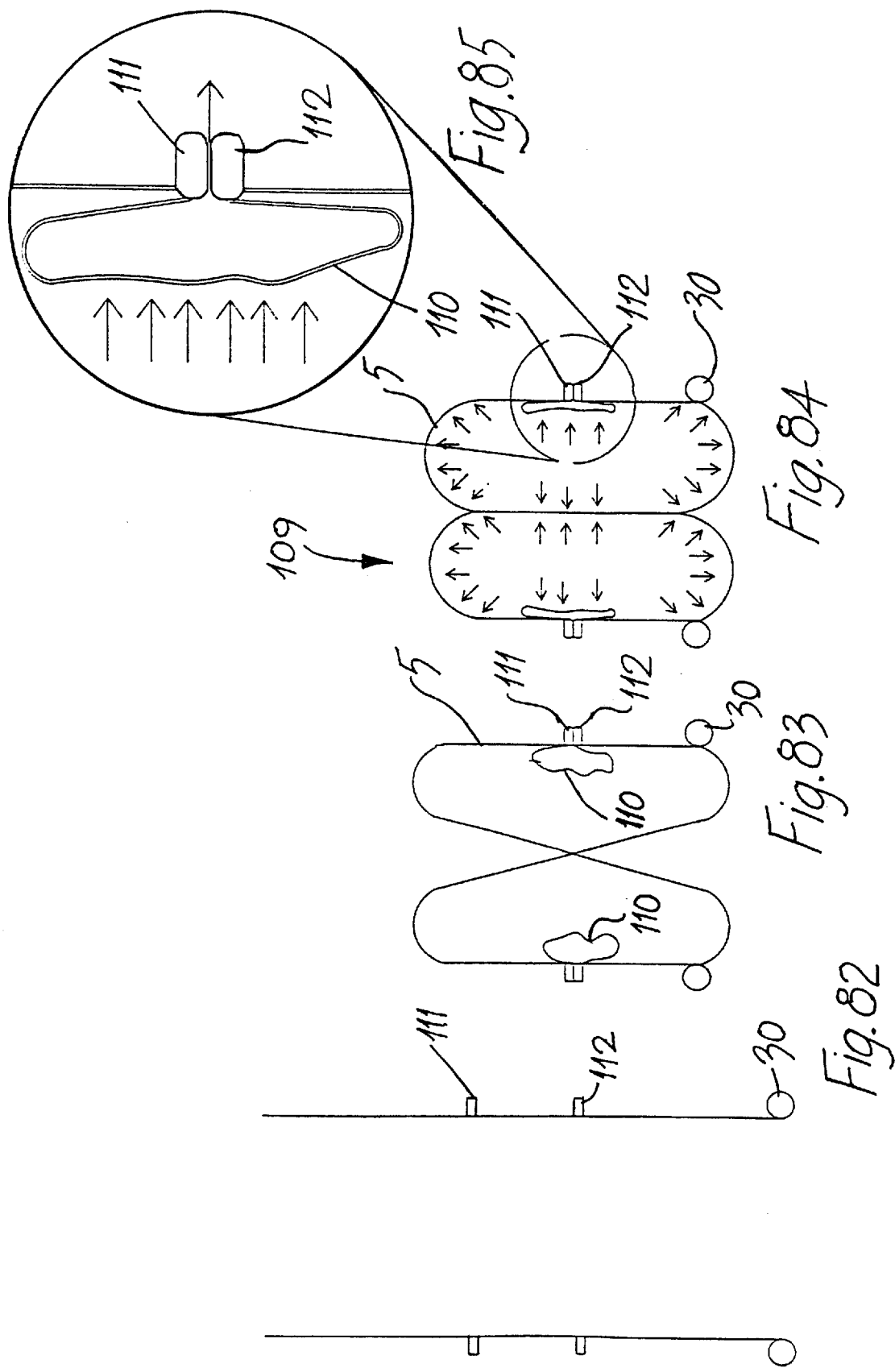

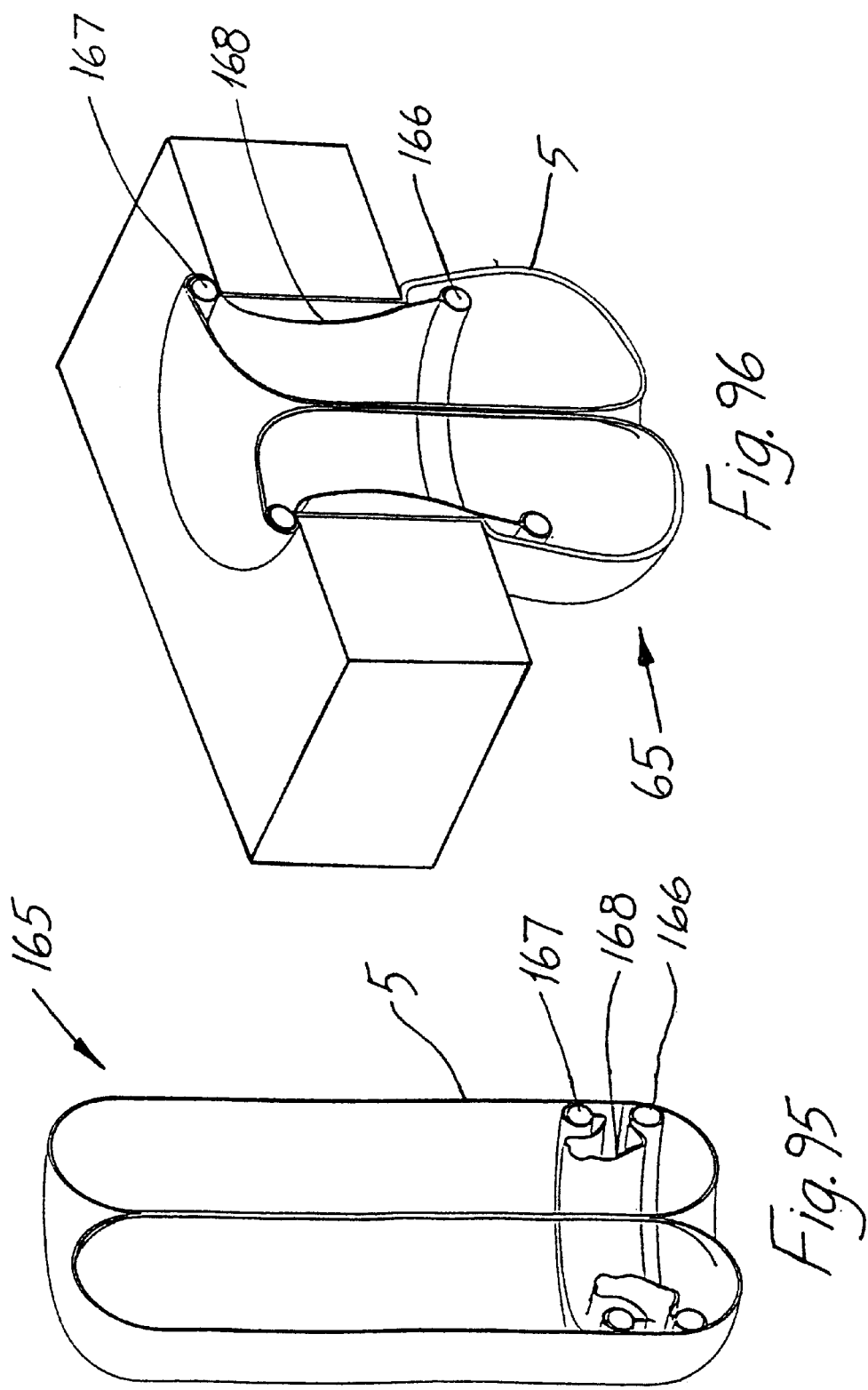

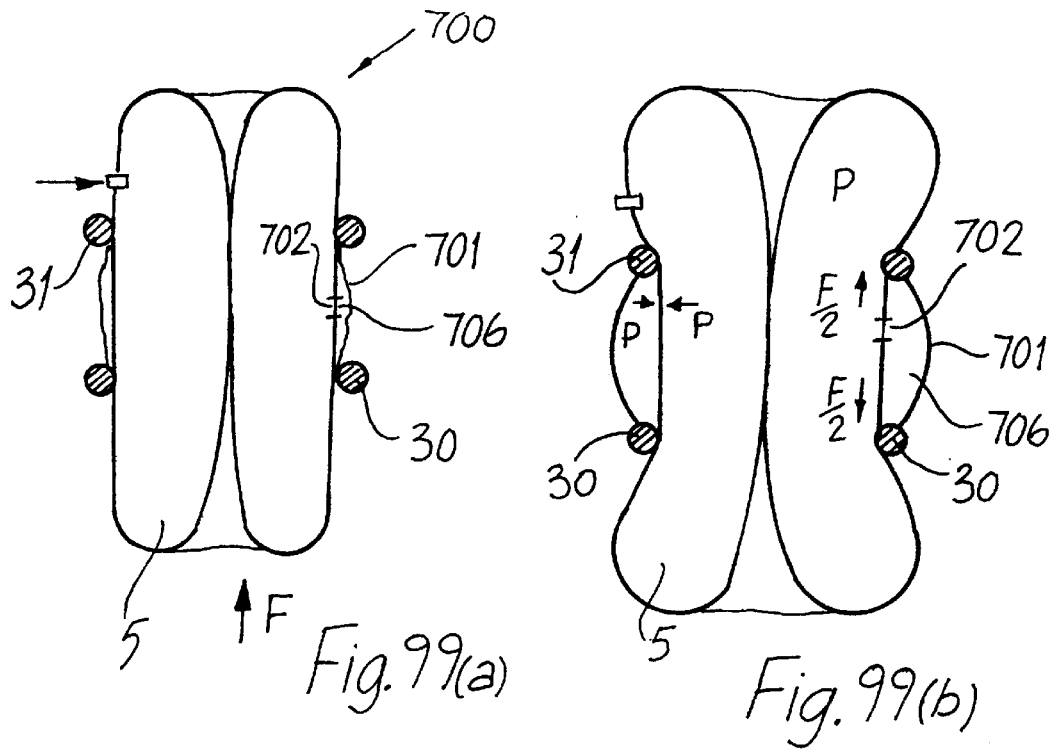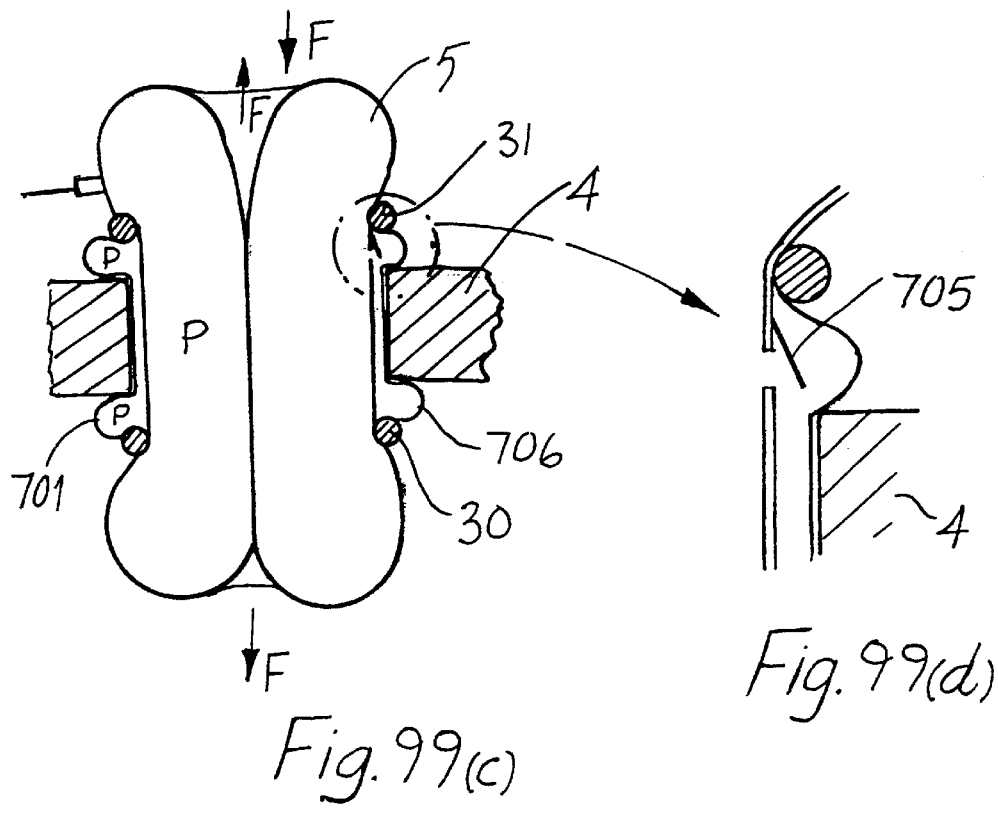

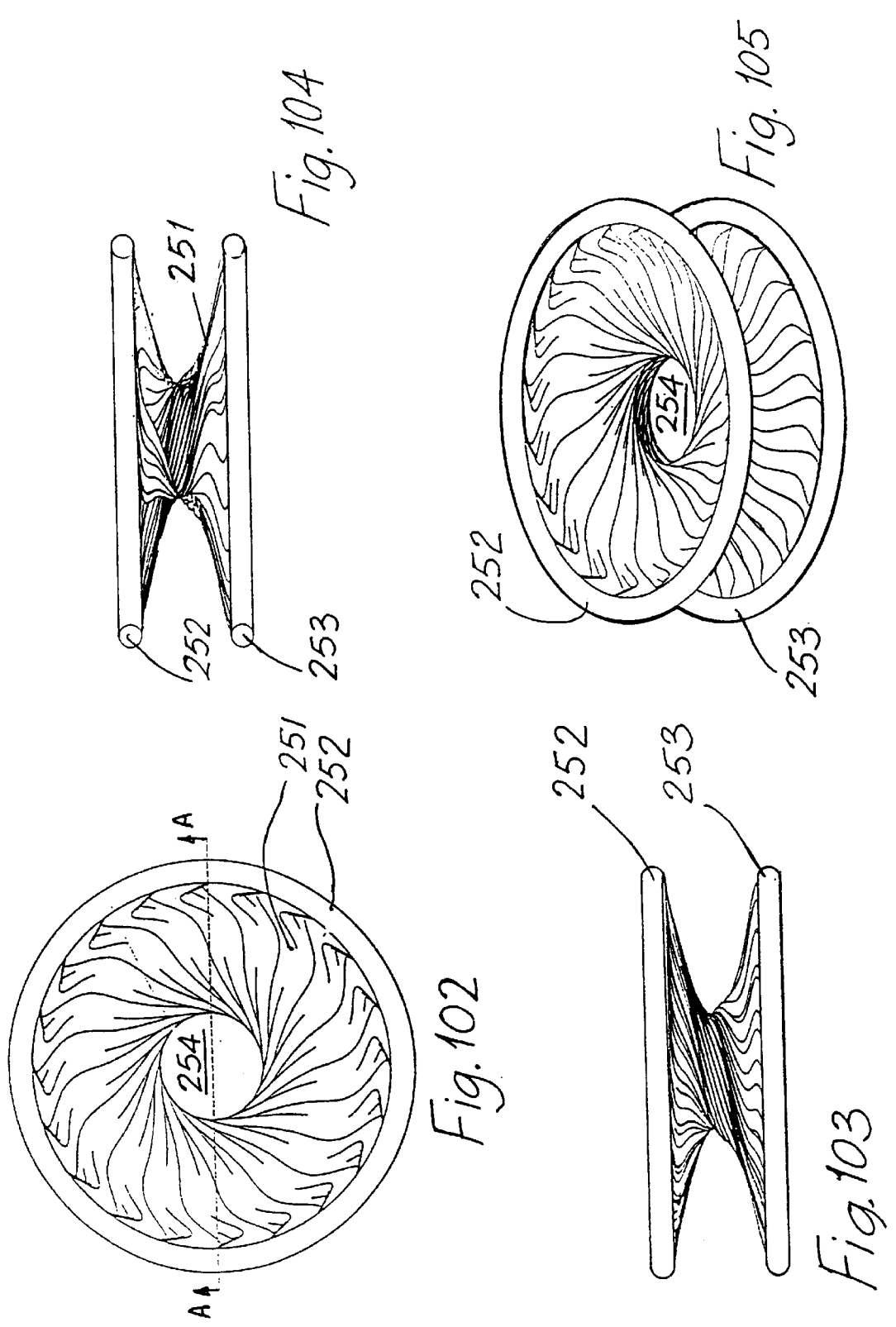

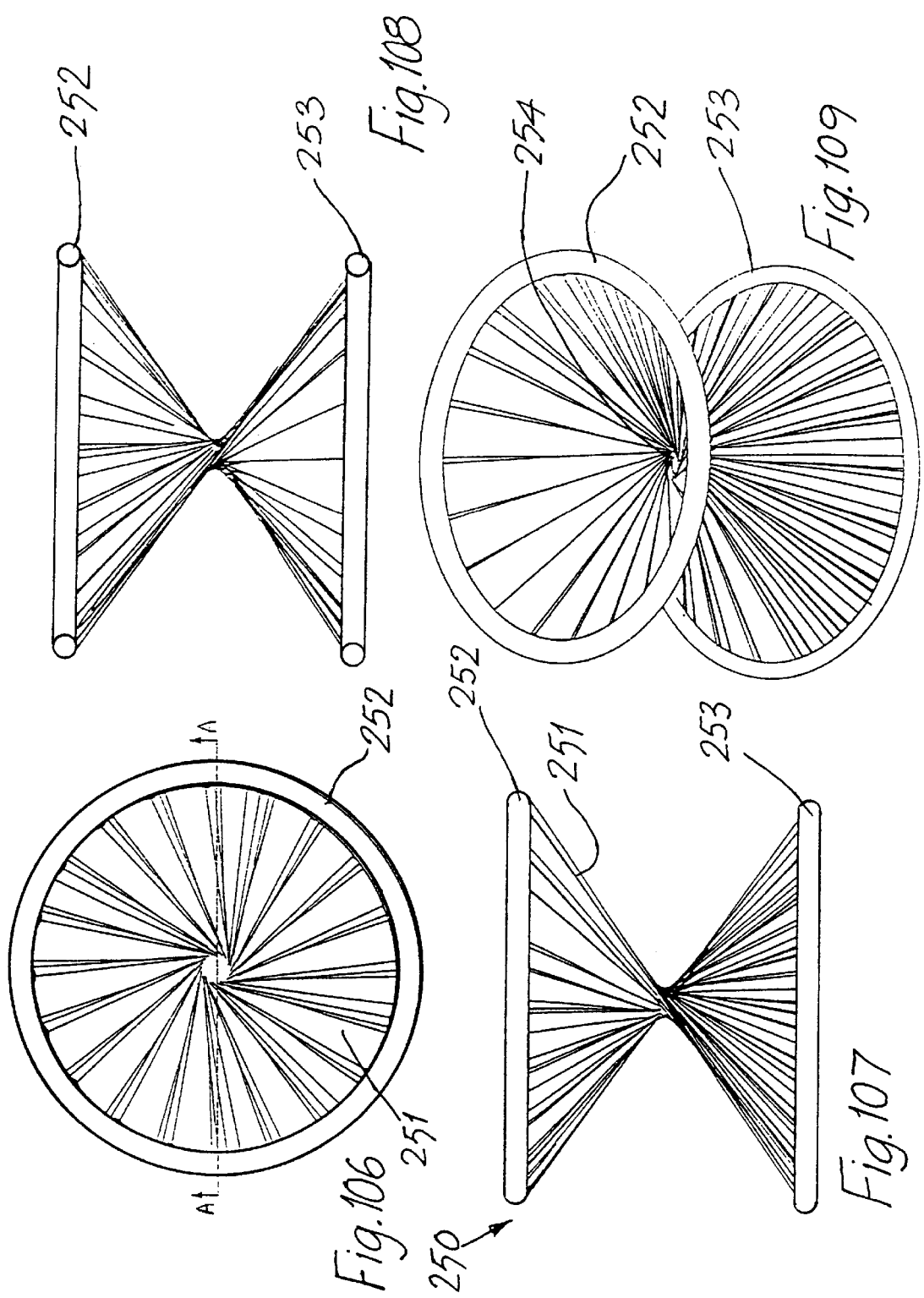

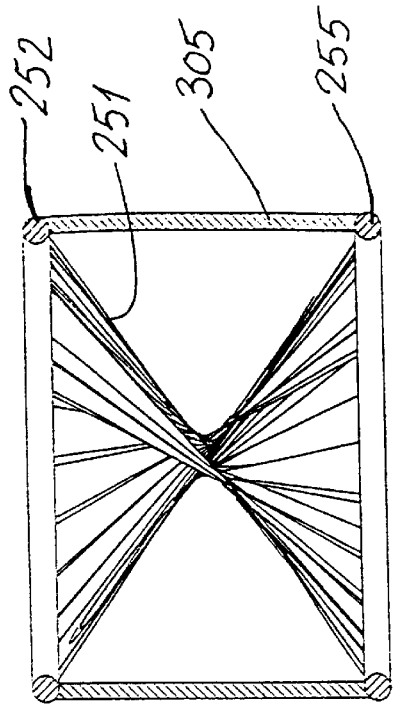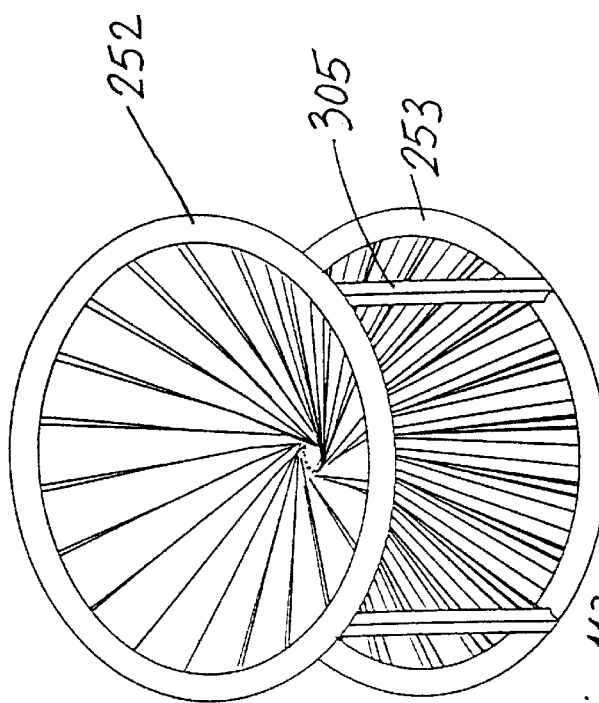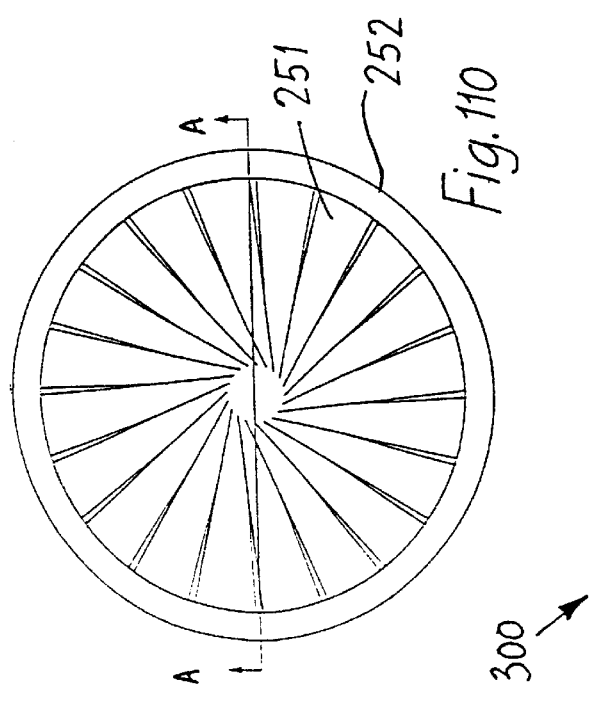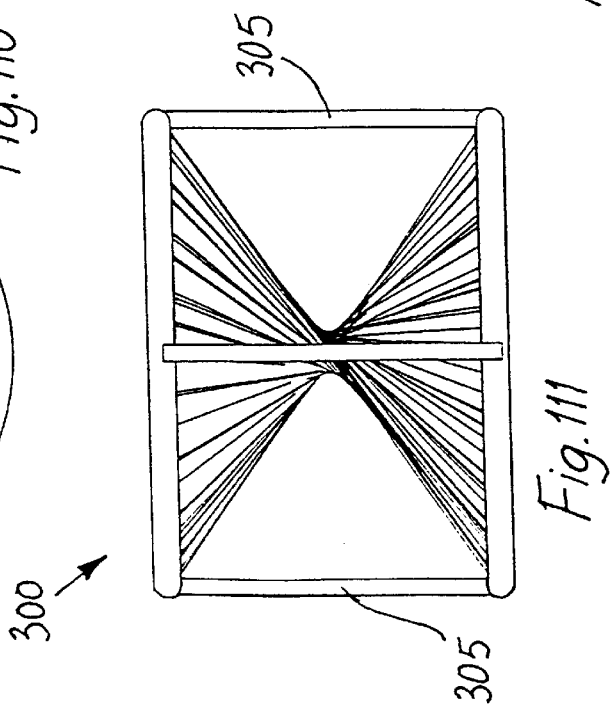

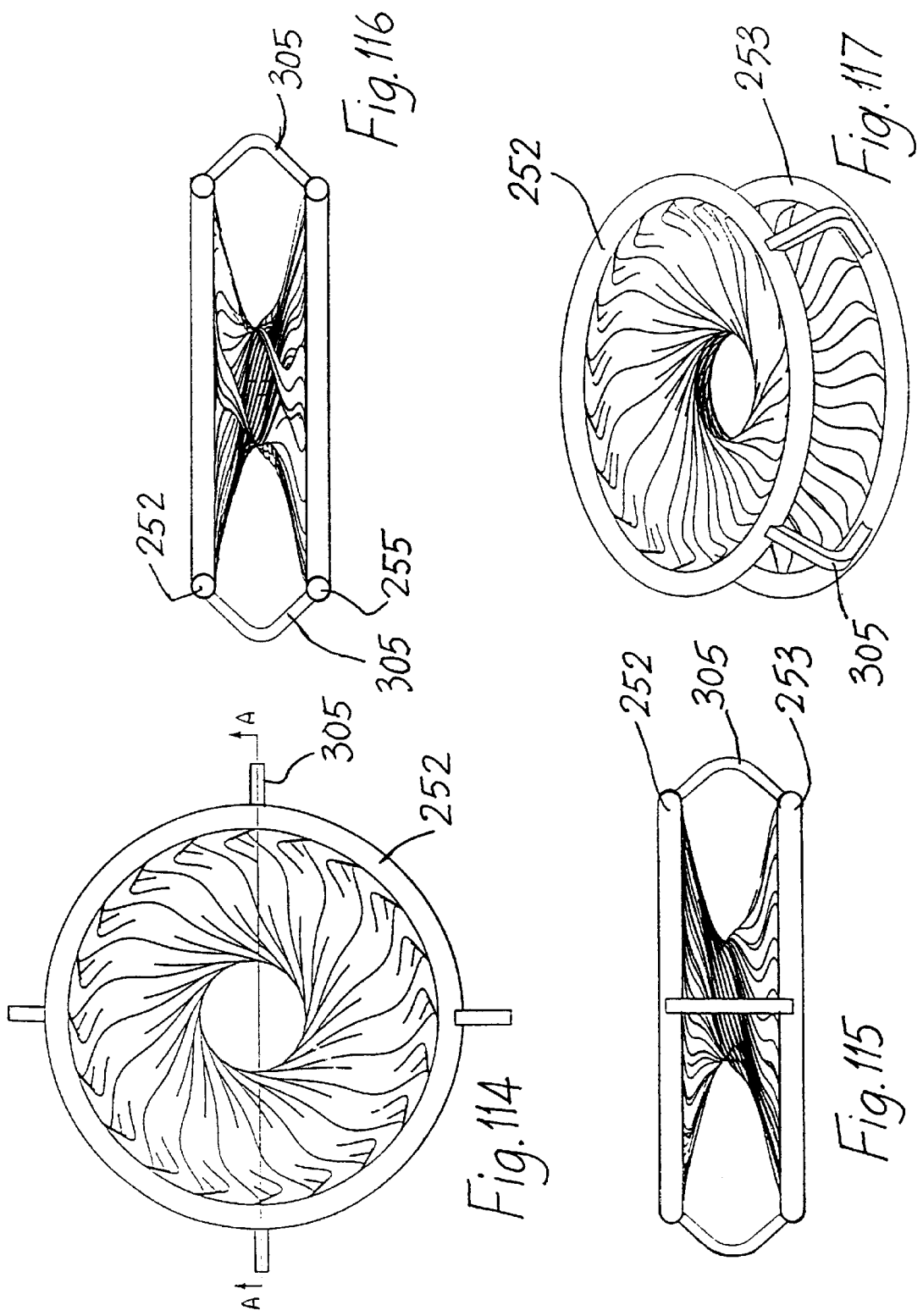

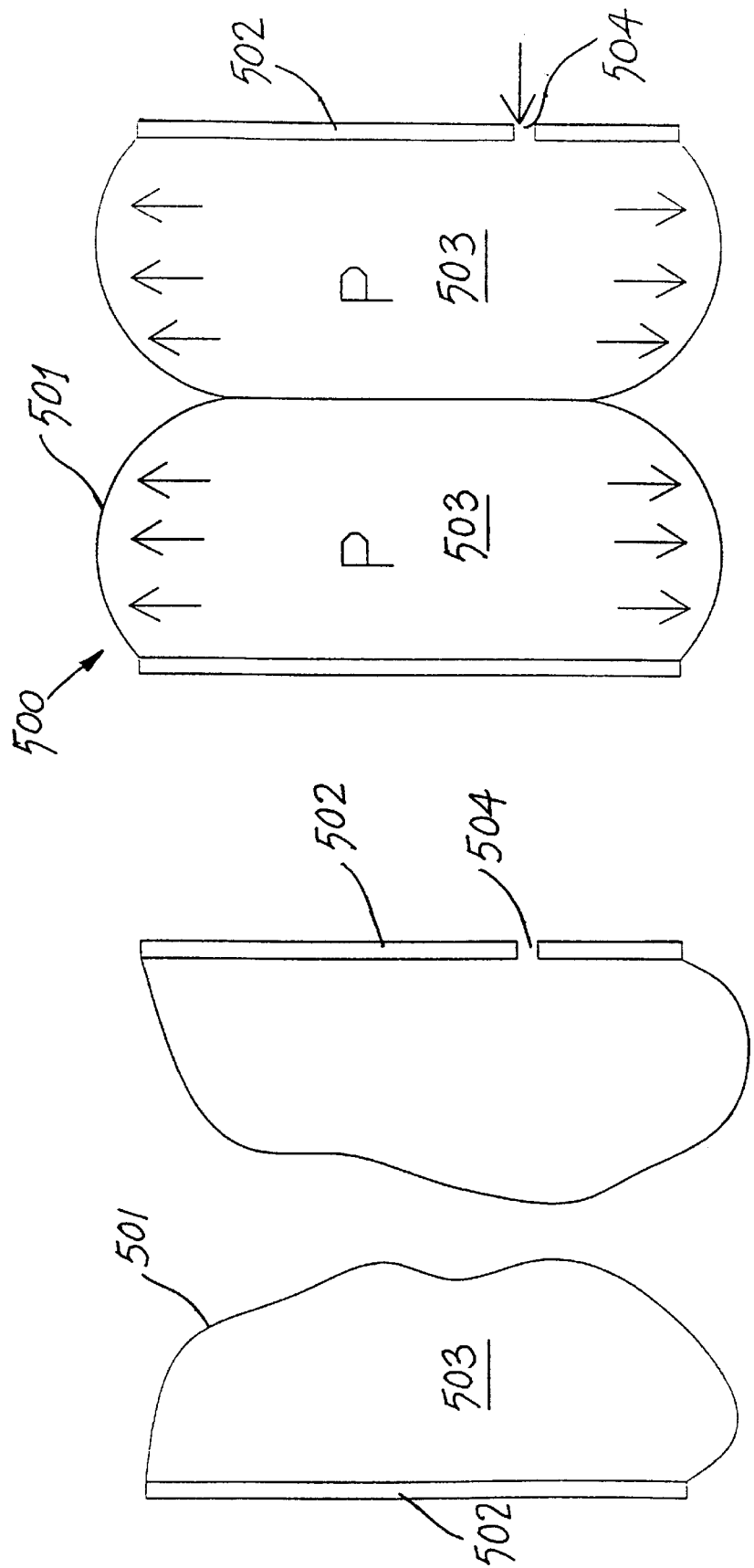

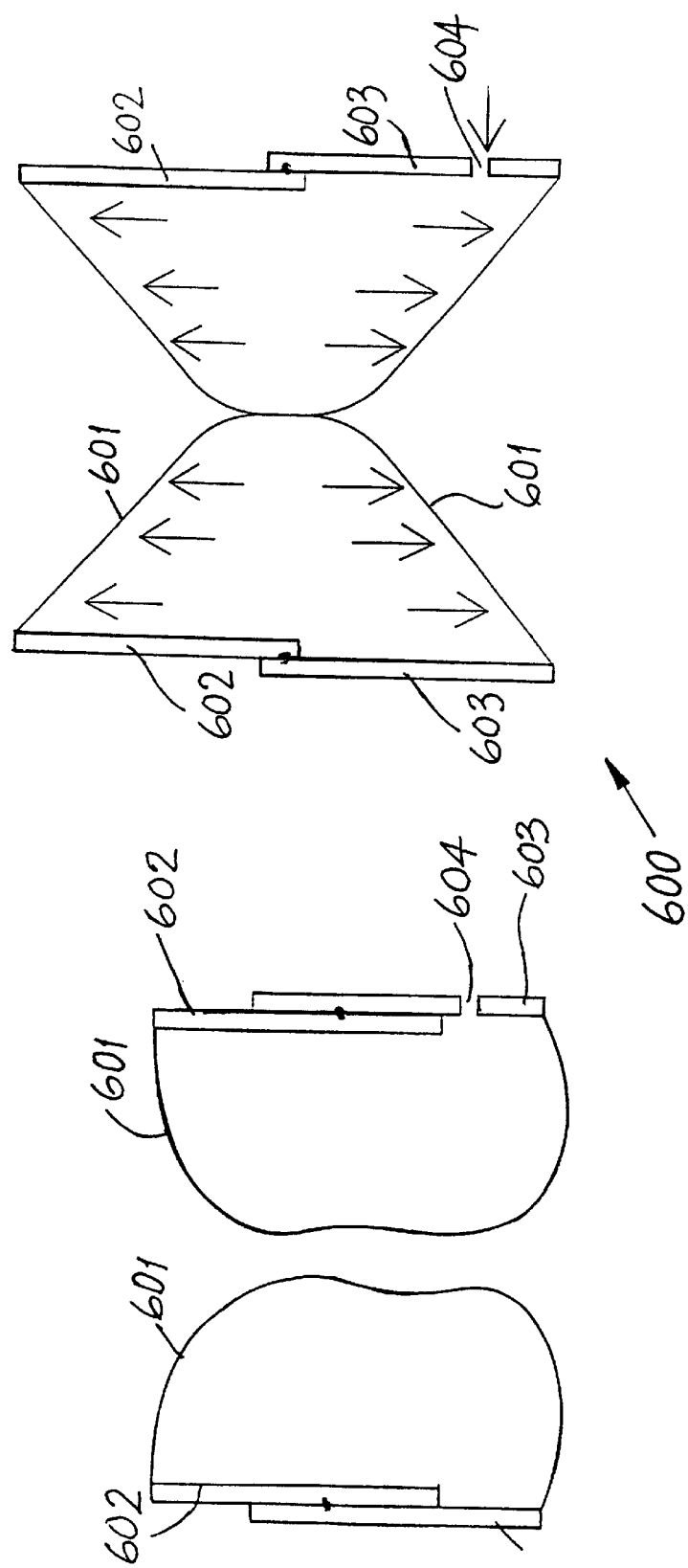

LAPAROSCOPIC SEALED ACCESS DEVICE

This application is a continuation of international application number PCT/IE99/00123, filed Dec. 1, 1999.

INTRODUCTION

The invention relates to a medical device particularly for use in surgery to provide surgical access to the abdomen and maintain a gas-tight seal around the arm or an instrument during surgery. Surgery of this type is referred to as hand-assisted laparoscopic surgery or hand-access surgery.

Conventional abdominal surgery requires the creation of an incision in the abdominal wall to allow access to, and visualization of the internal organs and other anatomical structures. These incisions must be large enough to accommodate the surgeons hands and any instruments to be utilised by the surgeon during the surgery. Traditionally the size of these incisions has been dictated by the need to see, retract and palpate internal bodily structures. While a large incision will provide access to the interior of the abdomen they are associated with longer healing times, are more susceptible to infection and result in unsightly scars.

Alternatives to open surgery exist in the form of endoscopic or laparoscopic surgery. In this method of surgery, the surgeon operates through small incisions using remotely actuated instruments. The instruments pass through the abdominal wall using devices called trocars. These working channels typically have a diameter ranging from 5 to 25 milimeters. Vision is provided using a laparoscope which is typically 20 to 25 centimeters long and uses fiber-optic technology or a CCD camera to provide the operator with a picture of the interior of the abdomen. The abdomen must be insufflated with a gas such as carbon dioxide or nitrogen to maintain a bubble effect and provide a viable working space for the operator to perform the surgery unhindered by the lack of space. This insufflation creates a working space known as the pneumoperitoneum. Trocars through which instruments are inserted are constructed to prevent loss of the gas through them resulting in collapse of the pneumoperitoneum.

The benefits of laparoscopic surgery are numerous. Recovery times have been shown to be reduced due to the absence of a large incision. This has benefits for the patient, the health care organisation and society. The benefits to the patient are reduced stay in hospital, faster mobilisation and return to normal activity. The benefits to the health care organisation is also due to the reduced stay in hospital which is often the most expensive aspect of health care provision. Society benefits in faster return to work and normal activity of the patient.

However, not all surgical procedures can be performed laparoscopically. Surgery requiring the removal of large organ specimens, such as surgery for removal of the colon, has traditionally been hampered by the small incisions used for the introduction of laparoscopic instruments in the surgery.

The other major disadvantages of laparoscopic surgery are due to the complex nature of the technique. Surgeons who wish to practise laparoscopic surgery must spend much time training to master the technique. The success of laparoscopic surgery depends on the skill of the surgeon to manipulate organs and carry out delicate tasks using remotely actuated instruments. Unfortunately in laparoscopic surgery the surgeon is insulated from the material that they are working on. This deprives the surgeon of tactile feedback and the ability to palpate delicate structures. The surgeon's most effective instrument, the hand, is reduced to a device that must simply actuate instruments that are inherently lacking in dexterity and operability due to the constraints on their design placed by the nature of the narrow channels in trocars through which they must pass. Another disadvantage of laparoscopy is that the image viewed by the surgeon is a two dimensional image on a video screen. The surgeon loses three dimensional perspective of depth and distance and awareness of the proximity of other structures during video laparoscopy.

These disadvantages have led to long learning curves for the practitioners of laparoscopic surgery, required highly skilled and coordinated surgical teams and has limited the application of laparoscopic surgery to relatively simple surgical procedures.

Recently, new surgical techniques have been developed that combine the advantages of both open surgery and laparoscopic surgery. In these new techniques surgery is carried out using a laparoscopic approach with the addition of a slightly larger incision to allow the surgeon to insert a hand into the insufflated abdomen. This is often referred to as hand-assisted laparoscopic surgery or HALS.

HALS allows surgeons to regain the tactile feedback and three-dimensional perspective lost in the conversion from open to laparoscopic procedures. It also permits rapid finger dissection, enhanced retraction capabilities and simplified haemostasis. There are several publications in the literature describing procedures carried out using a hand-assisted approach. These include total and sub-total colectomy, rectopexy, Nissen's fundoplication, gastrectomy, splenectomy, nephrectomy, pancreatectomy and others. Some of these procedures were previously performed using an open technique only. Over the past few years several centres have been investigating HALS with surgical device companies and increasing the literature on the subject. With the advent of surgical devices for facilitating HALS it is expected that more open surgical procedures will be converted to HALS procedures.

The key to the success of hand-assisted laproscopic surgery will be to provide a device that will seal to the wound edge and to a surgeons arm to maintain the pneumoperitoneum required. The device should provide freedom of movement including rotational, lateral and translational. In addition, it should be possible to use laparoscopic instruments with the device.

Various hand access devices have been proposed however, to date, no hand access device is available that adequately addresses these key issues.

U.S. Pat. No. 5,366,478 (Brinkerhoff et al) describes a device which is said to be for use during endoscopic surgery. The device has two inflatable toroidal sections connected by a transitional section. The transitional section is said to function to allow the passage of air from one toroid to the other toroid on inflation of the device. Each toroidal section contains a flexible stiffening ring. The stiffening ring in the outer toroid is illustrated in a position floating above the abdominal wall after inflation. It is not clear how this device provides a seal however in any event it would be difficult to pass an object such as a surgeon's forearm through a lumen in the transitional section, because of frictional resistance to the movement of the object relative to the transitional section.

A medical device for forming an external extension of the pneumoperitoneum is described in U.S. Pat. No. 5,480,410 (Cuschieri et al). The device includes an enclosure sealed into a trocar puncture site in an abdominal wall. Insufflation gas passes from the body cavity into the enclosure inflating it A number of valved openings are provided on the device to enable access to the enclosure interior.

In U.S. Pat. No. 5,514,133 (Golub et al) describes an endoscopic surgical apparatus, to enable a surgeon to access a surgical site through an opening. The apparatus includes two plates, which engage the outer and inner surfaces of the abdominal wall, and a sealing member, which inhibits the flow of gas through the opening. It is expected that the seal in this apparatus would not maintain complete insufflation of the body cavity as gas can gradually leak out through the flapvalves and seal. The valve configuracion also makes it impossible to extracorporealise an organ, which is preferred in hand-assted surgery devices. The device also has a complicated construction.

A surgical glove suitable for use in endoscopic surgical procedures is described in U.S. Pat. No. 5,526,536 (Cartmill). The glove has an inflatable wrist section, which when inflated, is said to provide a seal between the surgeon's hand and the body wall. The surgeon's gloved hand must remain in the body cavity to maintain insufflation of the body cavity. Therefore this device also restricts the actions of the surgeon.

U.S. Pat. No. 5,522,791 (Leyva), describes an abdominal retractor, which retracts an abdominal incision providing access for a hand into a body cavity. The hand is passed into a sleeve and the other end of the sleeve is mounted to the retractor.

U.S. Pat. No. 5,545,179 (Williamson) describes an access assembly, which provides access for surgical instruments to a body cavity during surgery. A sealing sleeve is inflated to form a large balloon portion with the body cavity, the balloon portion being constrained to remain within the body cavity. It is difficult to retract a surgical instrument through a balloon portion and out of the body cavity, because of frictional resistance to the movement of the surgical instrument relative to the balloon sleeve.

A method of performing laparoscopic surgery is described in U.S. Pat. No. 5,636,645 (Ou), which includes the steps of inserting a surgeon's gloved hand into a body cavity and sealing the hand to body tissue surrounding the cavity. This method restricts the actions of the surgeon because the surgeon's gloved hand must remain in the body cavity sealed to the surrounding tissue to maintain insufflation of the body cavity. The seal between the surgeon's gloved hand and the surrounding tissue must be re-established each time the gloved hand is inserted into the body cavity, if insufflation of the body cavity is to be maintained.

An apparatus and a method for carrying out minimally invasive laparoscopic surgery is also described in U.S. Pat. No. 5,640,977 (Leahy et al). A surgeon's hand is passed through a sleeve to access a body cavity, the sleeve being sealed around the surgeon's forearm.

U.S. Pat. No. 5,653,705 (de la Torre et al) discloses an envelope, which is said to provide access for an object passing into a body tissue incision, while maintaining insufflation of the body cavity. A first opening in the envelope is sealed around the body tissue incision and a second opening is sealed around an object passed into the envelope.

Devices for use during surgery which provide access to a surgical site and effect a seal independent of a surgeon's hand are also known. In general devices of this type are positioned predominantly external to a body cavity, and are complex, large and bulky. These devices prove difficult to use because they are cumbersome and/or because of their complexity. For example, a flexible, fluid-tight envelope to provide access for an object passing through a body tissue incision while maintaining insufflation pressure is described in U.S. Pat. No. 5,672,168 (de la Torre et al). This is a complex device including a first opening secured and sealed to the body tissue incision, and a second opening distal from the body tissue incision and sealed to a surgeon's forearm. The device also includes a housing containing a valve element at the body tissue incision.

An access port device for use during a surgical procedure is described in U.S. Pat. No. 5,803,921 (Bonadio). An object is passed into the device sleeve, the device is sealed around the object at the sleeve opening and the device is also sealed at the body cavity.

U.S. Pat. No. 5,741,298 (MacLeod) describes a method for performing surgery using a multi-functional access port. The access port has a sealing ring which protects the body wall incision from contamination. A sealing cap or a surgical glove is connected to the sealing ring to maintain insufflation of the body cavity. This surgical method is also restrictive because the surgeon's gloved hand must remain sealed to the sealing ring, if body cavity insufflation is to be maintained.

A surgical apparatus for use during hand assisted minimally invasive surgery is described in U.S. Pat. No. 5,813,409 (Leahy et al). A sleeve is mounted at one end to a body tissue incision. The sleeve seals to the surgeon's hand to maintain pneumpperitoneum. Surgical instruments may then be passed into the sleeve to a surgeon's hand within, which may then be inserted into the incision. This device is relatively large, requires a multistep process for installation and comes in several parts.

U.S. Pat. No. 5,906,577 (Beane et al) describes a retractor device for retracting the edges of an incision to form an opening to a body cavity. A flexible sleeve is mounted to the retractor, and an object passed through the device is sealed to maintain insufflation of the body cavity. This device also consists of many component parts that must be assembled carefully.

WO 98/35615 (Crook) describes a device for performing HALS that consists of a wound-edge retractor to which is attached a sleeve similar to others mentioned above. This device also consists of several component parts and has a complicated installation procedure.

An access port device for use during hand-assisted laparoscopic surgery is described in SP 10-108868 (Tamai, Shitomura). This device consists of a wound retractor component to which is attached an iris valve. The wound retractor component is made of two rings, an inner ring and an outer ring joined by a silastic sleeve to provide a retractive force. The device is inserted into an incision and the surgeon's hand is inserted through the device. The iris valve is then closed around the arm to effect a seal to prevent the escape of insufflation gas.

Generally known devices are difficult to use because they are cumbersome and/or because of their complexity. In addition, tight seals are often not maintained and/or the movement of a surgeons arm is restricted and/or the device may become dislodged from a wound.

There is therefore a need for a sealing device, which provides effective sealing means to seal an object passing through the device, and which is convenient and easy to use, compact and neat, and may be used repetitively with minimum delay and minimum effort.

STATEMENTS OF INVENTION

According to the invention there is provided a medical device comprising:

a sleeve of defining a lumen;
the sleeve having a twisted sleeve section defining a reduced lumen section; and
tensioning means to facilitate axial extension of the twisted sleeve section.

In a particularly preferred embodiment the sleeve is twisted to provide the twisted sleeve section. Most preferably the sleeve is of pliable material.

In a preferred embodiment the means to facilitate axial extension of the twisted sleeve section comprises a chamber for a pressuring fluid.

In this case the chamber may be defined by an outer sleeve section and an inner sleeve section.

Preferably the outer sleeve section is a substantially cylindrical sleeve section and the inner sleeve section is a twisted sleeve section of the same untwisted diameter as that of the outer sleeve section.

In a particularly preferred embodiment the sleeve is turned axially back on itself to define the outer sleeve section and the inner sleeve section.

Preferably the reduced lumen section is of a smaller size than that of an object to be received therein or passed therethrough.

In a particularly preferred embodiment on engagement of an object in the reduced lumen section and axial movement of the object relative thereto, the sleeve everts so that the twisted inner sleeve section is rolled over outwardly to become an untwisted outer sleeve section and the outer sleeve section is correspondingly rolled over inwardly to become a twisted inner sleeve section.

Preferably the chamber is fluid impermeable. Ideally the chamber is inflatable.

Preferably the chamber has an access port for inflation of the chamber.

In one particularly preferred embodiment the device includes eversion limiting means to axially limit eversion of the sleeve.

The device may have a first eversion limiting means for location externally of the opening and a second eversion limiting means for location internally of the opening.

Preferably the or each eversion limiting mean is an O-ring, preferably of a resilient material.

In one arrangement the or each eversion limiting means is housed in the chamber.

The or each eversion limiting means may be movable axially in the chamber.

In another arrangement there are two eversion limiting means and both are independently movable in the chamber.

In a further arrangement there are two eversion limiting means and a linkage means is provided between them. The linkage means may be of pliable material. Typically the linkage means comprises a linkage sleeve.

In another embodiment the eversion limiting means comprises first and second eversion limiting means attached at different locations to the sleeve.

Preferably the first eversion limiting means is attached to one end of the sleeve and the second eversion limiting means is attached at another end of the sleeve.

In a particularly preferred embodiment the eversion limiting means are movable relative to one another for twisting the sleeve. The eversion limiting means may be rotatable-relative to one another for twisting the sleeve.

In one embodiment the device includes handle means to facilitate movement of the eversion limiting means relative to one another.

Preferably the device includes locking means for locking the first eversion limiting means relative to the second eversion limiting means.

In another embodiment of the invention the tensioning means is a mechanical tensioning means.

In this case the tensioning means may comprise a spring means.

Preferably the reduced lumen section is sized to sealing engage an object passing therethrough.

In one aspect the device is for use in surgery.

The device may be a forearm seal for use in carrying out hand assisted laproscopic surgery.

Alternatively the device is an endoluminal device.

The device may be an introducer for introducing an instrument into a body through an opening.

The device may also be an exsanguinator or an envaginator.

In another aspect the device is a tissue dissector.

Alternatively the device is a trocar seal.

BRIEF DESCRIPTION OF THE DRAWINGS

The invention will be more clearly understood from the following description thereof given by way of example only with reference to the accompanying drawings, in which:—

FIG. 1 is a perspective view of a hand access device according to the invention;

FIG. 2 is a cross sectional view of the device of FIG. 1;

FIGS. 3 and 4 are a perspective view of the device being inserted into an incision in the abdominal wall;

FIGS. 5 to 7 are perspective, partially cross sectional views of a surgeons hand being inserted through the device;

FIG. 8 is a distal end view of the device with a hand in place;

FIG. 9 is a perspective, partially cross sectional view of the hand access device with a surgeons hand fully inserted;

FIG. 10 is a perspective view of the device in an intermediate position on a surgeon's arm;

FIG. 16 is a perspective view of a tube from which the device may be formed;

FIG. 17 is a view of the sleeve of FIG. 16 partially folded over;

FIG. 18 is a view of the sleeve of FIG. 17 in a twisted configuration;

FIG. 19 is a side view of the twisted sleeve;

FIGS. 20 and 21 are perspective views illustrating the insertion of an instrument through an access device of the invention;

FIGS. 34 to 39 are views of the twisting of a tube similar to FIGS. 28 to 33;

FIGS. 40 and 41 are a graphical representation of the angel of twist plotted against lumen diameter.

FIG. 42 is a perspective view of a twisted tube with an elongate object passing therethrough;

FIG. 43 is an end view of the tube of FIG. 42;

FIGS. 44 to 50 are various plan and elevational views illustrating the formation and internal pressurising of a thin walled tubed;

FIGS. 62 to 67 are various side cross sectional and end views illustrating the translation of a elongate object through a twisted tube;

FIG. 75 is a cross sectional view of another hand access device with adjustable twist;

FIG. 76 is an exploded sectional view of part of the proximal rings of the device of FIGS. 75;

FIG. 78 is an enlarged cross sectional view of a sealing mechanism between the proximal rings of FIGS. 76 and 77;

FIG. 79 is a perspective view of another hand access device of the invention;

FIG. 80 is a side, partially cross sectional view of the device of FIG. 79, in use;

FIG. 81 is an enlarged cross sectional view of a detail of the device of FIG. 80;

FIG. 82 is a cross sectional view of a sleeve used to form another hand access device of the invention;

FIG. 83 is a cross sectional view of the device formed from the sleeve of FIG. 82;

FIG. 84 is a cross sectional view of the device of FIG. 83, inflated;

FIG. 85 is an enlarged view of a detail of the device of FIG. 84;

FIGS. 95 is a perspective, partially cut-away view of a further hand access device of the invention;

FIGS. 96 is a view of the device of FIG. 95, in use;

FIG. 102 is a plan view of a device according to the invention;

FIG. 103 is an elevational view of the device of FIG. 102;

FIG. 104 is a cross sectional elevational view of the device of FIG. 102;

FIG. 105 is a perspective view of the device of FIG. 102;

FIGS. 106 to 109 are views illustrating the device of FIGS. 102 to 105 with the sleeve in an extended position;

FIG. 110 is a plan view of a device according to another aspect of the invention;

FIG. 111 is an elevational view of the device of the device of FIG. 110;

FIG. 112 is a cross sectional view of the device of FIG. 110;

FIG. 113 is a perspective view of the device of FIG. 110;

FIGS. 114 to 117 are views illustrating the device of FIGS. 110 to 113 in a compressed condition;

FIG. 126 is a cross sectional view of another device according to the invention;

FIG. 127 is a cross sectional view of the device of FIG. 126 with the sleeve inflated;

FIG. 128 is a cross sectional view of another device according to the invention; and FIG. 129 is a cross sectional view of the sealing device of FIG. 128 with the sleeve inflated and with the tubes axially extended.

DETAILED DESCRIPTION

Figures 11, 12:
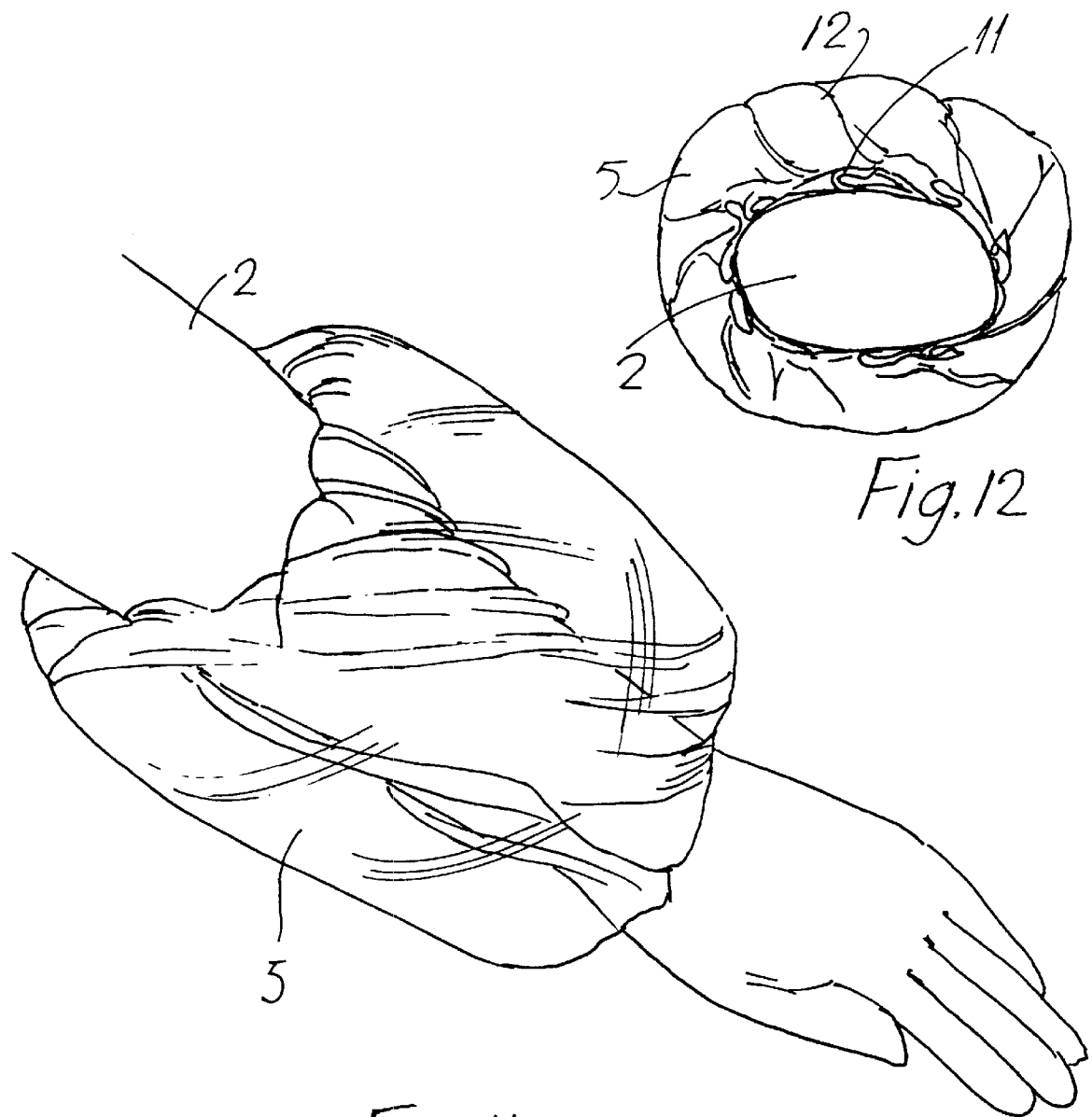
FIG. 11 is a perspective view of a hand access device in position on a surgeon's arm.
FIG. 12 is a cross sectional vie of the device of FIG. 11 showing the sealing engagement to the surgeon's arm.
Figure 13:
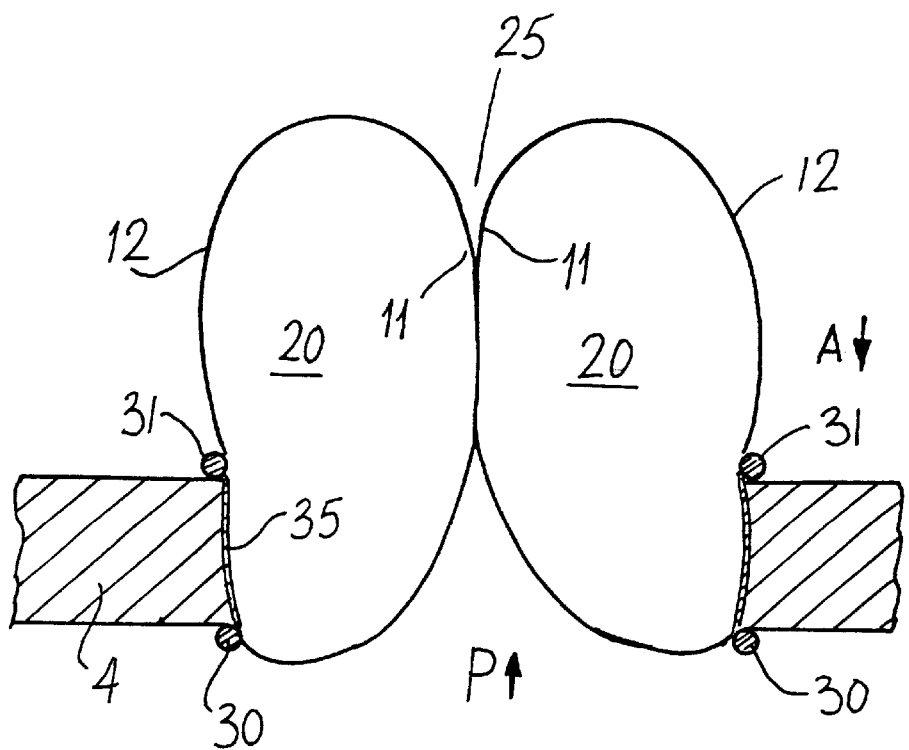
FIG. 13 is a cross sectional view of the device of FIGS. 1 to 10 in position ready to receive a surgeon's arm.
Figure 14:
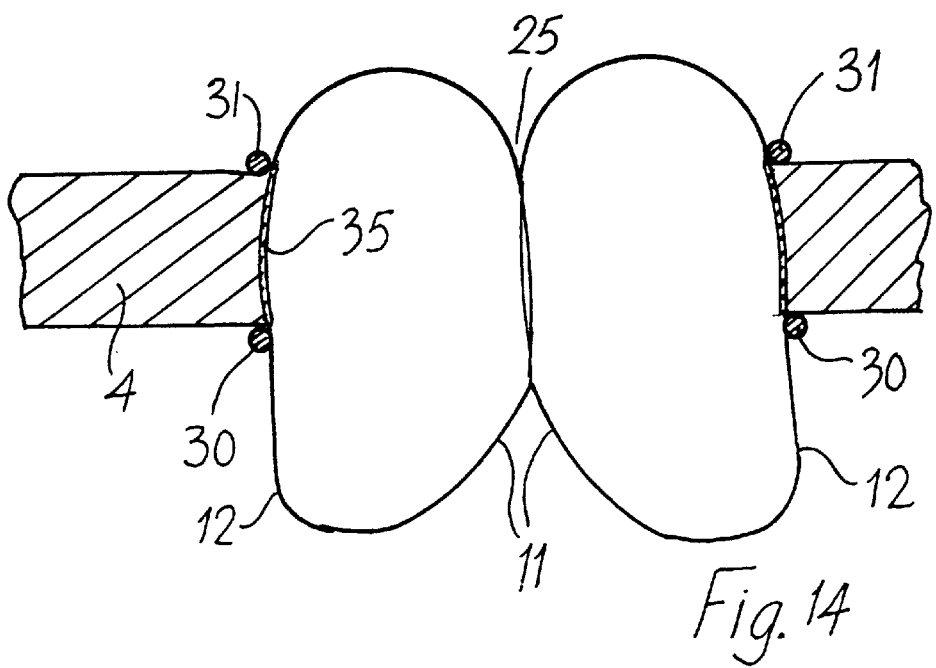
FIG. 14 is a cross sectional view similar to FIG. 13 fully inserted through an incision.
Figure 15:
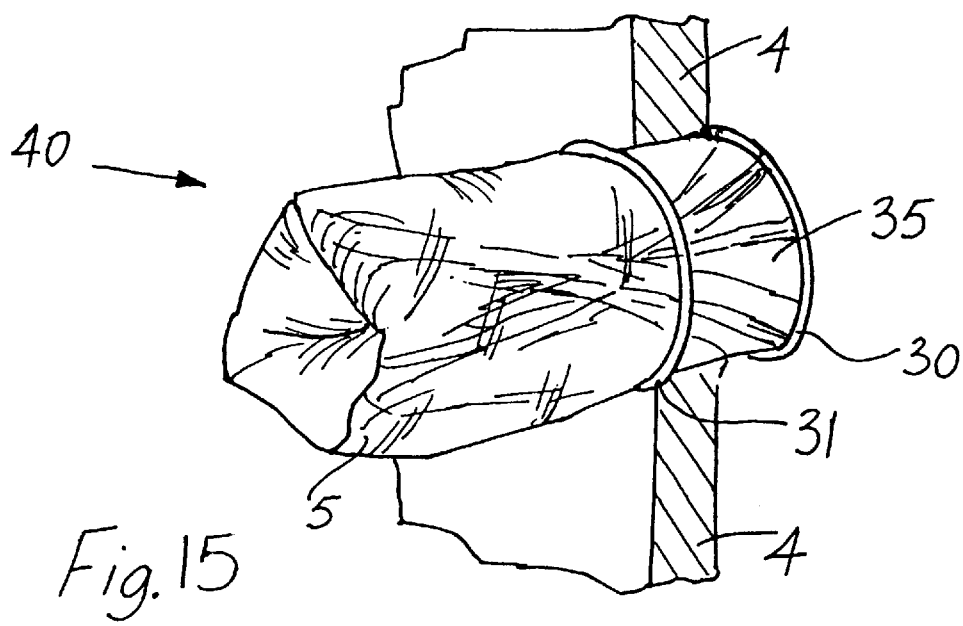
FIG. 15 illustrates an access device of the invention.
Figure 22:
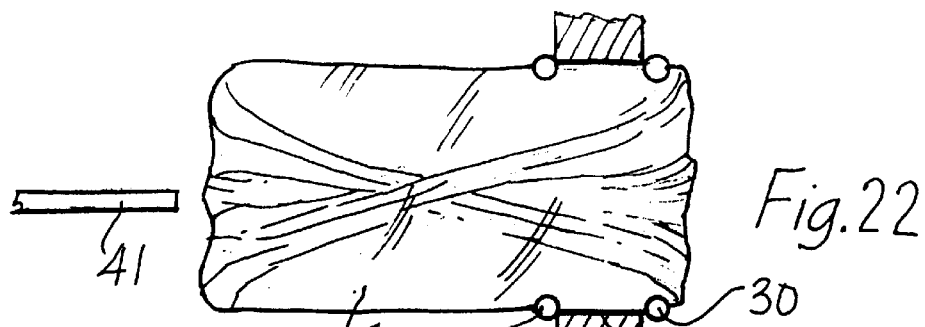
FIGS. 22 to 25 are side views of the device of FIG. 20 illustrating stages of instrument insertion through the device.
Figure 23:
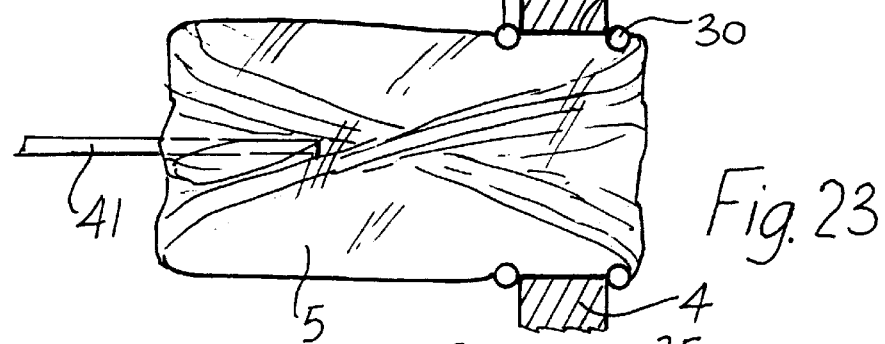
Figure 24:
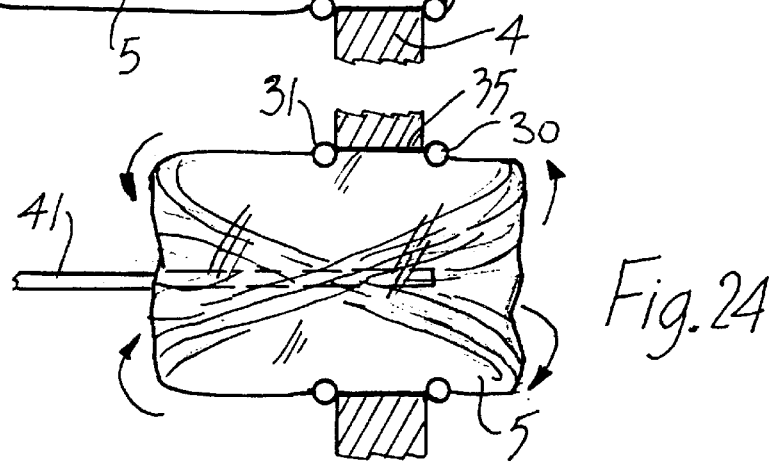
Figure 25:
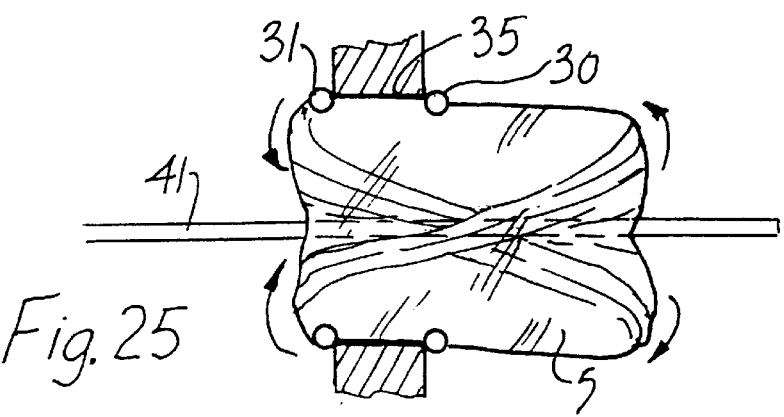
Figure 26:
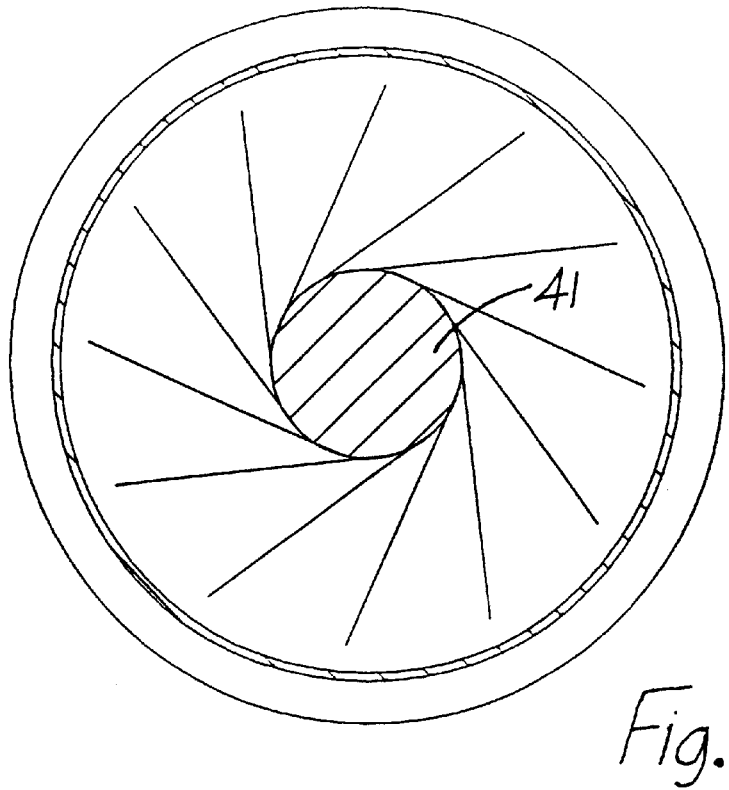
FIG. 26 is a cross sectional view of an access device with a circular cross sectional instrument in place.

In a first preferred embodiment of the invention and referring in particular to FIGS. 1 to 16 there is illustrated a hand access device 1 according to the invention which in this case, is for use as a seal for sealing a surgeon's forearm 2 on entry through a wound opening 3, for example in an abdominal wall 4.

Referring in particular to FIGS. 16 to 19 the sealing device 1 comprises a substantially tubular sleeve 5 of pliable gas tight material formed from a tube 10 such as a suitable biocompatible plastics material. The tube 10 is turned axially back on itself to define an outer sleeve section 11 and an inner sleeve section 12. The tube 10 is twisted so that the axially opposite datum indicators 15, 16 are circumferentially spaced-apart as illustrated in FIG. 18.

The inner and outer sleeve sections 11, 12, define therebetween a sealed inflatable chamber 20. The inner sleeve section 12, defines a lumen 25 and, on inflation of the chamber 20, the inner sleeve section 12 sealingly engages an object extending or passing through the lumen 25.

The hand access device includes an eversion limiting means for the sleeve 5. The eversion limiting means is in this case provided by a first O-ring 30, which is attached to the sleeve 5 and a second O-ring 31, which is attached to an axially spaced-apart location on the sleeve 5. The inner O-ring 30 is of a suitable resilient elastomeric material for bunching of the ring 30 to facilitate ease of insertion into a wound 3 as illustrated in FIGS. 3 and 4.

As a surgeon inserts his forearm 2 through the lumen 25 of the device 1, the inner sleeve section rolls 12 along with the arm 2 and in turn the outer sleeve section 11 everts. An effective seal is maintained around the surgeon's forearm 2 and the sealed integrity of the body cavity being operated upon is maintained. To facilitate insertion of the surgeon's arm 2 lubrication may be used. In this case the device 1 is pre-twisted, and may be inflated prior to or during use.

A wound protector section 35 of the sealing device between the rings 30, 31 may be of a plastics sheet material that has a greater flexibility than that of the main body of the sleeve 5. In this way, on inflation of the sleeve 5 the protector section 35 stretches to conform closely to the irregular shape of the wound 3 and provide a tight seal to the wound opening 3. In addition, the inner ring 30 is drawn against the inner wall surrounding the wound 3, on inflation of the sleeve 5. The arrangement also facilitates lubricated rotation of the protector section 35 which facilitates insertion of a surgeon's arm 33.

The inner O-ring 30 may have a larger diameter than that of the outer O-ring 31 to create a tapering effect. This arrangement promotes a pressure differential which assists insertion of a surgeon's arm 2 acting against the internal abdominal pressure.

The invention provides a device which allows laparoscopic surgeons insert their hand into the abdominal space during laparoscopic surgery and regain the tactile feedback, three dimensional perspective and general use of the hand as an operative tool as it was in open surgery. The device is easy to insert into a small incision and easy to withdraw from the same incision. The device facilitates ease of movement within the device so that the device is not a hindrance to the performance of the surgery. An effective seal is provided to both the operator's forearm and to the wound edges so as to prevent the escape of gases used to maintain the pneumoperitoneum.

In addition the device allows the removal of organ specimens from the abdominal cavity through the device for the purpose of either removing them completely from the body or for performing a surgical procedure on them while they are temporarily removed from the body or extracorporealised. It is a further object of the invention to allow the operator to remove the hand from the device and leave the device in place without compromising the pneumoperitoneum.

The device 1 consists of a double-layer polymeric sleeve 5 through which the operator can extend a hand 2 into the abdomen. The device 1 is held in place in the abdominal incision 3 by an arrangement of rings 30, 31 which may be attached to the outer layer of the sleeve 5. The rings 30, 31 provide an anchorage for the polymeric sleeve 5 when it is in the abdominal incision 3. A stopcock valve 26 and inflation bulb allow the device to be inflated through an inflation tube 27 leading into the chamber 20 when it is in position in the incision.

When the device 1 is in its correct position and is inflated the lumen 25 closes and the device seals up against the edges of the incision 3, thus preventing the escape of gas from the pneumoperitoneum to the exterior either through the device or between the device and the edges of the incision. If the operator's hand is within the sleeve 5 when it is inflated, the lumen 25 will close around the arm 2 and effect a seal such that no gas can escape from the pneumoperitoneum. The operators hand 2 need not be within the device 1 when it is inflated. The operator's hand may be inserted into the abdominal cavity through the device 1 after it has been inflated. This is possible due to the manner in which the device is constructed.

The device is assembled in such a manner so that it effectively seals around the arm 2 without constricting the arm 2 or preventing movement of the arm. Full rotational, angular and transverse movement for a surgeon's arm is allowed using the device.

The device 1 is easily inserted into the abdominal incision prior to use. The device 1 sits in the incision 3 without distortion. A hand is readily inserted through the lumen 25 of the device either in its inflated or uninflated state. The device 1 inflates quickly and effects a seal around the operator's arm 2 to facilitate creation of pneumoperitoneum.

Figure 27:
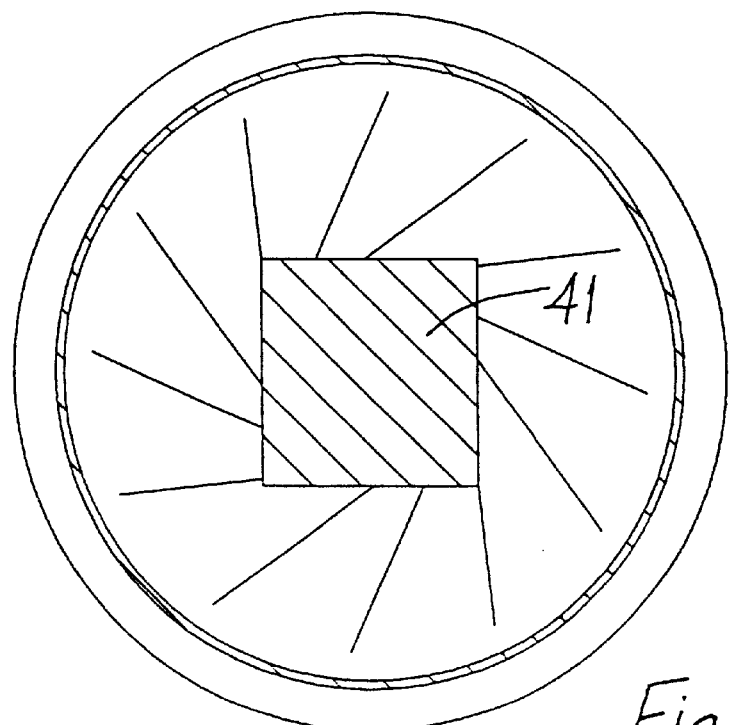
FIG. 27 is a cross sectional view of an access device with a non-circular cross sectional instrument in place.
Figure 32:
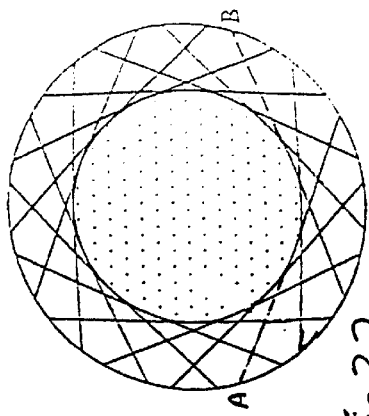
FIGS. 32 and 33 are respectively plan and elevational views of the twisted sleeve with an object extending through the lumen of the sleeve.

Referring to FIGS. 20 to 27 there is illustrated another access device 40 which is similar to that described above with reference to FIGS. 1 to 19 and like parts are assigned the same reference numerals. In his case the device 40 is used for insertion of an instrument 41. The instrument 41 may be of any suitable cross section such as circular (FIG. 26) or square (FIG. 27). The device 40 operates in exactly the same way to the device 1 as described above.

The principles which underlie this invention will be more clear from the following description with reference to FIGS. 28 to 67.

Figure 28:
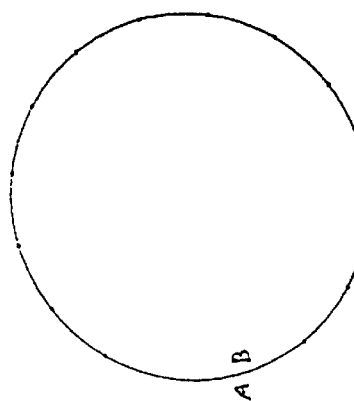
FIGS. 28 and 29 are respectively plan and elevational views of a non-twisted sleeve.
Figure 29:
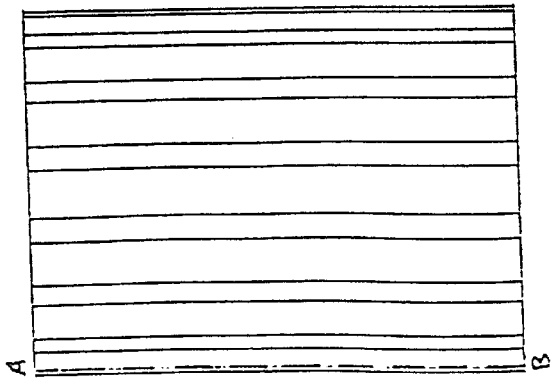
Figure 60:
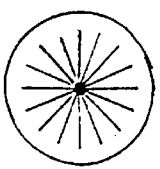
FIGS. 51 to 61 are various plan and elevational views illustrating the formation and internal pressurising of a thin walled twisted tube.
Figure 58:
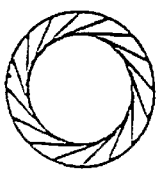
Figure 55:
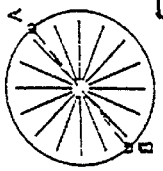
Figure 53:
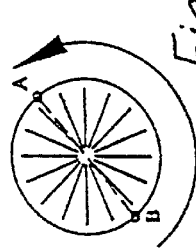
Figure 51:
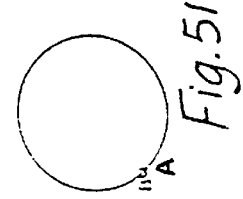
Figure 61:
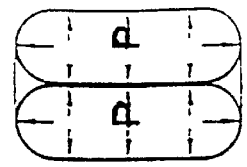

FIG. 28 depicts a thin walled tube of pliable material. It can be considered as a number of longitudinal elements, typical of which is the element A–B. Clearly there is a lumen passing through the tube, the diameter of which is the diameter of the tube. Rotation of one end of the tube relative to the other end about the axis of the tube causes the tube to twist into the configuration shown in FIG. 30.

The element A–B is now inclined to the axis of the tube but still remains a straight element. It is clear that element A–B in FIG. 30 appears longer than element A–B in 28 (it must have stretched). It follows therefore, that a force must be applied to the element to cause his elongation. In the absence of such a force elongation of the element A–B would not occur and the overall length of the tube would reduce (not depicted) in order to accommodate the change in geometry. At angles of twist less than 180° the element will not intersect the axis of the tube, its mid point being the point of closest proximity to the axis. It is the summation of all the elements at their midpoints that defines the minimum diameter of the reduced lumen formed. This diameter can be calculated knowing the original tube diameter and the angle of twist. The profile of the tube takes the form of a waisted, necked or hourglass shape. This profile is not determined by the shape of any individual element or elements but is the effect of a section in the plane of the tube axis taken through all the elements. Before proceeding to the effects of the introduction of an object into the reduced lumen particular notice should be taken of the elements as they appear in the plan view FIG. 29. All the elements are straight.

Clearly, if an object of smaller diameter than the reduced lumen were introduced into the reduced lumen the object could pass through with out making contact with the wall of the reduced lumen. It would therefore not be possible for the tube to grip or create a seal to the object. In order to accommodate the introduction of an object of larger size (diameter) it is necessary that each element deform or bend outward thus forming an increased lumen. This can be seen clearly in FIG. 32.

Figure 33:
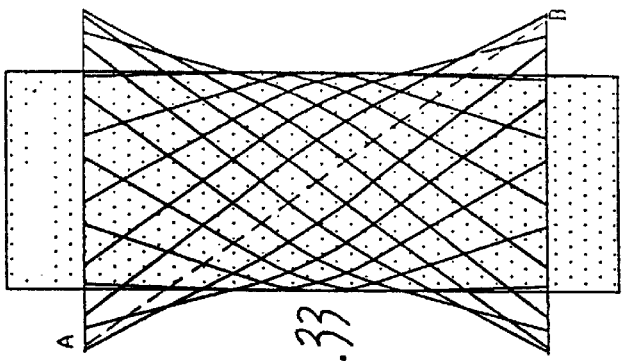
Figure 30:
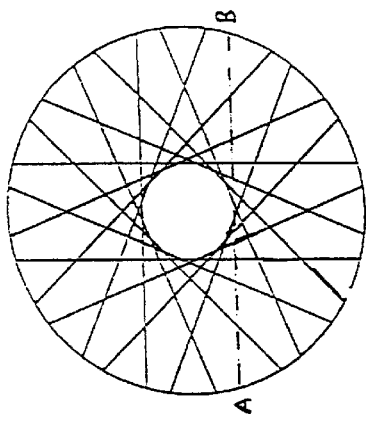
FIGS. 30 and 31 are respectively plan and elevational views of a twisted sleeve.
Figure 31:
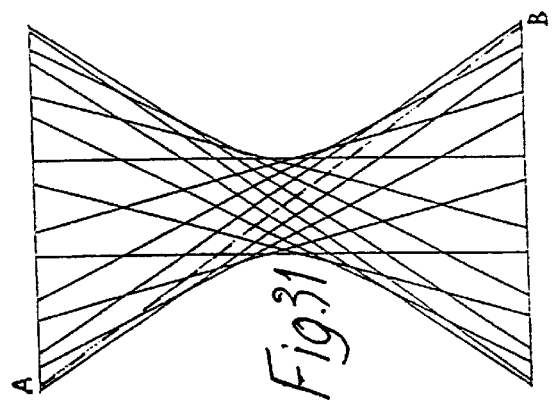

All the elements are now deformed. As before there is an apparent increase in the length of the elements. Also as before, in the absence of a force to elongate the elements the overall length of the tube will reduce to accommodate the change in geometry (FIG. 33). So it will be understood that the lumen has increased to accommodate the introduced object with out stretching the material of the tube and that the tube is intimate contact with the introduced object over at least part of its length.

The application of an axial force to the tube will cause the now deformed elements to try to straighten. Because the elements of the tube do not lie in the plane of the applied axial force there will be a corresponding radially inward force. This tendency toward straightening of the elements will be restricted by the presence of an object in the lumen. Therefore the radially inward component of the applied force will act on the inserted object creating a pressure or gripping force between the tube and the inserted object.

Referring to FIGS. 34 to 39 consider the hollow cylindrical tube shown in FIG. 35. The wall of the cylinder defines a lumen through its centre. Consider a linear element A–B. If the upper edge of the tube is rotated through some angle, point A will move to the position shown in FIGS. 36 and 37. The element A–B will still define a straight line. The tube will distort into a nominally hour glass shape with a reduced lumen at mid height. The diameter of the lumen at the neck of the tube is dependant on the angle of twist. When the upper edge is rotated through 180° the lumen will close down to zero diameter. At any horizontal plane through a twisted tube the material must be wrinkled and hence under compressive hoop stress. If the height of the tube remains unaltered then the element A–B is a twisted tube, being longer than in a plain tube, must be under tensile axial stress. If the tube is free of axial constraint the overall length of the tube will reduce.

Angle of Twist Vs. Lumen Diameter

FIG. 41 shows the lumen diameter (D2) as a proportion of the tube diameter (D1) for angles of twist (E) from 0° to 180°. The lumen diameter (D2) is calculated from:

$$D2=D1\cos(E/2).$$

As can be seen, the lumen diameter is independent of the tube length.

Elongate Object Passed Through Twisted Tube

As can be seen from FIGS. 41, 42 and 43 the angle of twist necessary to collapse the lumen of a tube to the diameter of an elongate object passed therethrough is dependant on the ratio of the tube diameter to the diameter of the elongate object. The angle of twist can be calculated from:

$$E=2\{\cos^{-1}(D2/D1)\}$$

where E is the angle of twist,

D1 is the tube diameter, and

D2 is the diameter of the elongate object.

Although depicted as of circular profile, a tube of sufficiently compliant material will conform to many non recursive profiles. For such a profile D2 is taken as the smallest diameter which can be inscribed within the profile.

Twin Walled Pressure Vessel Under Internal Pressure

Referring to FIGS. 44 to 50 consider a thin walled tube as shown in FIG. 45a. One end of the tube is folded back on itself as shown in FIG. 47 and the free ends conjoined. What is defined is essentially a twin wailed tube (or two coaxial tubes conjoined at their ends) with an enclosed volume between the two walls. One way of extending the thin walled tube in an axial direction is to introduce a pressurised fluid into the enclosed volume. This causes the outer tube to be subject to tensile axial stress and tensile hoop stress. The inner tube will be subject to tensile axial stress and compressive hoop stress. As a result the diameter of the lumen reduces and the lumen collapses into a nominally duck bill configuration but constrained by the outer tube, FIG. 50.

Figure 59:
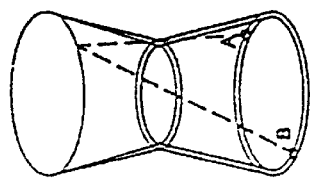
Figure 57:
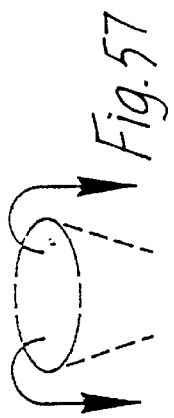
Figures 54, 56:
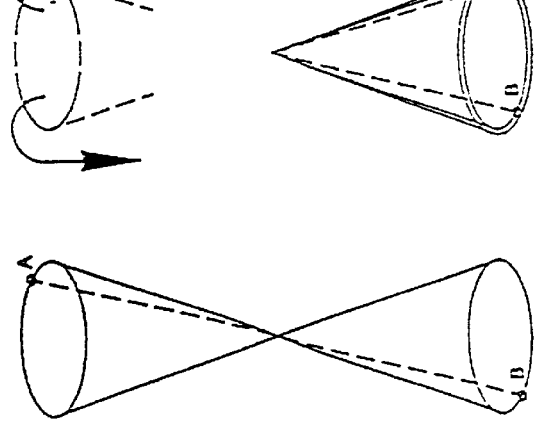
Figure 52:
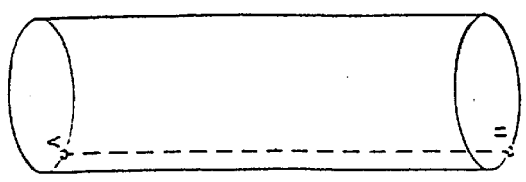

Greater control of the lumen can be obtained by the introduction of a twist into the tube. The tube shown in FIG. 52 is twisted as shown in FIG. 54. One end of the tube is folded back on itself, as shown in FIG. 56, and the free ends conjoined. This configuration defines two coaxial conical vessels conjoined at their bases and at a common apex. However the common apex is not constrained to remain in this configuration. In reality, the inner and outer tubes are free to behave as individual tubes each with half of the original twist and as such the composite tube can better be defined as two coaxial hour glass tubes as shown in FIG. 59, each containing half the original total twist. As both the inner and outer tubes are necked they each are subject to compressive hoop stresses.

Next a pressurised fluid is introduced into the enclosed volume. The introduction of the pressurised fluid extends the inner and outer tubes in an axial direction, reducing the lumen diameter. The outer tube is a necked hour glass tube with compressive hoop stresses. The introduction of the pressurised fluid also induces tensile hoop stresses, negating the compressive hoop stresses induced by the twist. Since, to remain in its twisted configuration, the tube must have compressive hoop stresses and since the pressurised fluid overcomes these compressive stresses the tube untwists and takes on a nominally cylindrical configuration, FIG. 61. Since the inner and outer tubes are conjoined, as the outer tube untwists the inner tube twists more in response. Since the outer tube now has no twist the inner tube must have all the twist. If the original total twist were 180° then the lumen would close totally. Additionally, the material defining the inner tube will be central within the diameter of the outer tube. This configuration will for brevity be called a Cyclops.

Translation of an Elongate Object through a Cyclops

Consider the arrangement depicted in FIG. 62. A shaft is passed through a Cyclops with the lumen in mutual contact with the shaft. The outer tube of the Cyclops is resting in mutual contact with a fixed surface. Consider points of contact A, between the Cyclops and the fixed surface, and B, between the shaft and the lumen of the Cyclops. As the shaft is translated, as shown in FIG. 64, point A remains fixed whilst the leading end of the lumen rolls out. Since the Cyclops does not change in overall length the trailing end of the outer tube rolls in as depicted. It will be apparent that the shaft translates to the right twice as far as the Cyclops. This is exactly the motion of a caterpillar track. From his point of view a Cyclops could be considered as a three dimensional caterpillar track. Since points A and B on the Cyclops do not move relative to their corresponding positions on the shaft and the fixed surface there is no frictional resistance to the translation of the shaft In FIG. 66, the Cyclops has translated to the right by approximately its own length. The material which had originally formed the inner tube has rolled out to become the outer tube and vice versa. In other words the Cyclops has turned inside out. Since the inner tube of the Cyclops is in a twisted configuration and since the point B remains in contact with the same point the shaft rotates about it's axis as depicted by arrow C (in this instance approx. 120°). In order to obtain this translation the resistance required to be overcome is that generated as the leading and trailing ends of the Cyclops deform as they roll out and roll in respectively.

Figures 68, 69:
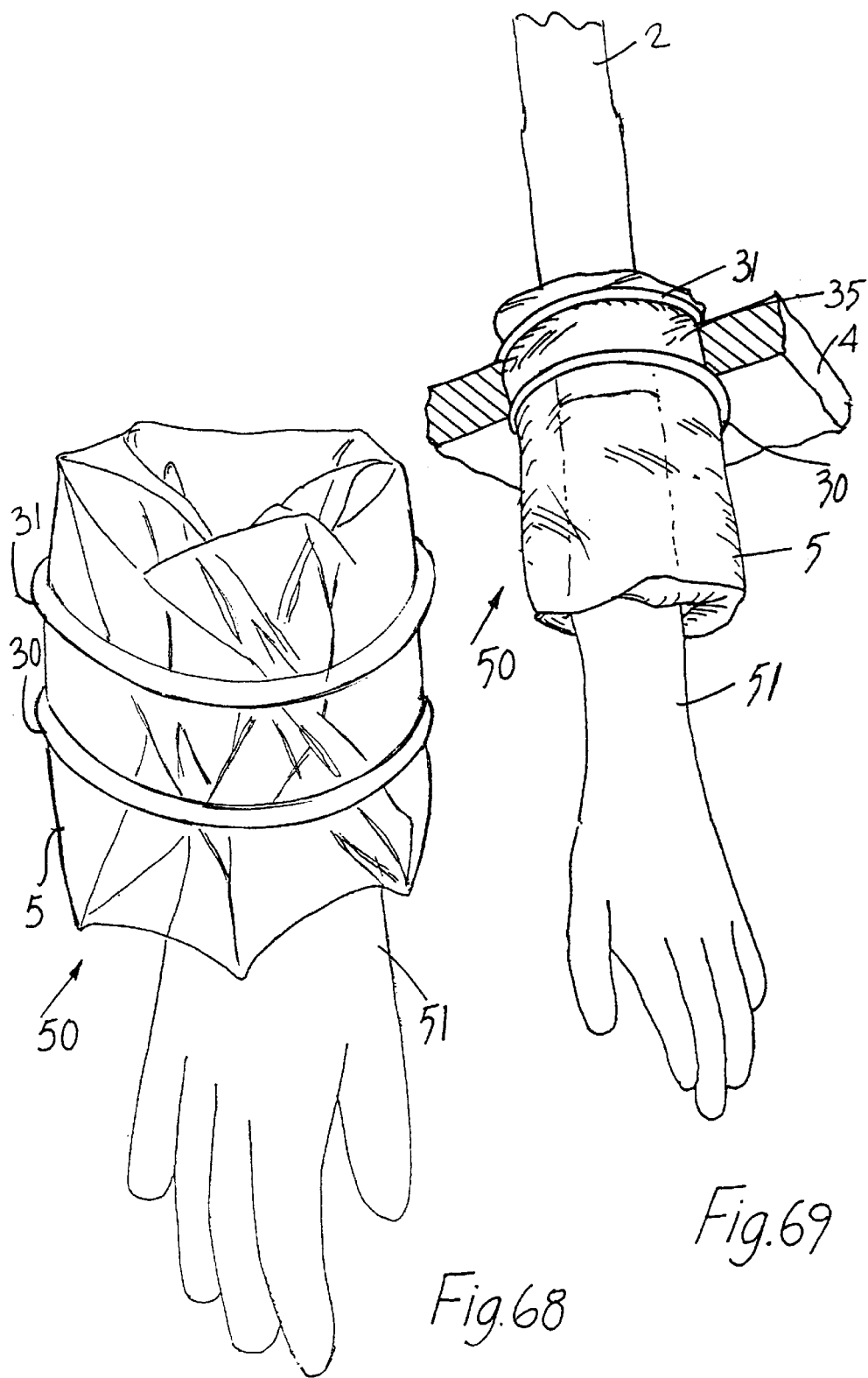
FIG. 68 is a perspective view of a hand access device with an integral glove.
FIG. 69 is a perspective view of the gloved hand access device of FIG. 68, in place.
Figure 70:
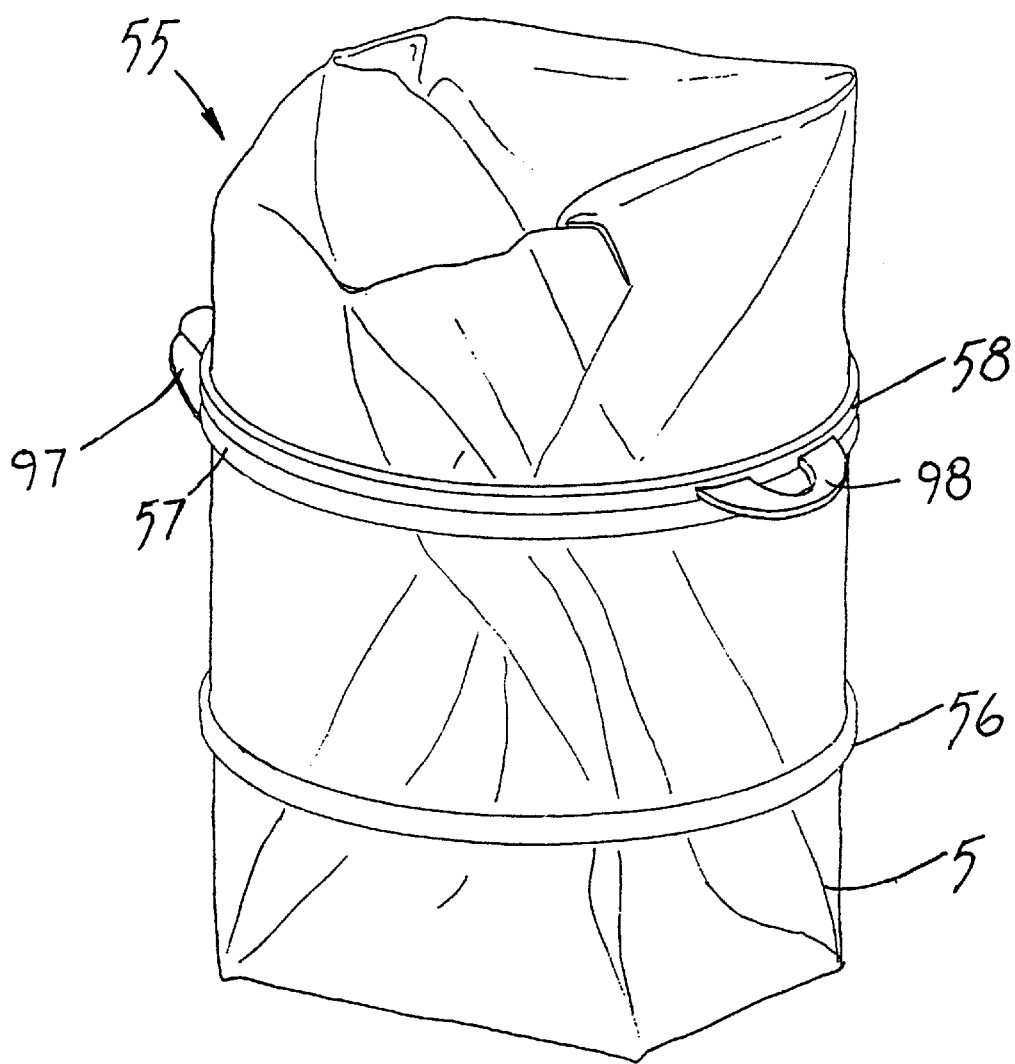
FIG. 70 is a perspective view of another hand access device with adjustable twist.
Figure 71:
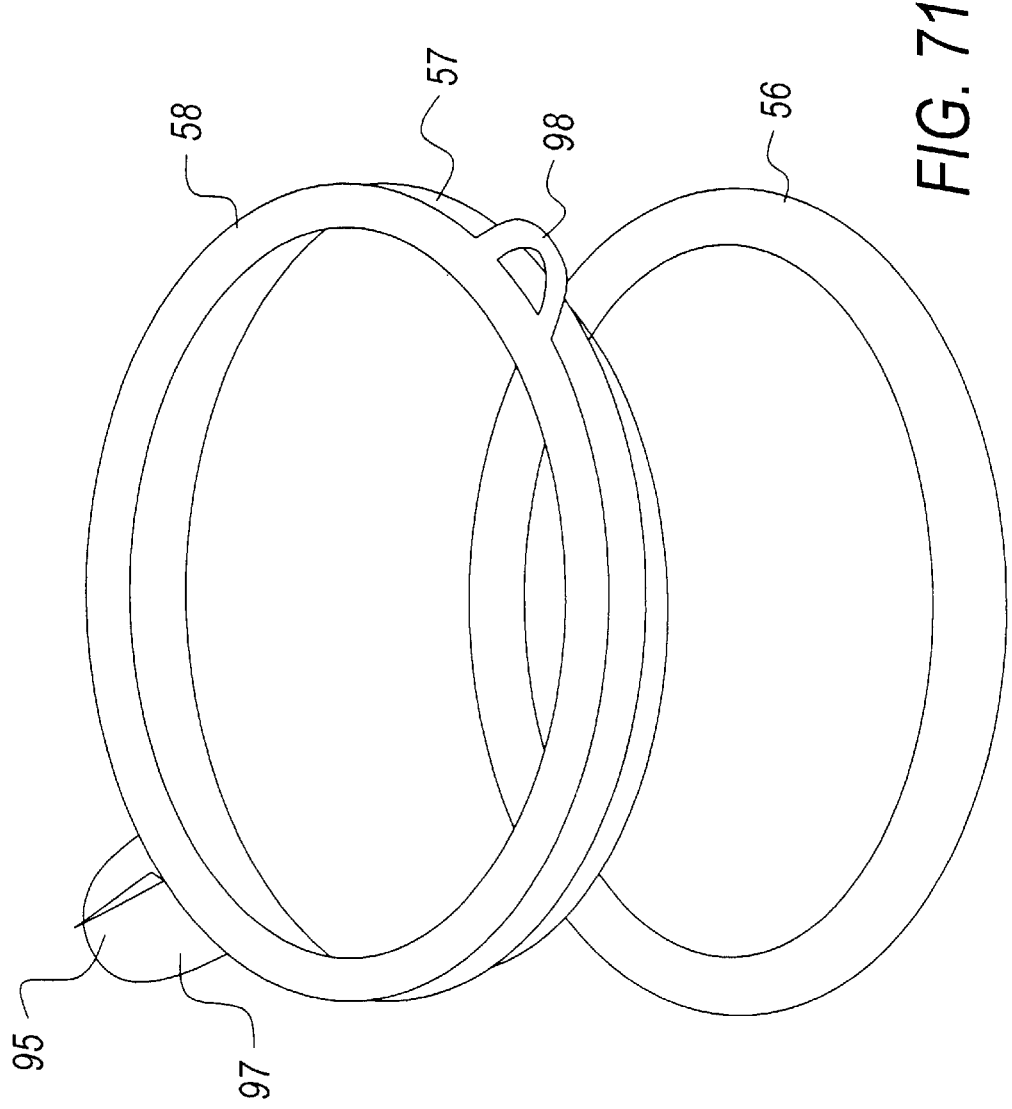
FIG. 71 is a perspective view of ring's used in the access device of FIG. 70.
Figure 72:
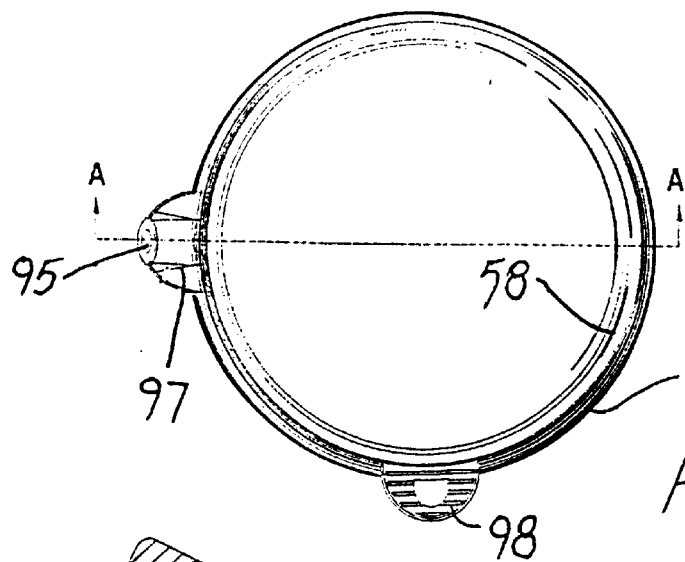
FIG. 72 is a plan view of the rings of FIG. 71.
Figure 73:
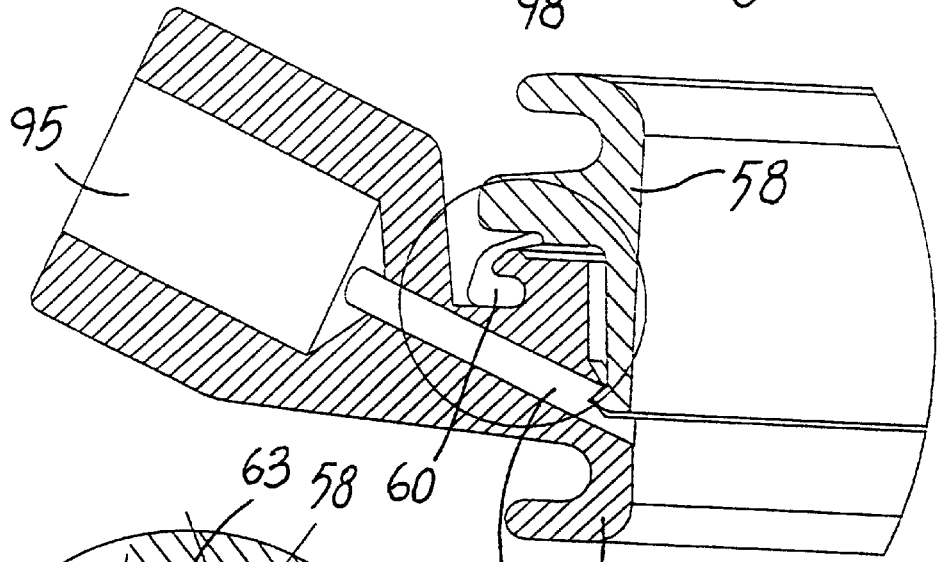
FIG. 73 is a cross sectional view of a detail of proximal rings of the device of FIG. 71.
Figure 74:
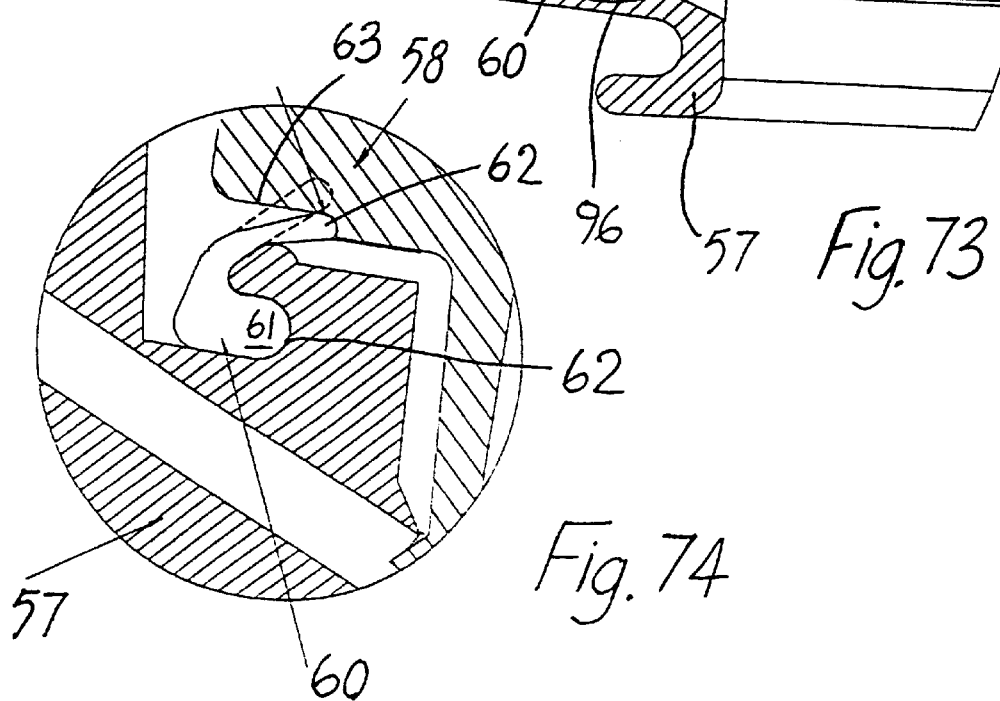
FIG. 74 is a perspective view of a detail of a seal between the proximal rings of FIG. 73.

Referring to FIGS. 68 and 69 there is illustrated another access device 50 which in this case has a glove 51 integral with or attached thereto to receive a surgeons hand.

Referring to FIGS. 70 to 74 there is illustrated another hand access device 55 according to the invention. The device 55 is similar to those described above except that in this case the twist is adjustable in situ. In this case the sleeve 5 has an inner ring 56 similar to the ring 30 and an outer ring assembly comprising two interengagable rings 57, 58 which are rotatable relative to one another to adjust the twist in the sleeve 5. The rings 57, 58 are snap fitted together and a seal 60 is used to present air egress. The seal 60 has a head part 61 which is housed in a female recess 62 in the ring 57 and a sealing part 62 which extends to sealingly to engage a projecting part 63 of the outer ring 58.

Referring to FIGS. 75 and 78 there is illustrated another adjustable twist device 70 which is similar to the device 55 of FIGS. 70 to 74 and like parts are assigned the same reference numerals. In this case snap projections 79, 80 engage on assembly of the mounting rings 57, 58. To ensure gas tight sealing between the rings 57, 58 an elastomeric sealing ring 81 is provided. The sealing ring 81 is housed in a recess in the male part 82 of the outer mounting ring 59 and projects into the space between the two rings 57, 58, on assembly to engage against an integral projection 92 of the lower ring 58. Mounting ring seals 93, 94 are used for mounting the sleeve 5 to the outer and inner mounting rings 57, 58, respectively.

In each of the devices 55, 70 the mounting ring 57 includes a side port 95 having a passageway 96 for entry of an inflation gas into the sleeve 5. The mounting rings 57, 58 are rotatable relative to one another to twist the sleeve 5 and so reduce the diameter of the lumen 25 defined by the sleeve 5. The relative rotation is effected by gripping opposed handles 97, 98 on the mounting rinas 57, 58 and turning them. This causes the sleeve S to twist from a configuration 28 where there is no twist to, for example, a 90° twist or a 180° twist in which the lumen 25 is closed. The sleeve 5 may therefore be pre-twisted or twisted during a surgical procedure.

In use, the sleeve 5 is untwisted and the O-ring 56 is inserted through a wound opening 3. A surgeon then inserts his hand through the sleeve 5. The rings 57, 58 are relatively rotated to twist the sleeve 5 and so reduce the lumen diameter. The sleeve 5 is then inflated by introducing pressurised gas through the entry port 95. This causes the sleeve 5 to extend in the axial direction, and the diameter of the lumen 25 to reduce, further enhancing the seal. The surgical procedure is then carried out. On completion of the surgical procedure, a combination of deflation and/or untwisting of the sleeve 5 is used to allow a surgeon to remove his hand. In this way, if required, the gas seal may be maintained as a surgeon removes his hand and when the hand is fully removed.

One advantage of his sealing device is that it is adjustable on site and in situ to suit a particular patient, surgeon and/or procedure. The mounting rings 57, 58 slide over one another as they rotate relative to one another. It is desirable to have a small frictional force acting between the surfaces as they rotate relative to one another to facilitate ease of operation of the device 55, 70 and also to maintain the desired sealing contact between the two rings 57, 58.

Referring to FIGS. 79 to 81 there is illustrated another surgical device 100 according to the invention. In this case an inner ring 101 has engagement means in the form of a radially and axially extending lip seal 105 to engage an inner wall of a patient at the wound opening. This facilitates positive location and engagement of the device 100, in use.

Referring to FIGS. 82 to 85, there is illustrated another device 109. In this case an inner liner or bladder 110, extending between the outer and inner rings 111, 112 is provided to ensure that the inflated sleeve 5 interior is maintained sealed while the rings 111, 112 are rotated relative to one another.

Figure 86:
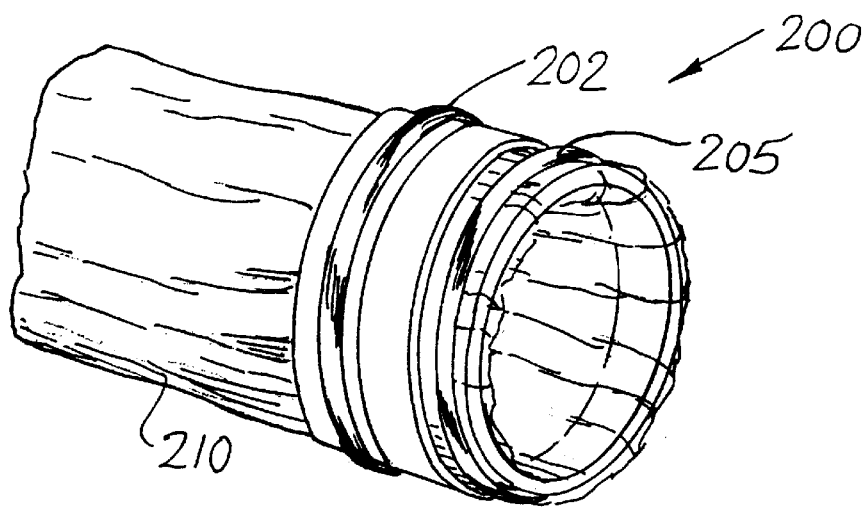
FIG. 86 is a perspective view of another device of the invention.
Figure 87:
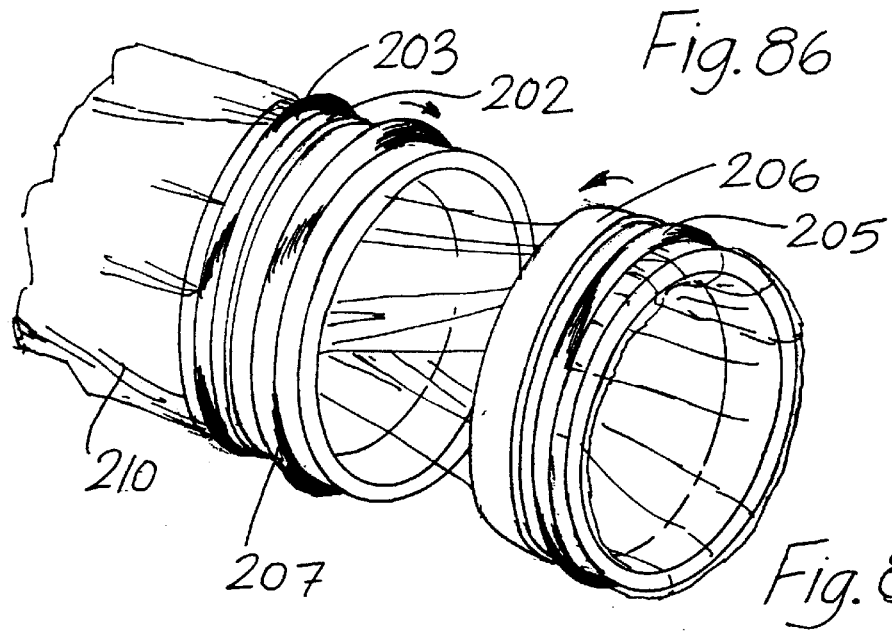
FIG. 87 is a perspective view of the device of FIG. 86 being adjusted.
Figure 88:
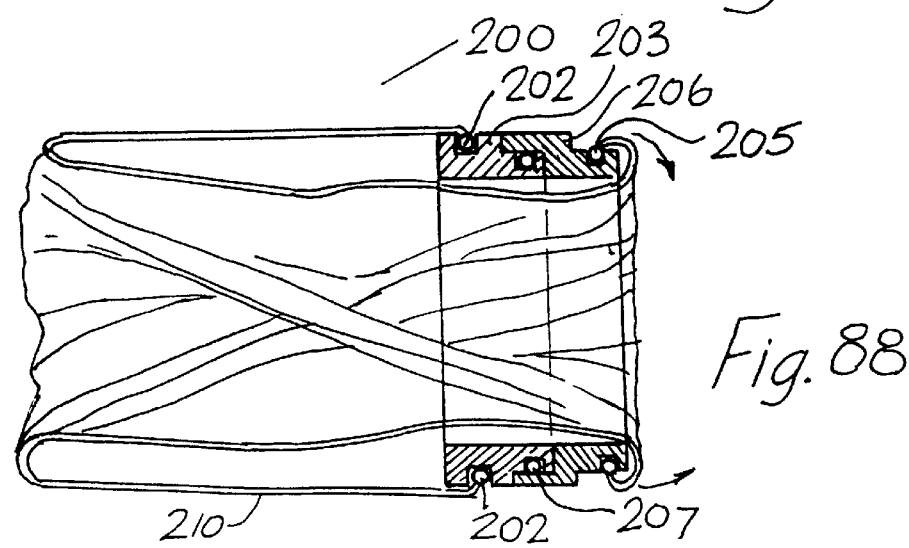
FIG. 88 is a side, partially cross sectional view of the device of FIGS. 86 and 87.

Referring to FIGS. 86 to 88 there is illustrated another surgical device 20 according to the invention. The device 1 comprises a first O-ring 201, a first outer mounting means in the form of a O-ring 202 mounted in a first receiver 203, and a second mounting means in the form of a O-ring 205 mounted in a second receiver 206. The receivers 203, 206 are in this case interconnectable as illustrated and a fourth O-ring 207 is provided between the receivers 203, 206 on assembly.

A sleeve 210 of flexible pliable plastics material extends from the second outer receiver 206 to the first outer receiver 203. The receivers 203, 206 are de-mountable as illustrated in FIG. 87 to facilitate relative rotation therebetween in the direction of the arrows to vary the degree of twist in the sleeve 210.

Figure 89:
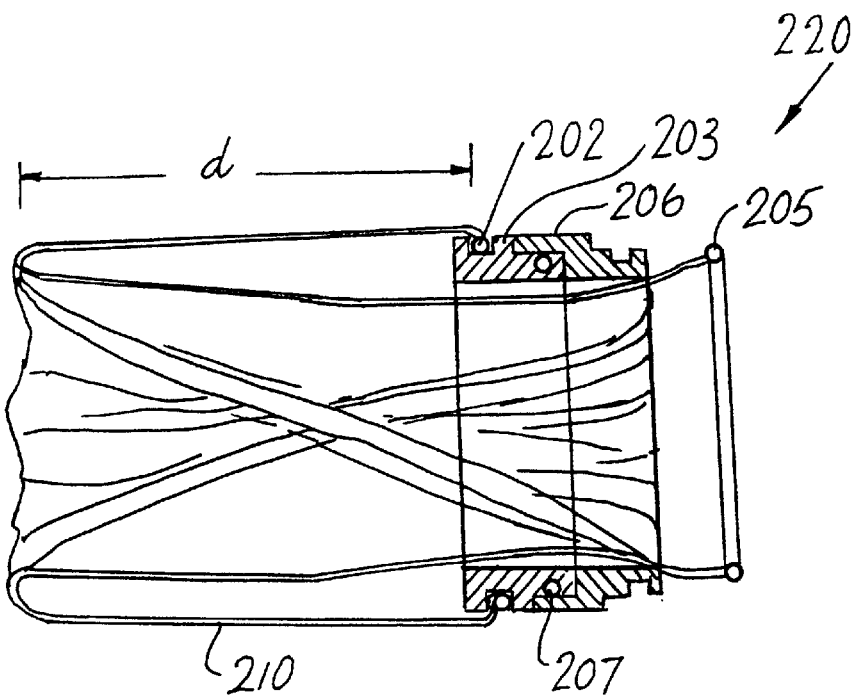
FIG. 89 is a view similar to FIG. 88 of the device partially disassembled.
Figure 90:
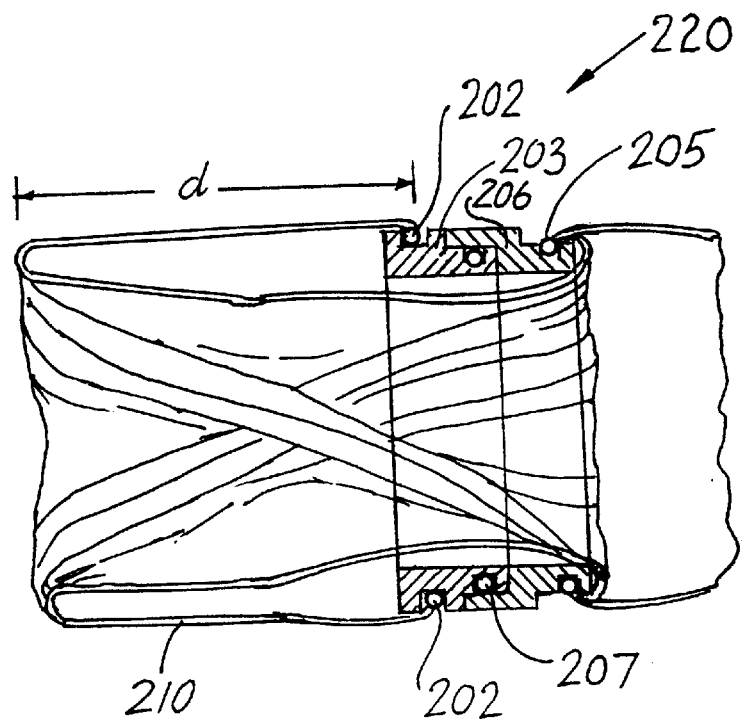
FIG. 90 is a view similar to FIG. 88 with the device of FIG. 89 re-assembled.

Referring to FIGS. 89 and 90 there is illustrated another surgical device 220 which is similar to the device 200. In his case the O-ring 205 is de-mountable from the receiver 206 to facilitate length adjustment of the sleeve 210. On removal of the O-ring 205 the sleeve 210 is adjusted to a desired length d. In this way a single device 220 may be used for a variety of thickness of abdomens. The lumen diameter defined by the twist does not need to be changed to cater for a range of abdomen sizes. The excess sleeve may be cut off or wound around the O-ring seal 205.

Figure 91:
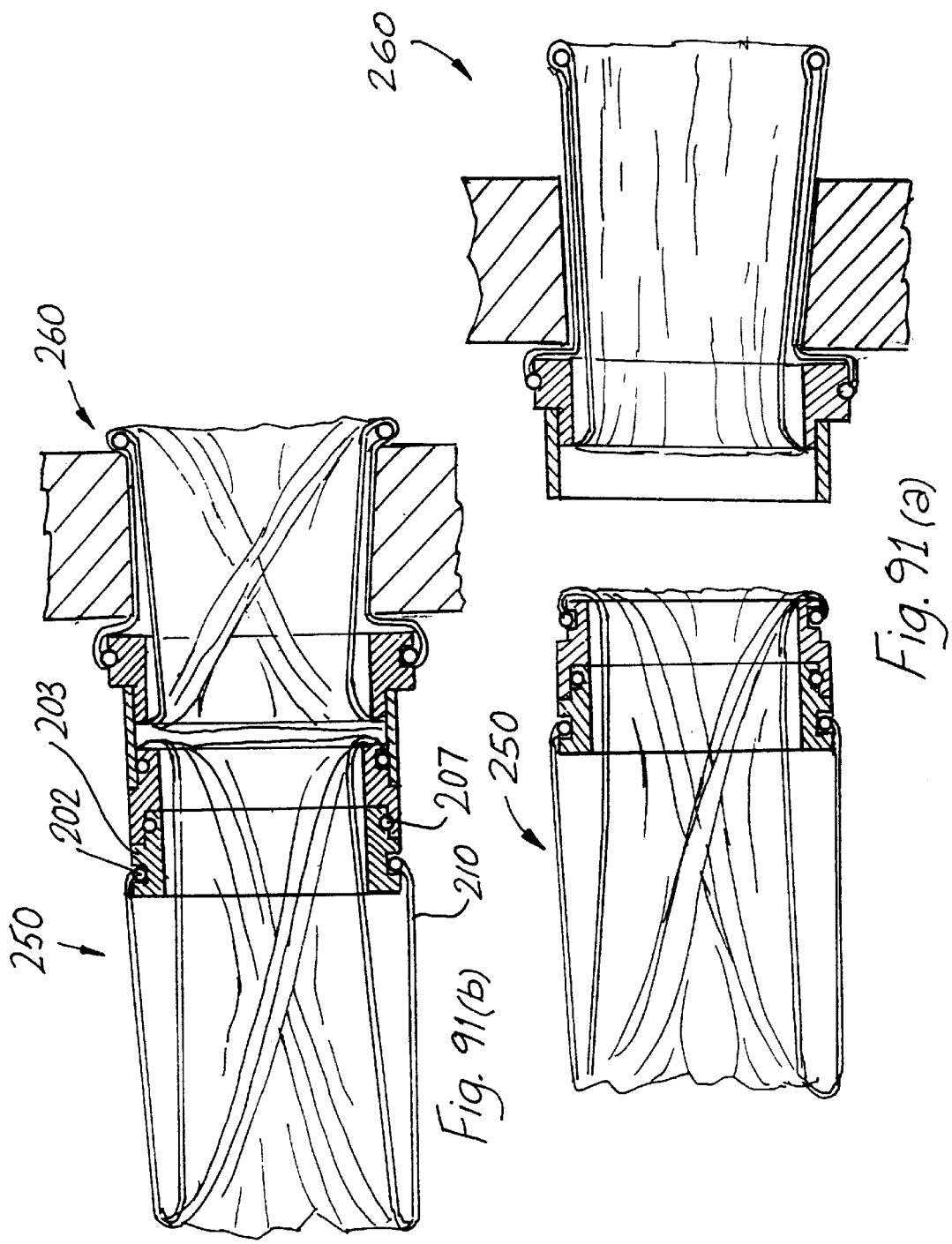
FIGS. 91$a$ and 91$b$ are cross sectional views of two devices.

Referring to FIGS. 91a and 91b there is illustrated an assembly of two surgical devices 250, 260. The device 250 is a forearm seal and the device 260 is a wound protector retractor which is assembled to an outer sealing device 250. The sealing device 250 provides an outer sealed access port through which a surgeon may insert his forearm or for insertion of an instrument or the like.

Figure 92:
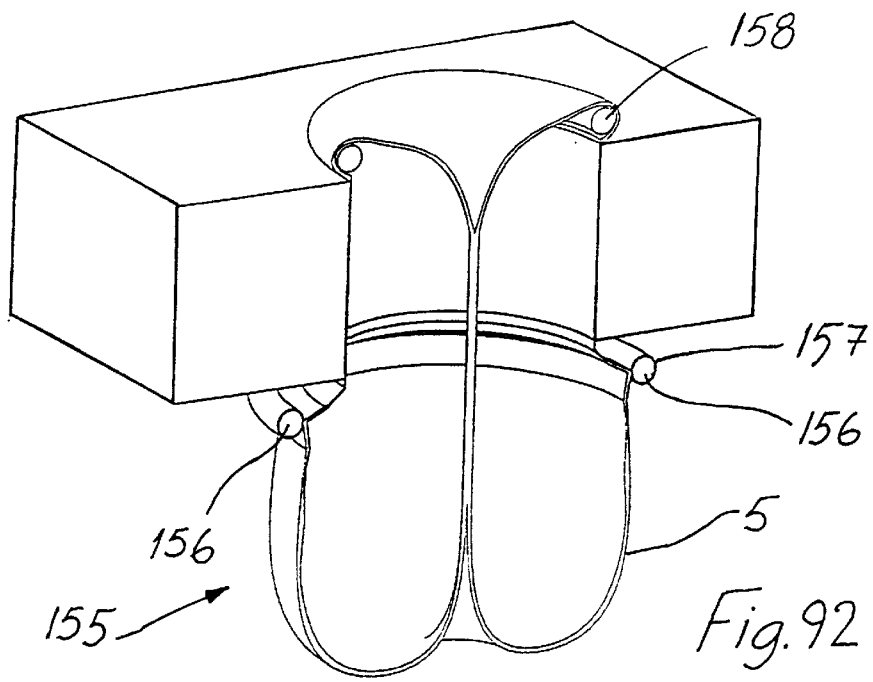
FIG. 92 is a prospective, partially cut-away view of a further hand access device of the invention.

Referring to FIG. 92 there is illustrated a modified hand access device 55 according to the invention. In this case an inner ring 56 is enclosed in a pocket 57 on the sleeve 5 while an outer ring 58 is free to move between the walls of the sleeve.

Figures 93, 94:
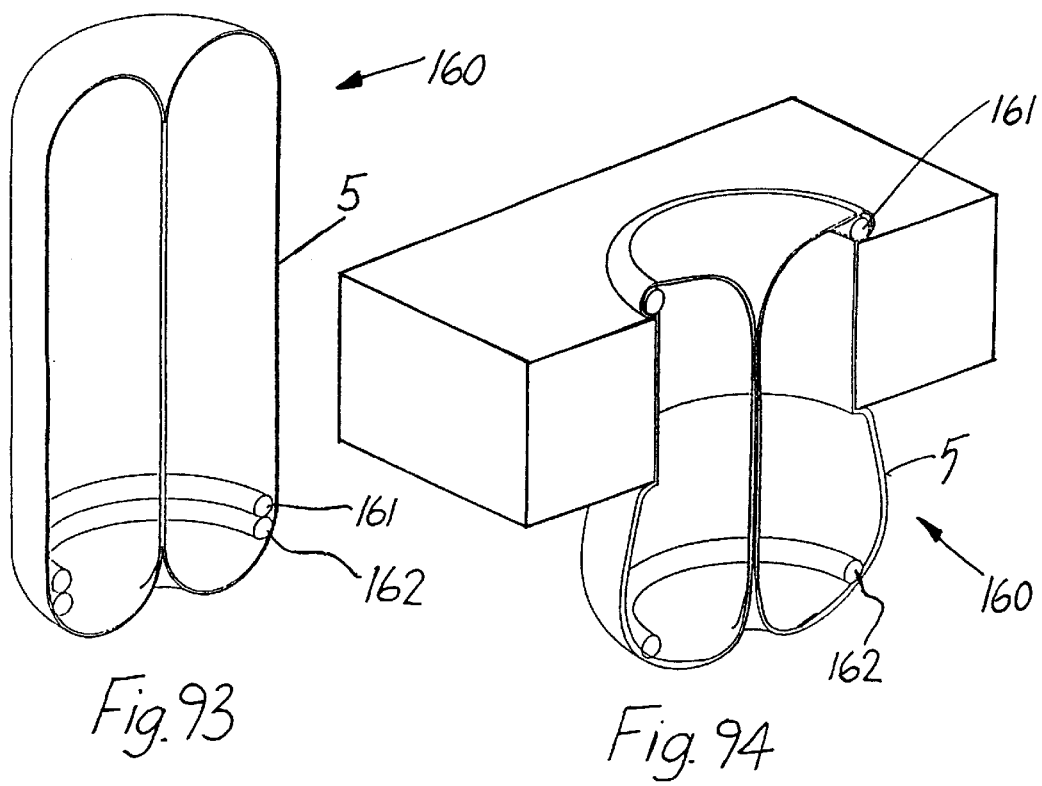
FIG. 93 is a perspective, partially cut-away view of another hand access device of the invention.
FIG. 94 is a view of the device of FIG. 93, in use.

Referring to FIGS. 93 and 94 there is illustrated another hand access device 160 in which eversion limiting rings 61, 62 are free to move axially inside the sleeve 5. The device is used as described above, the outer ring 61 engaging the outside of the abdominal wall on insertion to limit eversion into the incision. The inner ring 162 is free between the walls of the sleeve 5 when the sleeve is fully everted into the wound as illustrated in FIG. 94. On withdrawal of a surgeons arm eversion the sleeve outwardly is limited by engagement of the ring 162 against the inside of the abdominal wall. One advantage of this arrangement is that the same device may be used for a wide range of different thicknesses of abdomen.

Referring to FIGS. 95 and 96 there is illustrated another hand access device 165 which is again similar to those descried above. In this case inner and outer rings 166, 167 are not attached to the sleeve 5, however a linking section 168 of pliable material extends between the rings 166, 167.

Figure 98:
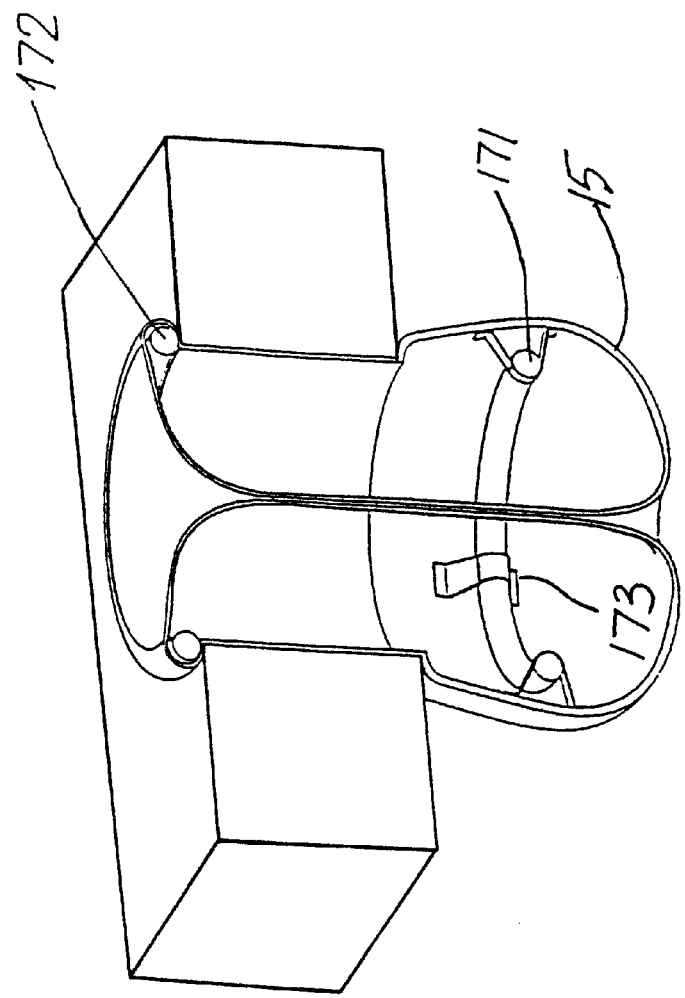
FIG. 98 is a view of the device of FIG. 97, in use.
Figure 97:
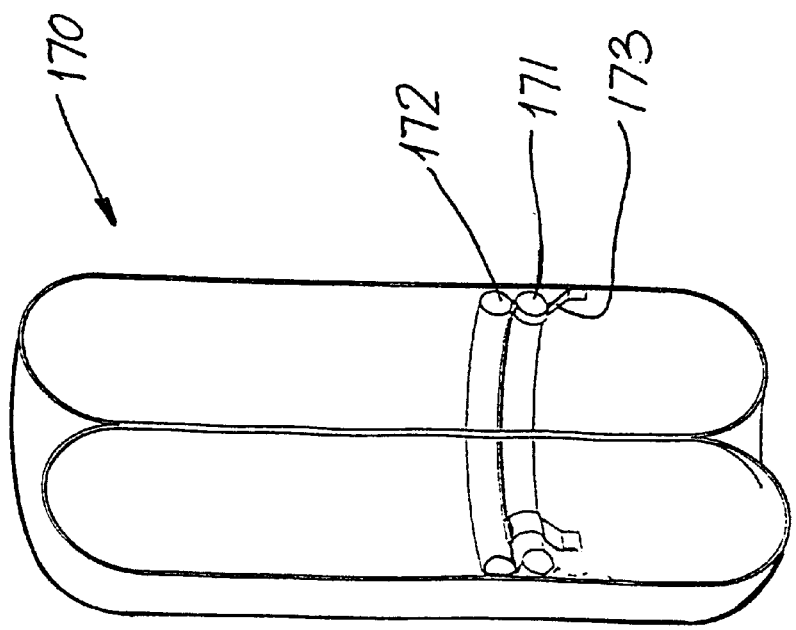
FIG. 97 is a perspective, partially cut-away view of a still further hand access device of the invention.

Referring now to FIGS. 97 and 98 there is illustrated another hand access device 70 according to the invention. In this case an inner ring 71 is held in a desired axial position in the sleeve 5 by adhesive tapes 73. An outer ring 72 is free to move axially within the sleeve.

Figure 99E:
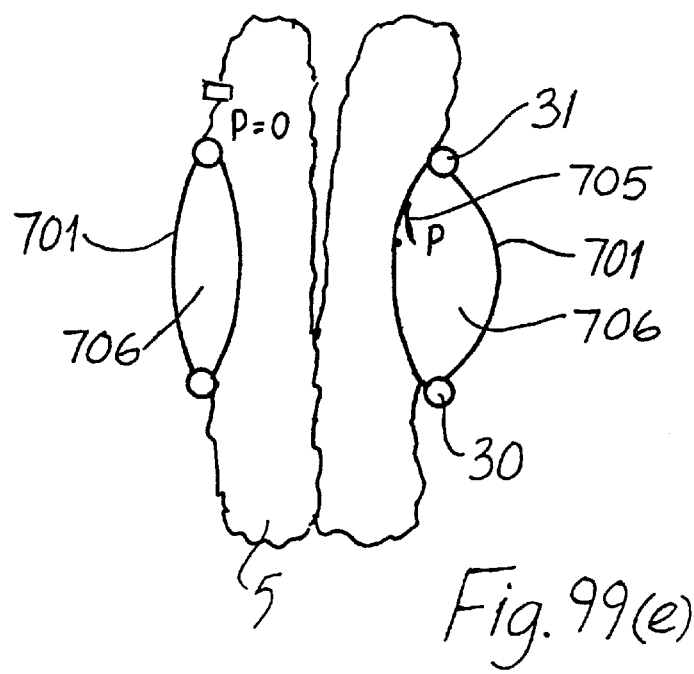
FIGS. 99($a$) through 99($e$) illustrate various views of a device in accordance with the invention.

Referring to FIG. 99 there is illustrated another medical device 700 according to the invention which is similar to those described above and like parts are assigned the same reference numerals. The device includes a shielding device to shield the existing connection between the rings 30, 31. The shield shields the sleeve section that engages with the incision from the axial tensile force. This facilitates improved conformity to the incision margins and enhanced retraction and sealing.

In this case the shield is in the form of a film 701 which is of lighter gauge than that of the main sleeve 5. There is a hole 702 in the main sleeve 5 which allows air access to the chamber 706 between the main sleeve 5 and the film 701. The hole 702 may be covered by a valve such as a non return flap valve 705.

The shielding film 701 is illustrated as deflated in FIG. 99a. After inflation it bulges outwardly as illustrated in FIG. 99b and a better conformity to the incision is achieved as illustrated in FIG. 99c.

This arrangement may then be used to allow deflation of the inner sleeve for improved access as illustrated in FIG. 99d.

Figures 100, 101:
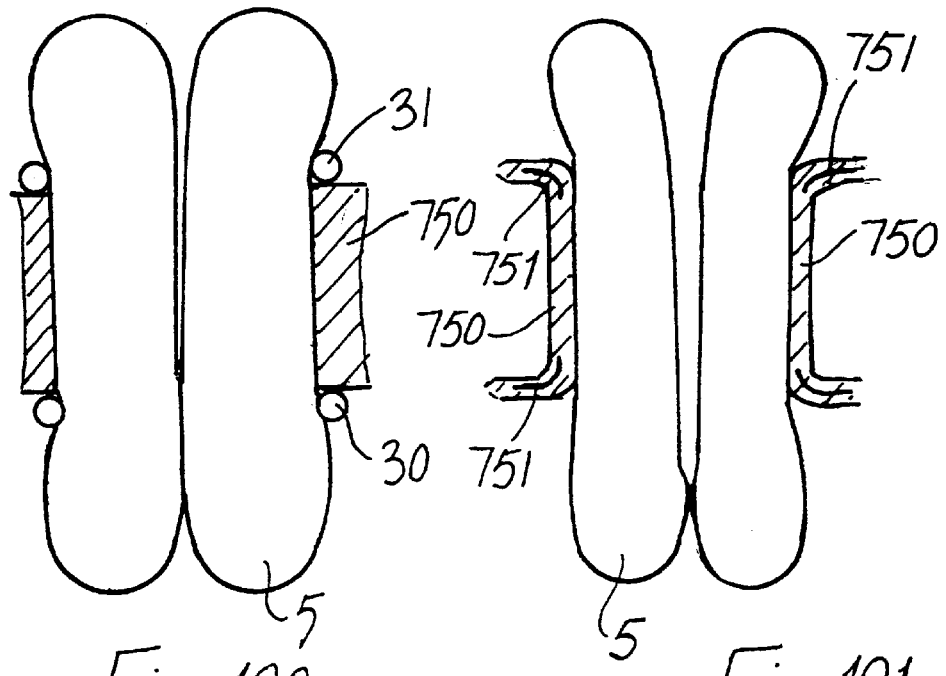
FIG. 100 illustrates another device in accordance with the invention.
FIG. 101 is a perspective, partially cut-away view of a further kind hand access device.
Figure 118:
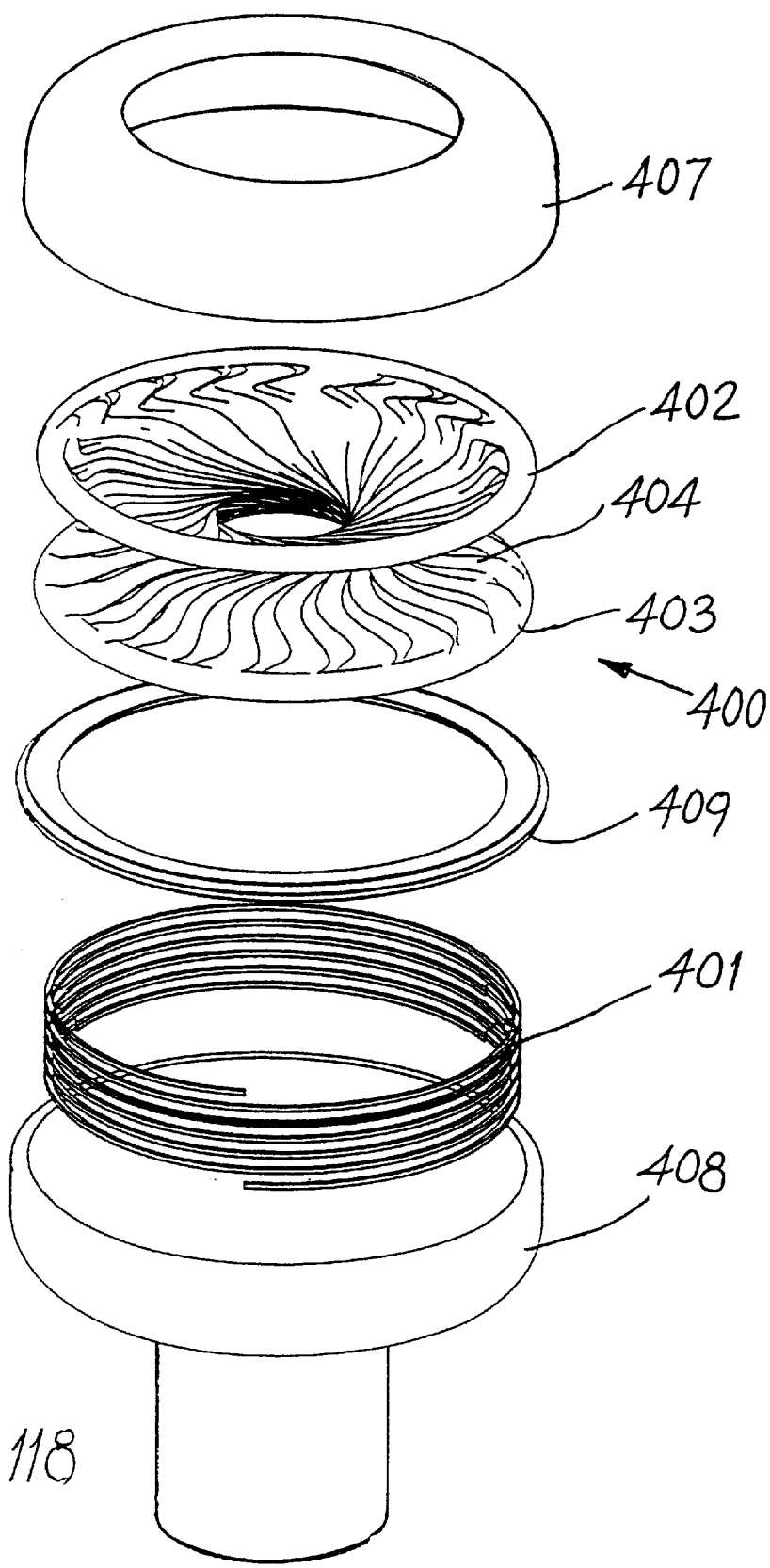
FIG. 118 is an exploded perspective view of another device according to the invention.
Figure 119:
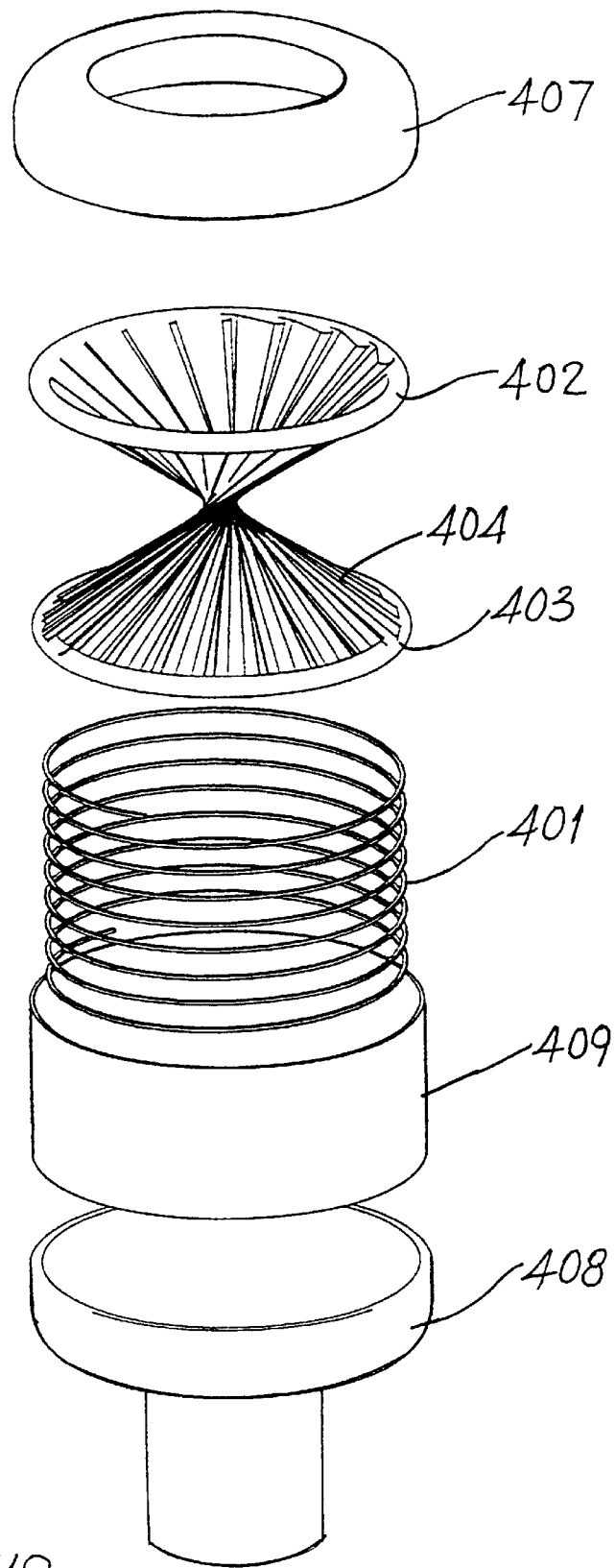
FIG. 119 is an exploded perspective view of the sealing device of FIG. 118 with the sleeve is an extended position.
Figure 120:
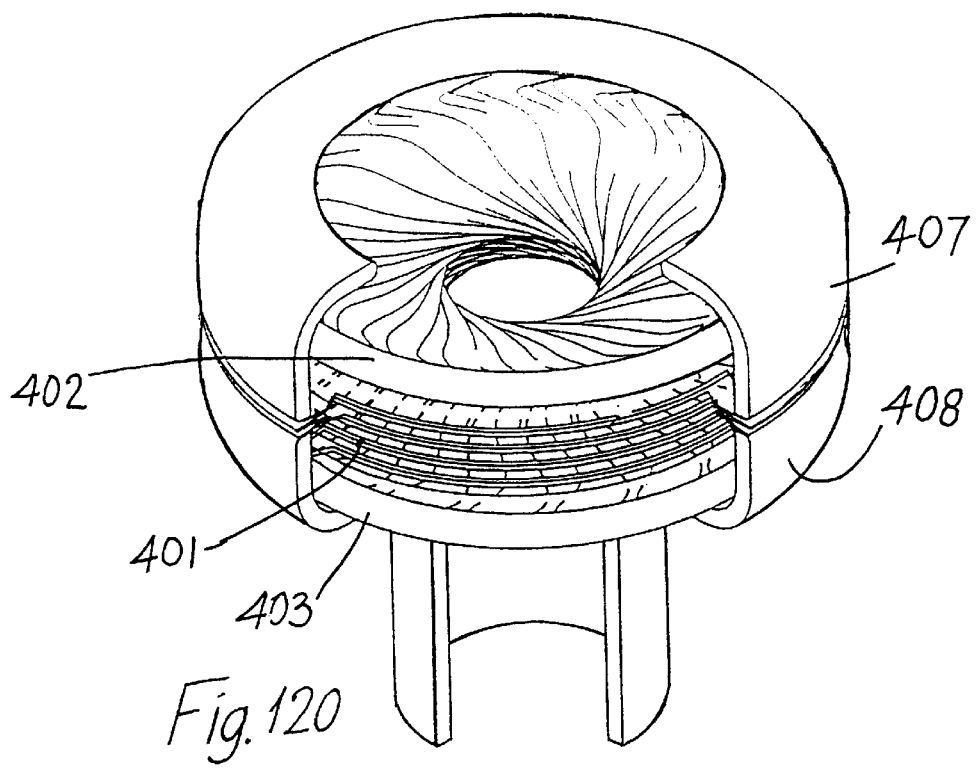
FIG. 120 is a perspective view of the sealing device of FIG. 118.
Figure 121:
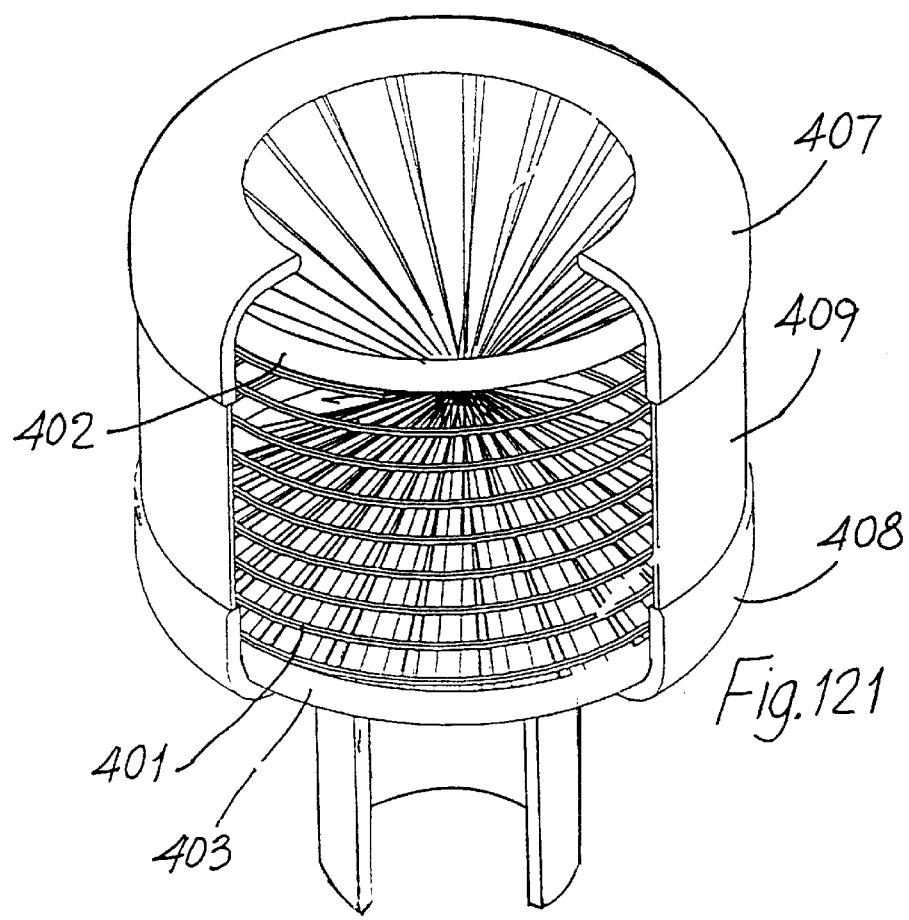
FIG. 121 is a perspective view of the sealing device of FIG. 118 with the sleeve in an extended position.
Figure 124:
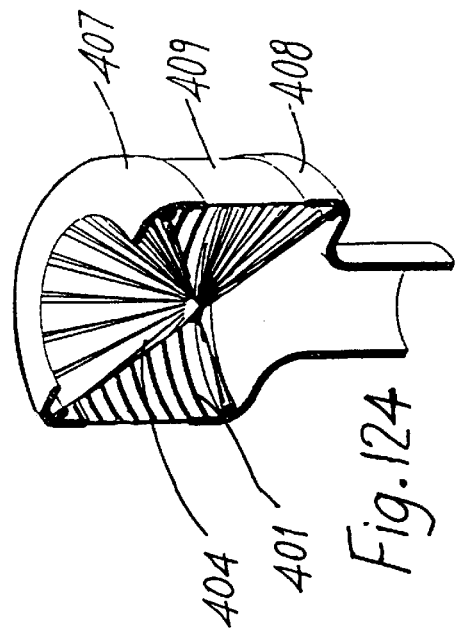
FIG. 124 is a perspective cross sectional view of the sealing device of FIG. 118 with the sleeve in an extended position.

Referring to FIG. 100, in this case the shield is provided by a compressible foam like sleeve 750. The foam may include stiffening means 751 as illustrated in FIG. 101. It will be appreciated that the shield may be of any suitable material.

Referring to FIGS. 102 to 109 there is illustrated a sealing device 250 according to the invention. The sealing device 250 comprises a tubular sleeve 251 of pliable material mounted at a first end to a first mounting means and mounted at a second end to a second mounting means. The first mounting means is a resilient ring 252, the second mounting means is a resilient ring 253. The sleeve 251 defines a lumen 254. The rings 252, 253 are rotated relative to one another to cause the sleeve 251 to twist, thereby reducing the diameter of the lumen 254. The sleeve 251 is illustrated in a twisted, flaccid position in FIGS. 102 to 105. The rings 252, 253 are moved away from each other in the axial direction, thereby extending the sleeve 251 and reducing the lumen diameter further, FIGS. 106 to 109.

The sleeve 251 is sealed around an object passing through the lumen 254;

(i) by rotating the rings 252, 253 relative to one another, thereby twisting the sleeve 1 and reducing the diameter of the lumen 254; or (ii) by moving the rings 252, 253 away from one another in the axial direction, thereby extending the sleeve 1 and reducing the diameter of the lumen 254; or (iii) by a combination of (i) and (ii).

Referring to FIGS. 110 to 117 there is illustrated a sealing device 300 which is similar to the sealing device 250 of FIGS. 102 to 109 and like parts are assigned the same reference numerals. In this case resilient struts 305 are connected between the first resilient ring and the second resilient ring. As the two rings are moved together, the struts 305 bend outwardly in a buckling manner. This causes the twisted sleeve to take up a flaccid configuration increasing the lumen diameter, FIGS. 114 to 117. The material properties of the struts 305 cause them to unbuckle when released. The struts 305 spring back to their straight positions parallel to the sleeve axis, FIGS. 110 to 113. The unbuckling of the struts 305 moves the two rings away from each other in the axial direction and extends the sleeve, thereby reducing the lumen diameter. In this case the sleeve is pre-twisted and the resilient rings are constrained by the struts 305 to remain in the twisted position. The resilient rings cannot rotate relative to one another.

Referring to FIGS. 118 to 125 there is illustrated another medical device 400 forming a trocar seal. In this case a coiled spring 401 is positioned between two resilient rings 402, 403 with a sleeve 404 therebetween. The upper end of the coiled spring 401 bears against the underside of the first ring 402 and the lower end of the coiled spring 401 bears against the top side of the second ring 403. The coiled spring 401 and sealing sleeve 404 are enclosed within a housing. The housing comprises a rigid casing having an upper part 407 and a lower part 408 which are separable from one another and a pliable tubular elastomeric sleeve 409 extending therebetween. The elastomeric sleeve 409 is sealed to the casing upper part and the casing lower part so that it joins the upper part and the lower part together. This arrangement facilitates the movement of the coiled spring 401 from a compressed position to an extended position, with the spring 401 remaining enclosed within the housing.

When the coiled spring 401 is compressed, the two rings 402, 403 move together. This causes the twisted sleeve to take up a flaccid configuration, increasing the lumen diameter. This compresses the elastomeric sleeve so that the upper and lower parts of the casing are adjacent to each other. When the coiled spring 401 is released, it moves to an extended position. This causes the two rings to move away from each other, extending the twisted sleeve and reducing the lumen diameter. The elastomeric sleeve is extended to a position in which the upper and lower parts of the casing are distal from each other. The device 400 is used for sealing a cannula.

Referring to FIGS. 126 and 127 there is illustrated a sealing device 500 according to the invention. In this case a twisted tubular sleeve 501 is mounted at one end to one end of a rigid tube 502 and at the other end to the other end of the rigid tube 502, with an enclosed volume 503 between the sleeve 501 and the rigid walls of the tube 502. The sleeve 501 is inflated by passing air through a port 504 in the tube 502 and into the enclosed volume 505. The inflation of the sleeve 501 extends the sleeve 501 in the axial direction, thereby reducing the lumen diameter.

Figure 125:
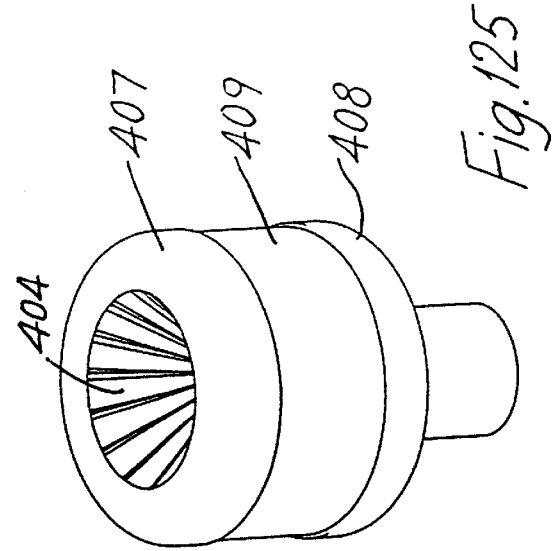
FIG. 125 is a perspective view of the sealing device of FIG. 118 with the sleeve in an extended position.
Figure 122:
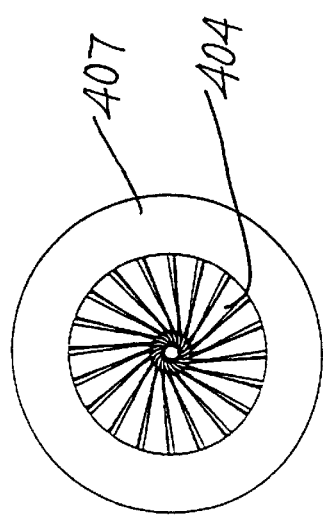
FIG. 122 is a plan view of the sealing device of FIG. 118 with the sleeve in an extended position.
Figure 123:
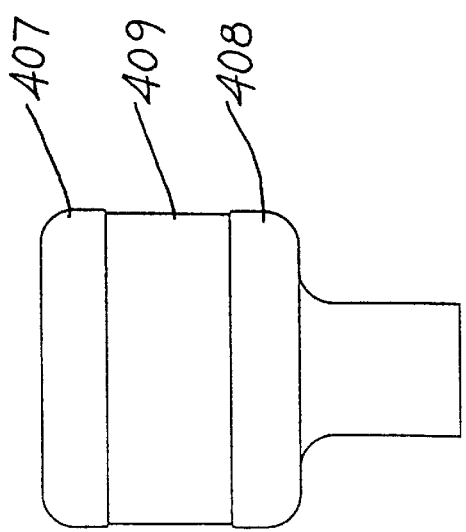
FIG. 123 is an elevational view of the sealing device of FIG. 118 with the sleeve in an extended position.

Referring to FIGS. 127 and 128 there is illustrated a sealing device 600 which is similar to the sealing device 500 of FIGS. 125 and 126. One end of a twisted tubular sleeve 601 is mounted to a first rigid tube 602, the other end of the twisted sleeve 501 is mounted to a second rigid tube 603. The rigid tubes 602, 603 partially overlap and are movable in an axial direction relative to one another, so that when the sleeve is inflated and extends in the axial direction, the tubes move axially away from one another in a "trombone-type" action, reducing the lumen diameter. The tubes are constrained at the overlapping ends so that they always overlap at least partially.

Reference is also made to appropriate alternatives and modifications which are outlined in our parallel applications referenced ATRO1/C, ATRO14/C/, ATRO15/C, ATRO16/C/, ATRO17/C, the entire contents of which are incorporated herein by reference.

The invention is not limited to the embodiments hereinbefore described which may be varied in construction and detail.

What is claimed is:

1. A medical sealing device for engaging an incision in a patient, comprising: a sleeve comprising,
   a sleeve wall having an incision engagable wall section and a central lumen wall section, and
   an inflation space surrounding the central lumen wall section, the central lumen wall section including a twisted wall portion for assisting sealed access through the central lumen wall section when the inflation space is inflated, and the twisted wall portion being twisted in a direction about a longitudinal axis of the sleeve.

2. A medical sealing device according to claim 1, further comprising at least one ring positioned adjacent an end portion of the incision engagable wall section for assisting in a positioning of the sleeve about the incision, the ring being orientated to lie in a plane generally perpendicular to the longitudinal axis of the sleeve.

3. A medical sealing device according to claim 2, wherein the at least one ring is axially movable in relation to the sleeve.

4. A medical sealing device according to claim 3, wherein the at least one ring is located within the inflation space.

5. A medical sealing device according to claim 2, wherein the at least one ring comprises two rings, one ring being axially movable in relation to the sleeve and the other ring being fixedly coupled to the sleeve.

6. A medical sealing device according to claim 2, wherein the at least one ring is a flexible O-ring.

7. A medical sealing device according to claim 2, wherein the at least one ring comprises two rings fixedly coupled to the sleeve, one ring coupled adjacent each end portion of the incision engagable wall section for assisting in maintaining the sleeve about the incision, each said ring being orientated to lie in a plane that is generally perpendicular to the longitudinal axis of the sleeve.

8. A medical sealing device according to claim 7, wherein the two rings are coupled to the sleeve outside of the inflation space.

9. A medical sealing device according to claim 7, wherein the two rings are coupled to the sleeve within the inflation space.

10. A medical sealing device according to claim 1, further comprising two rings located within the inflation space, said rings being axially spaced from each other and each lying in a plane generally perpendicular to the longitudinal axis of the sleeve.

11. A medical sealing device according to claim 10, wherein the two rings are each independently axially movable in relation to the sleeve.

12. A medical sealing device according to claim 10, wherein the two rings are coupled to each other and are together axially moveable in relation to the sleeve.

13. A medical sealing device according to claim 1, wherein the sleeve is formed of a pliable material.

14. A medical sealing device according to claim 1, wherein the incision engagable wall section is formed of a material different than the material of a remaining portion of the sleeve wall.

15. A medical sealing device according to claim 14, wherein the incision engagable wall section is formed of a material more flexible than the material of the remaining portion of the sleeve wall.

16. A medical sealing device according to claim 1, wherein the incision engagable wall section has approximately the same diameter as the twisted wall portion if measured when the inflation space is uninflated and the twisted wall portion were in an untwisted state.

17. A medical sealing device according to claim 1, wherein the twisted wall portion of the sleeve comprises a diameter smaller than a minimum diameter of an object to be received or passed through the lumen, the diameter of the twisted wall portion being measured when the inflation space is fully inflated.

18. A medical sealing device according to claim 17, wherein said object is one of a hand and a medical device.

19. A medical sealing device according to claim 1, further comprising an access port to the inflation space for assisting in an inflation of the inflation space.

20. A medical sealing device for engaging an incision in a patient, comprising:
    a sleeve comprising an incision engagable wall section, a movable wall section, and an inflation space,
    the movable wall section movable relative to the engagable wall section and forming at least a central lumen, the central lumen comprising a twisted wall portion for assisting sealed access through the lumen when the inflation space is inflated, and the twisted wall portion being twisted in a direction about a longitudinal axis of the sleeve.

21. A medical sealing device according to claim 20, further comprising at least one ring positioned at one end portion of the movable wall section for assisting in a positioning of the sleeve about the incision, the ring being orientated to lie in a plane generally perpendicular to the longitudinal axis of the sleeve.

22. A medical sealing device according to claim 21, wherein the at least one ring is axially movable in relation to the sleeve.

23. A medical sealing device according to claim 22, wherein the at least one ring is located within the inflation space.

24. A medical sealing device according to claim 21, wherein the at least one ring comprises two rings, one ring being axially movable in relation to the sleeve and the other ring being fixedly coupled to the sleeve.

25. A medical sealing device according to claim 21, wherein the at least one ring is a flexible O-ring.

26. A medical sealing device according to claim 21, wherein the at least one ring comprises two rings fixedly coupled to the sleeve, one ring coupled at each end portion of the movable wall section for assisting in maintaining the sleeve about the incision, each said ring being orientated to lie in a plane that is generally perpendicular to the longitudinal axis of the sleeve.

27. A medical sealing device according to claim 26, wherein the two rings are coupled to the sleeve outside of the inflation space.

28. A medical sealing device according to claim 26, wherein the two rings are coupled to the sleeve within the inflation space.

29. A medical sealing device according to claim 20, further comprising two rings located within the inflation space, said rings being axially spaced from each other and each lying in a plane generally perpendicular to the longitudinal axis of the sleeve.

30. A medical sealing device according to claim 29, wherein the two rings are each independently axially movable in relation to the sleeve.

31. A medical sealing device according to claim 29, wherein the two rings are coupled to each other and are together axially moveable in relation to the sleeve.

32. A medical sealing device according to claim 20, wherein the sleeve is formed of a pliable material.

33. A medical sealing device according to claim 20, wherein the incision engagable wall section is formed of a material different than the material forming the movable wall section.

34. A medical sealing device according to claim 33, wherein the incision engagable wall section is formed of a material more flexible than the material forming the movable wall section.

35. A medical sealing device according to claim 20, wherein the incision engagable wall section has approximately the same diameter as the twisted wall portion if measured when the inflation space is uninflated and the twisted wall portion were in an untwisted state.

36. A medical sealing device according to claim 20, wherein the twisted wall portion of the sleeve comprises a diameter smaller than a minimum diameter of an object to be received or passed through the lumen, the diameter of the twisted wall portion being measured when the inflation space is fully inflated.

37. A medical sealing device according to claim 36, wherein said object is one of a hand and a medical device.

38. A medical sealing device according to claim 20, further comprising an access port to the inflation space for assisting in an inflation of the inflation space.

39. A medical sealing device for engaging an incision in a patient, comprising:
   a sleeve comprising an incision engagable wall section, a movable wall section, and an inflation space;
   a proximal ring member located at a proximal end portion of the movable wall section and axially movable in relation to the sleeve member; and
   a distal ring member located at a distal end portion of the movable wall section,
   the proximal and distal ring members assisting in a positioning of the sleeve about the incision and being orientated to lie in a plane generally perpendicular to a longitudinal axis of the sleeve,
   the movable wall section movable relative to the engagable wall section and forming at least a central lumen, the central lumen comprising a twisted wall portion that is twisted in a direction about the longitudinal axis of the sleeve, and
   the movable wall section assisting in the sealing of an object extending through the central lumen and movable upon engagement and axial movement of the object with the central lumen by eversion so that a part of an inner portion of the sleeve moves to become a part of an outer portion of the sleeve and a section of the outer portion of the sleeve moves to become a section of the inner portion of the sleeve.

40. A medical sealing device according to claim 39, wherein the distal ring member is fixedly coupled to the sleeve.

41. A medical sealing device according to claim 39, wherein the proximal and distal ring members each comprise a flexible O-ring.

42. A medical sealing device according to claim 39, wherein the sleeve is formed of a pliable material.

43. A medical sealing device according to claim 39, wherein the incision engagable wall section is formed of a material different than the material forming the movable wall section.

44. A medical sealing device according to claim 39, wherein the incision engagable wall section has approximately the same diameter as the twisted wall portion if measured when the inflation space is uninflated and the twisted wall portion were in an untwisted state.

45. A medical sealing device according to claim 39, wherein the twisted wall portion of the sleeve comprises a diameter smaller than a minimum diameter of an object to be received or passed through the lumen, the diameter of the twisted wall portion being measured when the inflation space is fully inflated.

46. A medical sealing device according to claim 45, wherein said object is one of a hand and a medical device.

47. A medical sealing device according to claim 39, further comprising an access port to the inflation space for assisting in an inflation of the inflation space.

48. A medical sealing device for engaging an incision in a patient, comprising:
   a sleeve comprising an incision engagable wall section, a movable wall section, and an inflation space; and
   a ring member located at an end portion of the movable wall section for assisting in a positioning of the sleeve about the incision,
   the movable wall section movable relative to the engagable wall section and forming at least a central lumen, the central lumen comprising a twisted wall portion that is twisted in a direction about the longitudinal axis of the sleeve,
   the movable wall section assisting in the sealing of an object extending through the central lumen and movable upon engagement and axial movement of the object with the central lumen by eversion so that a part of an inner portion of the sleeve moves to become a part of an outer portion of the sleeve and a section of the outer portion of the sleeve moves to become a section of the inner portion of the sleeve, and
   the incision engagable wall section having approximately the same diameter as the twisted wall portion if measured when the inflation space is uninflated and the twisted wall portion were in an untwisted state.

49. A medical sealing device for engaging an incision in a patient, comprising: a sleeve having at least a central lumen section capable of receiving an object extending therethrough, the central lumen section having a twisted wall portion twisted in a direction about a longitudinal axis of the sleeve, and the sleeve further including an axially non-extended configuration when the object is received within the central lumen, and an axially extended configuration when the object is sealingly engaged within the central lumen, the central lumen section including a smaller diameter in the axially extended configuration than in the axially non-extended configuration, and the sleeve further including an inflation space surrounding the central lumen, and inflation of the inflation space urges the sleeve into contact with the object and into the extended configuration.

50. A medical sealing device for engaging an incision in a patient, comprising: a sleeve having at least a central lumen section capable of receiving an object extending therethrough, the central lumen section having a twisted wall portion twisted in a direction about a longitudinal axis of the sleeve, and the sleeve further including an axially non-extended configuration when the object is received within the central lumen, and an axially extended configuration when the object is sealingly engaged within the central lumen, the central lumen section including a smaller diameter in the axially extended configuration than in the axially non-extended configuration, the medical sealing device further including a tension spring member coupled to the sleeve, and compression of the spring member urges the sleeve out of contact with the object and into the non-extended configuration.

51. A medical sealing device according to claim 49, further comprising at least one ring positioned adjacent an end portion of an incision engagable wall section of the sleeve, the at least one ring assisting in a positioning of the sleeve about the incision, the ring being orientated to lie in a plane generally perpendicular to the longitudinal axis of the sleeve.

52. A medical sealing device according to claim 51, wherein the at least one ring comprises two rings, one ring located adjacent opposing end portions of the incision engagable wall section.

53. A medical sealing device according to claim 49, wherein the sleeve further includes an incision engagable wall section formed of a material more flexible than the material of the remaining portion of the sleeve.

54. A medical sealing device according to claim 49, wherein said object is one of a hand and a medical device.

55. A medical sealing device for engaging an incision in a patient, comprising:
   a housing comprising a distal portion having an incision engaging section, a proximal portion, and an axial opening extending through the housing, the proximal portion being movable relative to the distal portion;
   a spring member located within the housing;
   a twisted sleeve member located within the housing, coupled to the spring member, and comprising an adjustable opening for assisting in sealed access through the axial opening and into the patient, the adjustable opening being aligned with the axial opening of the housing and adjusted by urging the spring in a compression direction.

56. A medical sealing device according to claim 55, wherein the spring member is coupled to a proximal end portion of the twisted sleeve member and to a distal end portion of the twisted sleeve member.

57. A medical sealing device according to claim 55, wherein the distal portion of the housing comprises a reduced diameter portion and a receiving portion for accepting the spring member and twisted sleeve member; and the proximal portion comprises a cap member engagable and axially movable relative to the distal portion, wherein movement of the cap member toward the distal portion of the housing assists in compressing both the spring member and the twisted sleeve member to enlarge the adjustable opening of the twisted sleeve member.

58. A medical sealing device according to claim 57, wherein the receiving portion of the housing comprises a flexible tube.

59. A method for providing sealed access through an incision in a patient, comprising the steps of: placing a hand access device into communication with the incision, the access device comprising a sleeve member having a first end, a second end and a central lumen having a twisted wall portion twisted about a longitudinal axis of the sleeve member; introducing an object within at least a portion of the central lumen of the sleeve member; applying a force to the sleeve member so that the central lumen sealingly engages the object, the force causing an increase in the axial distance between the first and second end and a decrease in a diameter of the central lumen, as compared to the axial distance between the first and second end and diameter of the central lumen when the object extends through the lumen without application of the force, and the sleeve member includes an inflation space and the force is applied by inflating the inflation space.

60. A method for providing sealed access through an incision in a patient, comprising the steps of: placing a hand access device into communication with the incision, the access device comprising a sleeve member having a first end, a second end and a central lumen having a twisted wall portion twisted about a longitudinal axis of the sleeve member; introducing an object within at least a portion of the central lumen of the sleeve member; applying a force to the sleeve member so that the central lumen sealingly engages the object, the force causing an increase in the axial distance between the first and second end and a decrease in a diameter of the central lumen, as compared to the axial distance between the first and second end and diameter of the central lumen when the object extends through the lumen without application of the force, and the force is applied by a tension spring member coupled to the sleeve member.

61. A medical sealing device formed by a process comprising:
   twisting a flexible sleeve member about its longitudinal axis so that a proximal end portion is rotated relative to a distal end portion;
   folding the proximal end portion and distal end portion radially outward; sealingly attaching the proximal and distal end portions together so as to form an inflatable chamber.

62. A medical sealing device formed by a process according to claim 61, further comprising coupling ring members to the flexible sleeve member to assist in positioning the sealing device during use.

63. A medical sealing device formed by a process according to claim 62, wherein the ring members are flexible ring members.

64. A medical sealing device formed by a process according to claim 61, further comprising coupling a valve member to the inflatable chamber to assist in inflating the inflatable chamber.

* * * * *

UNITED STATES PATENT AND TRADEMARK OFFICE
CERTIFICATE OF CORRECTION

PATENT NO. : 6,578,577 B2
DATED : June 17, 2003
INVENTOR(S) : Frank Bonadio et al.

It is certified that error appears in the above-identified patent and that said Letters Patent is hereby corrected as shown below:

Column 20,
Line 54, before "the sleeve further including", delete "and".

Signed and Sealed this

Fifth Day of August, 2003

JAMES E. ROGAN
*Director of the United States Patent and Trademark Office*